(12) United States Patent
Dallel et al.

(10) Patent No.: US 12,351,556 B2
(45) Date of Patent: Jul. 8, 2025

(54) PYRIDIN-2(1H)ONE DERIVATIVES, THEIR PREPARATION AND THEIR USE FOR THE TREATMENT OF PAIN

(71) Applicants: INSTITUT NATIONAL DE LA SANTE ET DE LA RECHERCHE MEDICALE (INSERM), Paris (FR); CENTRE HOSPITALIER UNIVERSITAIRE DE CLERMONT-FD, Clermont-Ferrad (FR); SIGMA CLERMONT, Aubiere (FR); CENTRE NATIONAL DE LA RECHERCHE SCIENTIFIQUE, Paris (FR); UNIVERSITÉ CLERMONT AUVERGNE, Clermont-Ferrand (FR)

(72) Inventors: Radhouane Dallel, Clermont-Ferrand (FR); Alain Artola, Clermont-Ferrand (FR); Amélie Descheemaeker, Clermont-Ferrand (FR); Fabrice Anizon, Aubiere (FR); Isabelle Thomas, Aubiere (FR); Pascale Moreau, Aubiere (FR); Alexia Visseq, At Groningen (NL); Francis Giraud, Aubiere (FR)

(73) Assignees: INSERM (INSTITUT NATIONAL DE LA SANTE ET DE LA RECHERCHE MEDICALE), Paris (FR); CENTRE HOSPITALIER UNIVERSITAIRE DE CLERMONT-FD, Clermont-Ferrad (FR); SIGMA CLERMONT, Aubiere (FR); CENTRE NATIONAL DE LA RECHERCHE SCIENTIFIQUE (CNRS), Paris (FR); UNIVERSITE CLERMONT AUVERGNE, Clermont-Ferrand (FR)

( * ) Notice: Subject to any disclaimer, the term of this patent is extended or adjusted under 35 U.S.C. 154(b) by 644 days.

(21) Appl. No.: 17/762,431

(22) PCT Filed: Oct. 2, 2020

(86) PCT No.: PCT/EP2020/077684
§ 371 (c)(1),
(2) Date: Mar. 22, 2022

(87) PCT Pub. No.: WO2021/064186
PCT Pub. Date: Apr. 8, 2021

(65) Prior Publication Data
US 2022/0363643 A1    Nov. 17, 2022

(30) Foreign Application Priority Data

Oct. 4, 2019    (EP) ..................................... 19306284

(51) Int. Cl.
| | | |
|---|---|---|
| *C07D 213/76* | (2006.01) | |
| *A61P 25/04* | (2006.01) | |
| *C07D 213/73* | (2006.01) | |
| *C07D 213/74* | (2006.01) | |
| *C07D 401/04* | (2006.01) | |
| *C07D 401/14* | (2006.01) | |

(52) U.S. Cl.
CPC ............ *C07D 213/76* (2013.01); *A61P 25/04* (2018.01); *C07D 213/73* (2013.01); *C07D 213/74* (2013.01); *C07D 401/04* (2013.01); *C07D 401/14* (2013.01)

(58) Field of Classification Search
CPC .. C07D 213/76; C07D 213/73; C07D 213/74; C07D 401/04; C07D 401/14; A61P 25/04
See application file for complete search history.

(56) References Cited

U.S. PATENT DOCUMENTS

2007/0281948 A1    12/2007  Peukert et al.
2020/0247812 A1*    8/2020  Chakravarty ........... A61P 35/00

FOREIGN PATENT DOCUMENTS

| WO | 03068748 A1 | 8/2003 |
| WO | 2008140066 A2 | 11/2008 |
| WO | 2020012357 A1 | 1/2020 |

* cited by examiner

*Primary Examiner* — D Margaret M Seaman
(74) *Attorney, Agent, or Firm* — WCF IP

(57) ABSTRACT

The present invention concerns novel pyridin-2(1H)one derivatives, their process of preparation and their use in therapeutics, in particular as agents for treating and/or preventing pain.

8 Claims, 4 Drawing Sheets

A

B

PYRIDIN-2(1H)ONE DERIVATIVES, THEIR PREPARATION AND THEIR USE FOR THE TREATMENT OF PAIN

Chronic pain is a worldwide major health, social and economic problem. It has an important impact on quality of life across all ages, and is the most common reason for seeking medical care. Global economic impact of pain is tremendous. Estimates show that chronic pain affects more than 20% of Europeans and costs several hundred billion each year in medical treatment and loss of productivity, with an expected increase due to population ageing.

Despite significant investments in research and development to study pain mechanisms and discover new treatments, most analgesics available today are still based on old drug classes: nonsteroidal anti-inflammatory drugs (NSAIDs), acetaminophen, opioids, anticonvulsants or antidepressants. Moreover, these therapies have strong side-effects or abuse potentials, and are not always effective. Whereas most currently available treatments can alleviate inflammatory pain (initiated by tissue damage/inflammation), they are only partially effective for neuropathic pain (caused by nervous system lesions). Thus, chronic pain still constitutes an unmet medical need with a strong demand of the market for new efficient treatments.

Chronic pain syndromes, whether they are inflammatory or neuropathic, are characterized by persistent pain hypersensitivity such as spontaneous pain, hyperalgesia and allodynia.

Mechanical allodynia (MA), or touch-evoked pain, is one of the most prevalent pain symptoms, being present in almost half of neuropathic patients. It was recently shown that it is associated with the activation, in the spinal dorsal horn (SDH) or medullary dorsal horn (MDH) (SDH trigeminal homologue in the brainstem), of a polysynaptic pathway whereby tactile inputs can gain access to the pain circuitry in superficial SDH/MDH. MA thus results from a miscoding, with cells that normally transmit and respond to noxious stimuli being activated by tactile inputs.

Therefore, it is pivotal to discover drugs that specifically target the fundamental mechanisms causing the various pain symptoms.

Activation of several neuronal protein kinases (PK) within the superficial SDH/MDH, such as extracellular signal-regulated protein kinases (ERK), the γ isoform of protein kinase C (PKCγ) or p38 mitogen-activated protein kinase (p38 MAPK), was shown to contribute to pain hypersensitivity in animal models of chronic inflammatory and neuropathic pain. Thus, inhibitors of ERK phosphorylation reduce MA and hyperalgesia. Genetic or pharmacological inactivation of PKCγ prevents MA whereas its activation is sufficient to produce MA. Finally, inhibition of SDH/MDH p38 MAPK attenuates inflammatory as well as neuropathic pain. Therefore, PKs are possible cellular targets to alleviate MA.

WO2009021696 discloses phenylaminopyridine derivatives, and their use as DHODH inhibitors.

The present invention provides for new derivatives as anti-pain agents, in particular as anti-allodynic agents. Notably, the compounds have been shown to be selective for p38α MAPK.

According to a first object, the present invention concerns a compound of Formula (I):

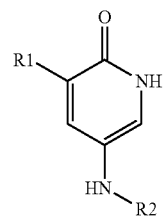

(I)

Wherein:
R1 represents a mono or bicyclic 3 to 12-membered aryl, heteroaryl, carbocyclic or heterocyclic ring, optionally comprising one to 6 heteroatoms chosen from N, O or S, and optionally substituted by one or more, identical or different groups chosen from halogen atoms, —C(=O)OR, —C(=O)NRR', NRR', NO$_2$, C6-C12 aryl, —C(=O)R, OH, OR, C1-C6 alkyl, CF$_3$, —OCF$_3$, CN, NH—C(=O)—C1-C6 alkyl, O—C(=O)—C1-C6 alkyl, NH—C1-C6 alkyl-NRR', O—C1-C6 alkyl-NRR', C1-C6 alkyl-NRR';

R2 represents a mono or bicyclic 3 to 12-membered aryl, heteroaryl, carbocyclic or heterocyclic ring, optionally comprising one to 6 heteroatoms chosen from N, O or S, and optionally substituted by one or more, identical or different groups chosen from halogen, —C(=O)OR, —C(=O)NRR', NRR', NO$_2$, C6-C12 aryl, —C(=O)R, OH, OR, C1-C6 alkyl, CF$_3$, —OCF$_3$, CN, NH—C(=O)—C1-C6 alkyl, O—C(=O)—C1-C6 alkyl, NH—C1-C6 alkyl-NRR', O—C1-C6 alkyl-NRR', C1-C6 alkyl-NRR';

Wherein R and R', identical or different are H or a C1-C6 alkyl or C6-C12 aryl or a pharmaceutically acceptable salt thereof.

According to an embodiment, R1 is a 4-indolyl group. In particular, R2 may then be selected from the group consisting in:
phenyl optionally substituted by one or more of halogen atom, a O—C1-C6 Alkyl, a COO—C1-C6 Alkyl, NO$_2$, C1-C6 Alkyl, OH or NH$_2$; pyridyl.

According to another embodiment, R2 is a phenyl group. In particular, R1 may then be a group selected from the group consisting in:
Pyridyl;
Pyrimidinyl;
Isoquinolinyl;
Quinolyl;
Indolyl;
Phenyl optionally substituted by one or more of halogen atom, a COO—C1-C6 Alkyl, a CO—C1-C6 Alkyl, a CONH$_2$, NO$_2$, C1-C6 Alkyl, OH, phenyl, OCF$_3$, CF$_3$, or NH$_2$.

According to a further embodiment, said compound may be chosen from:
3-Phenyl-5-(phenylamino)pyridin-2(1H)-one (19)
3-(4-Fluorophenyl)-5-(phenylamino)pyridin-2(1H)-one (20)
5-(Phenylamino)-[3,4'-bipyridin]-2(1H)-one (21)
3-(1H-Indol-3-yl)-5-(phenylamino)pyridin-2(1H)-one (22)
5-(Phenylamino)-3-(quinolin-8-yl)pyridin-2(1H)-one (23)
5-(Phenylamino)-3-(pyrimidin-5-yl)pyridin-2(1H)-one (24)
3-(Isoquinolin-5-yl)-5-(phenylamino)pyridin-2(1H)-one (25)
5-(Phenylamino)-3-(quinolin-4-yl)pyridin-2(1H)-one (66)
3-(1H-Indol-4-yl)-5-(phenylamino)pyridin-2(1H)-one (67)

3-(2-Chlorophenyl)-5-(phenylamino)pyridin-2(1H)-one (68)
3-(2-Bromophenyl)-5-(phenylamino)pyridin-2(1H)-one (69)
Ethyl 2-(2-oxo-5-(phenylamino)-1,2-dihydropyridin-3-yl)benzoate (70)
2-(2-Oxo-5-(phenylamino)-1,2-dihydropyridin-3-yl)benzamide (71)
3-(2-Nitrophenyl)-5-(phenylamino)pyridin-2(1H)-one (72)
3-([1,1'-biphenyl]-4-yl)-5-(phenylamino)pyridin-2(1H)-one (73)
3-(3-Chlorophenyl)-5-(phenylamino)pyridin-2(1H)-one (74)
3-(3-Acetylphenyl)-5-(phenylamino)pyridin-2(1H)-one (75)
3-(4-Hydroxyphenyl)-5-(phenylamino)pyridin-2(1H)-one (76)
5-(Phenylamino)-3-(p-tolyl)pyridin-2(1H)-one (77)
5-(Phenylamino)-3-(4-(trifluoromethyl)phenyl)pyridin-2(1H)-one (78)
5-(Phenylamino)-3-(4-(trifluoromethoxy)phenyl)pyridin-2(1H)-one (79)
Methyl 4-(2-oxo-5-(phenylamino)-1,2-dihydropyridin-3-yl)benzoate (80)
4-(2-Oxo-5-(phenylamino)-1,2-dihydropyridin-3-yl)benzamide (81)
3-(2,4-Difluorophenyl)-5-(phenylamino)pyridin-2(1H)-one (82)
3-(1H-Indol-7-yl)-5-(phenylamino)pyridin-2(11-1)-one (83)
3-(3-Aminophenyl)-5-(phenylamino)pyridin-2(1H)-one (84)
5-((3-Hydroxyphenyl)amino)-3-(1H-indol-4-yl)pyridin-2(11-1)-one (85)
5-((2-Fluorophenyl)amino)-3-(1H-indol-4-yl)pyridin-2(1H)-one (118)
5-((3-Fluorophenyl)amino)-3-(1H-indol-4-yl)pyridin-2(1H)-one (119)
5-((4-Fluorophenyl)amino)-3-(1H-indol-4-yl)pyridin-2(1H)-one (120)
3-(1H-Indol-4-yl)-5-((2-methoxyphenyl)amino)pyridin-2(1H)-one (121)
3-(1H-Indol-4-yl)-5-((3-methoxyphenyl)amino)pyridin-2(1H)-one (122)
3-(1H-Indol-4-yl)-5-((4-methoxyphenyl)amino)pyridin-2(1H)-one (123)
Ethyl 2-((5-(1H-indol-4-yl)-6-oxo-1,6-dihydropyridin-3-yl)amino)benzoate (124)
Ethyl 3-((5-(1H-indol-4-yl)-6-oxo-1,6-dihydropyridin-3-yl)amino)benzoate (125)
Ethyl 4-((5-(1H-indol-4-yl)-6-oxo-1,6-dihydropyridin-3-yl)amino)benzoate (126)
3-(1H-Indol-4-yl)-5-((2-nitrophenyl)amino)pyridin-2(1H)-one (127)
3-(1H-Indol-4-yl)-5-((3-nitrophenyl)amino)pyridin-2(1H)-one (128)
3-(1H-Indol-4-yl)-5-((4-nitrophenyl)amino)pyridin-2(1H)-one (129)
3-(1H-Indol-4-yl)-5-(o-tolylamino)pyridin-2(1H)-one (130)
3-(1H-Indol-4-yl)-5-(pyridin-2-ylamino)pyridin-2(1H)-one (131)
3-(1H-Indol-4-yl)-5-(pyridin-3-ylamino)pyridin-2(1H)-one (132)
3-(1H-Indol-4-yl)-5-(pyridin-4-ylamino)pyridin-2(1H)-one (133)
5-((3-hydroxyphenyl)amino)-3-(1H-indol-4-yl)pyridin-2(1H)-one (134)
5-((2-Aminophenyl)amino)-3-(1H-indol-4-yl)pyridin-2(1H)-one (135)
5-((2-Bromophenyl)amino)-3-(1H-indol-4-yl)pyridin-2(1H)-one (141)
5-((3-Bromophenyl)amino)-3-(1H-indol-4-yl)pyridin-2(1H)-one (142)
5-((4-Bromophenyl)amino)-3-(1H-indol-4-yl)pyridin-2(1H)-one (143)
3-(2-Aminophenyl)-5-(phenylamino)pyridin-2(11-1)-one (144)
5-((2-Hydroxyphenyl)amino)-3-(1H-indol-4-yl)pyridin-2(11-1)-one (145)
5-((4-Hydroxyphenyl)amino)-3-(1H-indol-4-yl)pyridin-2(11-1)-one (146)
5-((3-Aminophenyl)amino)-3-(1H-indol-4-yl)pyridin-2(11-1)-one (147)

and the pharmaceutically acceptable salts thereof.

Unless specified otherwise, the terms used hereabove or hereafter have the meaning ascribed to them below:

"Halo", "hal" or "halogen" refers to fluorine, chlorine, bromine or iodine atom.

"Alkyl" or C1-C6 alkyl represents an aliphatic-hydrocarbon group which may be straight or branched having 1 to 6 carbon atoms in the chain. In a particularly preferred embodiment the alkyl group has 1 to 4 carbon atoms in the chain. Exemplary alkyl groups include methyl, ethyl, n-propyl, iso-propyl, iso-butyl, n-butyl, tert-butyl, n-pentyl, 2-pentyl, 3-pentyl.

The term "aryl" refers to an aromatic carbo, mono- or bicyclic hydrocarbon ring containing from 6 to 14, preferably 6 to 12, still preferably 6 to 10 carbon atoms. Examples include phenyl, naphthyl, indenyl, etc.

The term "heteroaryl" refers to a 5 to 14, preferably 3 to 12, still preferably 5 to 10 membered aromatic hetero, mono- or bicyclic ring. Examples include pyrrolyl, pyridyl, pyrazolyl, thienyl, pyrimidinyl, pyrazinyl, tetrazolyl, indolyl, quinolinyl, purinyl, imidazolyl, thiazolyl, benzothiazolyl, furanyl, benzofuranyl, 1,2,4-thiadiazolyl, isothiazolyl, triazoyl, isoquinolyl, benzothienyl, isobenzofuryl, carbazolyl, benzimidazolyl, isoxazolyl, pyridyl-N-oxide groups.

As used herein, the term "aromatic" refers to, in the definitions of aryl or heteroaryl, a cyclically carbocyclic aryl or heteroaryl system as defined herein, which satisfies the Hückel (4n+2) rule and/or with a stability due to delocalization significantly greater than that of a hypothetic localized structure.

The term "carbocyclic" refers to mono or bicyclic unsaturated non aromatic hydrocarbon rings comprising 3 to 12 carbon atoms.

The terms "heterocycle" or "heterocyclic" refer to a saturated, partially unsaturated or unsaturated non aromatic stable 3 to 14, preferably 5 to 10 membered mono- or bicyclic rings wherein at least one member of the ring is a hetero atom. Typically, heteroatoms include, but are not limited to, oxygen, nitrogen and sulfur atoms. Preferable heteroatoms are oxygen, nitrogen and sulfur. The nitrogen and sulfur heteroatoms may be optionally oxidized, and the nitrogen may be optionally substituted in non-aromatic rings. Preferred heterocyclic groups include, but are not limited to oxiranyl, tetrahydrofuranyl, dioxolanyl, tetrahydropyranyl, dioxanyl, pyrrolidinyl, piperidyl, morpholinyl, imidazolidinyl, pyranyl, imidazolinyl, pyrrolinyl, pyrazolinyl, piperazinyl.

The compounds of the present invention may possess an acidic group or a basic group which may form corresponding salts. Thus the present invention includes salts of compounds of Formula (I). The salts may preferably be pharmaceutically acceptable salts. The acidic group may form salts with bases. The base may be an organic amine base, for example triethylamine, tert-butylamine, tromethamine, meglumine, epolamine, etc. The acidic group may also form salts with inorganic bases like sodium hydroxide, potassium hydroxide, etc. The basic group may form salts with inorganic acids like hydrochloric acid, sulfuric acid, hydrobromic acid, sulfamic acid, phosphoric acid, nitric acid, etc and organic acids like acetic acid, propionic acid, succinic acid, tartaric acid, citric acid, methanesulfonic acid, benzenesulfonic acid, trifluoroacetic acid, glucuronic acid, glutamic acid, benzoic acid, salicylic acid, toluenesulfonic acid, oxalic acid, fumaric acid, maleic acid etc. Further, compounds of Formula (I) may form quaternary ammonium salts and salts with amino acids such as arginine, lysine, etc. Lists of suitable salts may be found in Remington's Pharmaceutical Sciences, 17th ed., Mack Publishing Company, Easton, PA, 1985, p. 1418 and P. H. Stahl, C. G. Wermuth, *Handbook of Pharmaceutical salts-Properties, Selection and Use*, Wiley-VCH, 2002, the disclosures of which are hereby incorporated by reference.

These salts are advantageously prepared with pharmaceutically acceptable bases or acids, but salts with other bases or acids, useful for example for the purification or for the isolation of the compounds of Formula (I), also form part of the invention.

The compounds of Formula (I) can comprise one or more asymmetric carbon atoms. They can therefore exist in the form of enantiomers or diastereoisomers. These enantiomers and diastereoisomers, as well as their mixtures, including racemic mixtures, form part of the invention.

It is well known in the art how to prepare and isolate such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

The compounds of Formula (I) can also be provided in the form of a hydrate or of a solvate, i.e. in the form of associations or combinations with one or more water or solvent molecules. Such hydrates and solvates also form part of the invention.

According to another object, the present invention concerns the process of preparation of a compound of Formula (I) according to the invention as defined above.

The compounds and process of the present invention may be prepared in a number of ways well known to those skilled in the art. The compounds can be synthesized, for example, by application or adaptation of the methods described below, or variations thereon as appreciated by the skilled artisan. The appropriate modifications and substitutions will be readily apparent and well known or readily obtainable from the scientific literature to those skilled in the art. In particular, such methods can be found in R. C. Larock, *Comprehensive Organic Transformations*, VCH publishers, 1989.

The reagents and starting materials may be commercially available, or readily synthesized by well-known techniques by one of ordinary skill in the arts. All substituents, unless otherwise indicated, are as previously defined.

In the reactions described hereinafter, it may be necessary to protect reactive functional groups, for example hydroxy, amino, imino, thio or carboxy groups, where these are desired in the final product, to avoid their unwanted participation in the reactions. Conventional protecting groups herein named Pg may be used in accordance with standard practice, for examples see T. W. Greene and P. G. M. Wuts in *Protective Groups in Organic Synthesis*, John Wiley and Sons, 1991; J. F. W. McOmie in *Protective Groups in Organic Chemistry*, Plenum Press, 1973.

Some reactions may be carried out in the presence of a base. There is no particular restriction on the nature of the base to be used in this reaction, and any base conventionally used in reactions of this type may equally be used here, provided that it has no adverse effect on other parts of the molecule. Examples of suitable bases include: sodium hydroxide, potassium carbonate, sodium carbonate, cesium carbonate, triethylamine, alkali metal hydrides, such as sodium hydride and potassium hydride; alkyllithium compounds, such as methyllithium and butyllithium; and alkali metal alkoxides, such as sodium methoxide and sodium ethoxide.

Usually, reactions are carried out in a suitable solvent. A variety of solvents may be used, provided that it has no adverse effect on the reaction or on the reagents involved. Examples of suitable solvents include: hydrocarbons, which may be aromatic, aliphatic or cycloaliphatic hydrocarbons, such as hexane, cyclohexane, benzene, toluene and xylene; amides, such as dimethylformamide; alcohols such as ethanol and methanol and ethers, such as diethyl ether and tetrahydrofuran.

The reactions can take place over a wide range of temperatures. In general, it was found convenient to carry out the reaction at a temperature ranging from −78° C. to 150° C. (more preferably from about room temperature to 100° C.). The time required for the reaction may also vary widely, depending on many factors, notably the reaction temperature and the nature of the reagents. However, provided that the reaction is effected under the preferred conditions outlined above, a period ranging from 2 hours to 30 hours will usually suffice. The compound thus prepared may be recovered from the reaction mixture by conventional means. For example, the compounds may be recovered by distilling off the solvent from the reaction mixture or, if necessary after distilling off the solvent from the reaction mixture, pouring the residue into water followed by extraction with a water-immiscible organic solvent and distilling off the solvent from the extract. Additionally, the product can, if desired, be further purified by various well-known techniques, such as recrystallization, reprecipitation or the various chromatography techniques, notably column chromatography or preparative thin layer chromatography.

In particular, the process of preparation of a compound of Formula (I) comprises the step of deprotecting a compound of Formula (II):

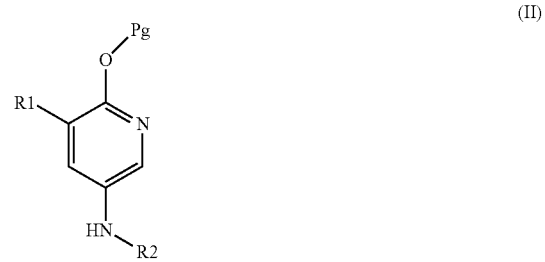

(II)

Where R1 and R2 are defined as in Formula (I) above, and Pg is a protecting group of hydroxyl.

The process may further comprise the step of isolating the obtained compound of Formula (I).

Typical hydroxyl protecting groups include acetyl, benzoyl, benzyl, β-Methoxyethoxymethyl ether (MEM), Dimethoxytrityl, [bis-(4-methoxyphenyl)phenylmethyl] (DMT), Methoxymethyl ether (MOM), Pivaloyl (Piv), Tetrahydropyranyl (THP), Tetrahydrofuran (THF), etc . . . .

Deprotection may be achieved by application or adaptation of known procedures, such as those disclosed by Greene et al. (supra).

According to an embodiment, Pg is benzyl. It may be typically removed by using $BBr_3$, TMSI or by catalytic hydrogenation.

The compound of Formula (II) may be obtained by two alternative routes:

According to a first route, the compound of Formula (II) may be obtained by reacting a compound of Formula (III):

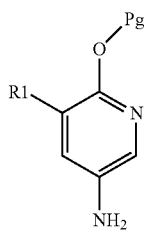
(III)

With a compound of Formula (A):

R2-Hal                                (A)

Where R1 and R2 are defined as in Formula (I), Pg is defined as in Formula (II) and Hal is a halogen atom, such as I or Br.

Typically, the reaction is a carbon-nitrogen coupling, such as the Buchwald-Hartwig coupling.

This reaction may be conducted in the presence of $Pd(OAc)_2$, 4,5-Bis(diphenylphosphino)-9,9-dimethylxanthene (Xantphos), $Cs_2CO_3$, in an organic solvent, such as dioxane.

The compound of Formula (III) may be obtained by reducing a compound of Formula (IV):

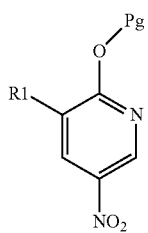
(IV)

Where R1 is defined as in Formula (I) and Pg is defined as in Formula (II). Reduction may be achieved by reacting the compound of Formula (IV) with Fe, such as Fe powder in the presence of ammonium chloride.

The compound of Formula (IV) may be obtained by reacting a compound of Formula (V):

(V)

Where Pg is defined as in Formula (II), with a compound of Formula (B):

(B)

Or a suitable corresponding boronic acid ester such as boronic acid pinacol ester.

Typically, the reaction is a carbon-carbon coupling, such as the Suzuki coupling. It may be conducted in the presence of $PdCl_2(PPh_3)_2$, in the presence of aqueous $Na_2CO_3$, in an organic solvent such as dioxane.

According to a second route, the compound of Formula (II) may be obtained by reacting a compound of Formula (III'):

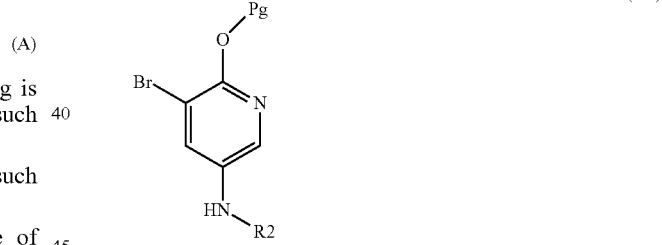
(III')

Where R2 is defined as in Formula (I) and Pg is defined as in Formula (II), With a compound of Formula (B) as defined above.

Typically, the reaction is a carbon-carbon coupling, such as the Suzuki coupling. It may be conducted in the presence of $PdCl_2(PPh_3)_2$, in the presence of aqueous $Na_2CO_3$, in an organic solvent such as dioxane.

The compound of Formula (III') may be obtained by reacting a compound of Formula (IV'):

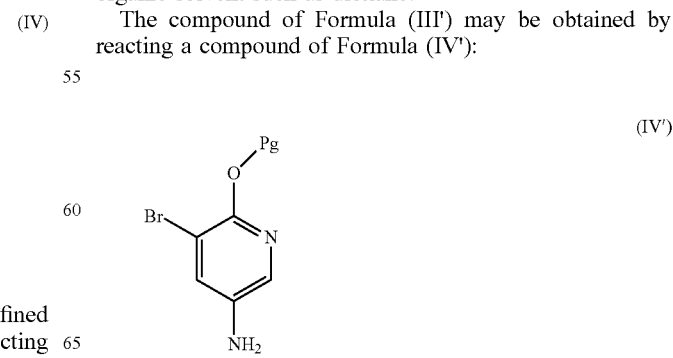
(IV')

With a compound of Formula (A):

Where R2 is defined as in Formula (I), Hal is defined as in Formula (A), and Pg is defined as in Formula (II).

Typically, the reaction is a carbon-nitrogen coupling, such as the Buchwald-Hartwig coupling. It may be conducted in the presence of Pd(OAc)$_2$, 4,5-Bis(diphenylphosphino)-9,9-dimethylxanthene (Xantphos), Cs$_2$CO$_3$, in an organic solvent, such as dioxane.

Generally, the products of Formula (V), (IV'), (A), (B) and the reagents described above are commercially available or can be easily prepared, by application of routine synthesis, such as disclosed by Larock (supra).

According to another object, the present invention also concerns a pharmaceutical composition comprising a compound of Formula (I) according to the invention as defined above, together with at least one pharmaceutically acceptable excipient.

According to a further object, the present invention concerns a compound of Formula (I) as defined above for its use in the prevention and/or treatment of pain, such as MA.

Pain as used herein refers to inflammatory pain, neuropathic pain, cancer pain, visceral pain, headache, migraine, spontaneous pain.

It has been found that the compounds of the invention are effective to prevent or to treat pain. Further, it has been found that they may be highly effective in the treatment of MA for which analgesics are not always effective.

According to an embodiment, the present invention also concerns the use of a compound of Formula (I) according to the invention for the preparation of a medicament for treating and/or preventing pain.

According to a further embodiment, the present invention also concerns a method of treatment and/or prevention of pain comprising the administration of a therapeutically effective amount of a compound of Formula (I) according to the invention as defined above to a patient in the need thereof.

As used herein, the term "patient" refers to a warm-blooded animal such as a mammal, preferably a human or a human child, which is afflicted with, or has the potential to be afflicted with one or more diseases and conditions described herein.

As used herein, a "therapeutically effective amount" refers to an amount of a compound of the present invention which is effective in reducing, eliminating, treating or controlling the symptoms of the herein-described diseases and conditions. The term "controlling" is intended to refer to all processes wherein there may be a slowing, interrupting, arresting, or stopping of the progression of the diseases and conditions described herein, but does not necessarily indicate a total elimination of all disease and condition symptoms, and is intended to include prophylactic treatment and chronic use.

As used herein, the expression "pharmaceutically acceptable" refers to those compounds, materials, compositions, or dosage forms which are within the scope of sound medical judgment, suitable for contact with the tissues of human beings and animals without excessive toxicity, irritation, allergic response, or other problem complications commensurate with a reasonable benefit/risk ratio.

The dosage of drug to be administered depends on such variables as the type and extent of progression of the disease or disorder, the overall health status of the particular patient, the relative biological efficacy of the compound selected, and Formulation of the compound, excipients, and its route of administration.

The compounds of present invention may be formulated into a pharmaceutically acceptable preparation, on admixing with a carrier, excipient or a diluent, in particular for oral or parenteral use. Oral preparations may be in the form of tablets or capsules. A solid carrier can include one or more substances which may also act as flavoring agents, lubricants, solubilizers, suspending agents, fillers, glidants, compression aids, binders or tablet-disintegrating agents; it can also be an encapsulating material. Liquid carriers can include water, an organic solvent, a mixture of both or pharmaceutically acceptable oils and fats. The compositions may conveniently be administered in unit dosage form and may be prepared by any of the methods well known in the pharmaceutical art, for example, as described in Remington: The Science and Practice of Pharmacy, 20th ed.; Gennaro, A. R., Ed.; Lippincott Williams & Wilkins: Philadelphia, PA, 2000. Pharmaceutically compatible binding agents and/or adjuvant materials can be included as part of the composition.

The tablets, pills, powders, capsules, troches and the like can contain one or more of any of the following ingredients, or compounds of a similar nature: a binder such as microcrystalline cellulose, or gum tragacanth; a diluent such as starch or lactose; a disintegrant such as starch and cellulose derivatives; a lubricant such as magnesium stearate; a glidant such as colloidal silicon dioxide; a sweetening agent such as sucrose or saccharin; or a flavoring agent such as peppermint, or methyl salicylate. Preferred tablets contain lactose, cornstarch, magnesium silicate, croscarmellose sodium, povidone, magnesium stearate, or talc in any combination. Capsules can be in the form of a hard capsule or soft capsule, which are generally made from gelatin blends optionally blended with plasticizers, as well as a starch capsule. In addition, dosage unit forms can contain various other materials that modify the physical form of the dosage unit, for example, coatings of sugar, shellac, or enteric agents. Other oral dosage forms syrup or elixir may contain sweetening agents, preservatives, dyes, colorings, and flavorings. In addition, the active compounds may be incorporated into fast dissolve, modified-release or sustained-release preparations and Formulations, and wherein such sustained-release Formulations are preferably bi-modal.

Liquid preparations for administration include sterile aqueous or non-aqueous solutions, suspensions, and emulsions. The liquid compositions may also include binders, buffers, preservatives, chelating agents, sweetening, flavoring and coloring agents, and the like. Non-aqueous solvents include alcohols, propylene glycol, polyethylene glycol, acrylate copolymers, vegetable oils such as olive oil, and organic esters such as ethyl oleate. Aqueous carriers include mixtures of alcohols and water, hydrogels, buffered media, and saline. In particular, biocompatible, biodegradable lactide polymer, lactide/glycolide copolymer, or polyoxyethylene-polyoxypropylene copolymers may be useful excipients to control the release of the active compounds. Intravenous vehicles can include fluid and nutrient replenishers, electrolyte replenishers, such as those based on Ringer's dextrose, and the like. Other potentially useful parenteral delivery systems for these active compounds include ethylene-vinyl acetate copolymer particles, osmotic pumps, implantable infusion systems, and liposomes.

Other features of the invention will become apparent in the course of the following description of exemplary embodiments that are given for illustration of the invention and not intended to be limiting thereof.

Figure 2:
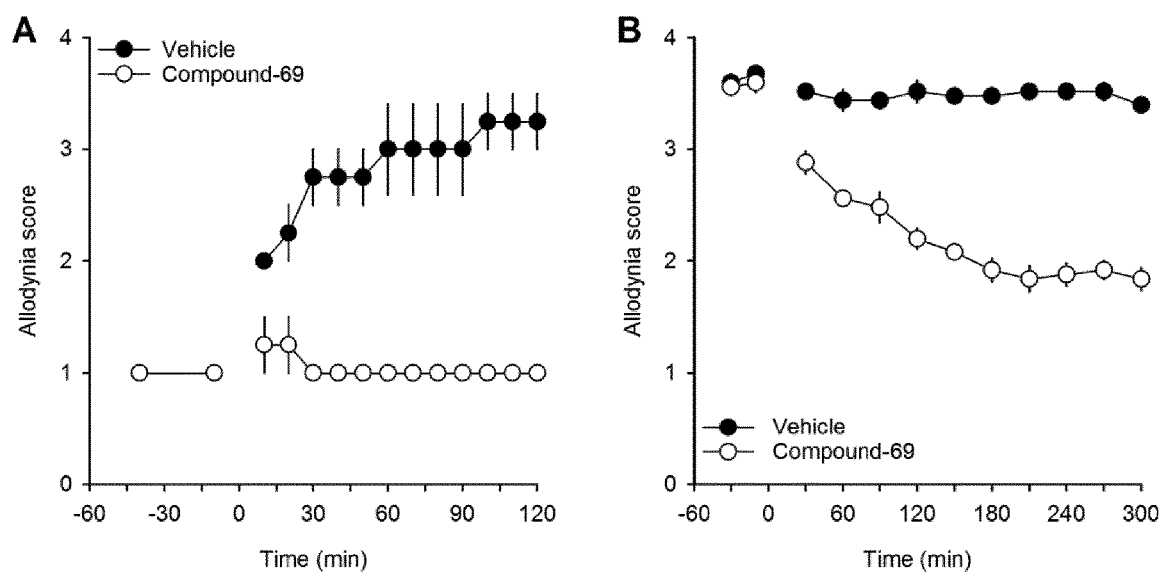

FIG. 2 shows that the intracisternal application of compound 69 both prevents inflammatory (A) and reverses neuropathic MA (B). Time courses of changes in behavioral responses (allodynic score) evoked by normally innocuous mechanical stimuli (6-g von Frey filament) applied on the face of rats intracisternally treated with compound 69 (5 μL at 100 μM) or vehicle. In A, compound 69 or vehicle was preemptively applied 30 min before subcutaneous injection of CFA (at time 0). In B, compound 69 or vehicle was applied (at time 0) 14 days after IoN-CCI; that is, once a stable MA was established. MA was completely suppressed (A) or quickly reversed (B) in compound 69-treated rats. Results are presented as mean±s.e.m.; n=4 (A) and n=5 (B) in each group. Allodynic score (from 0 to 4) according to Vos et al. *J. Neurosci.* 1994, 14, 2708-2723.

Figure 3:
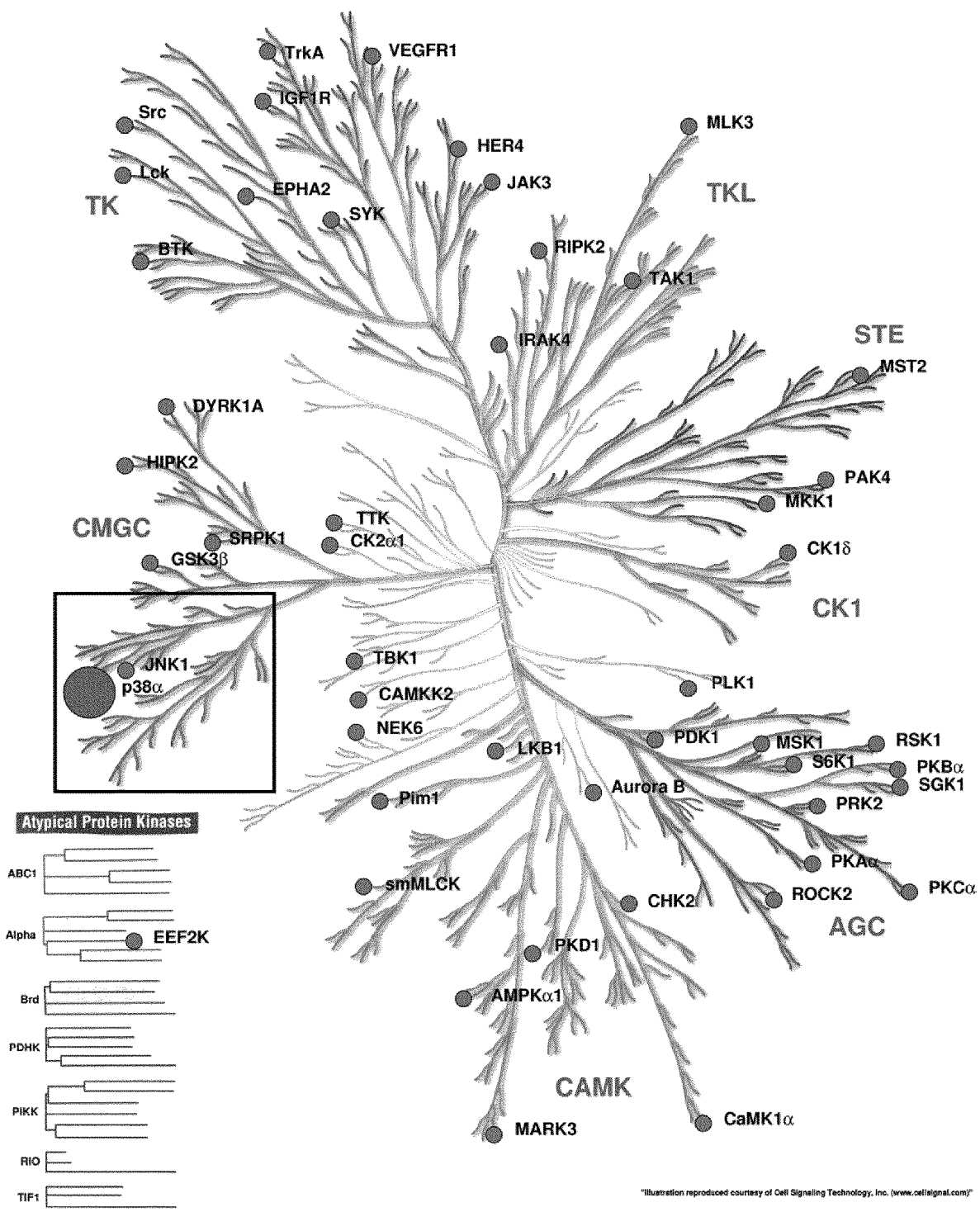
Figure 4:
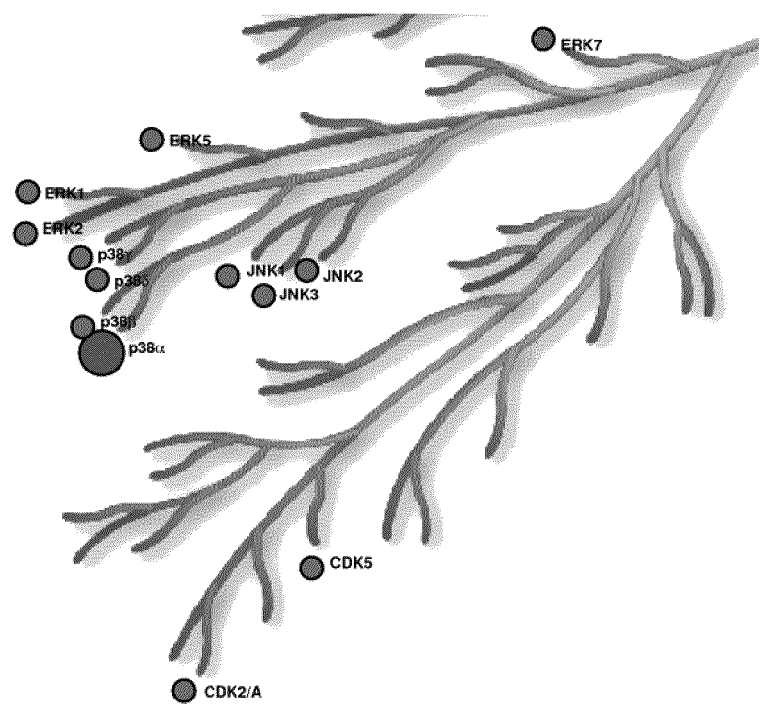
Figure 4:
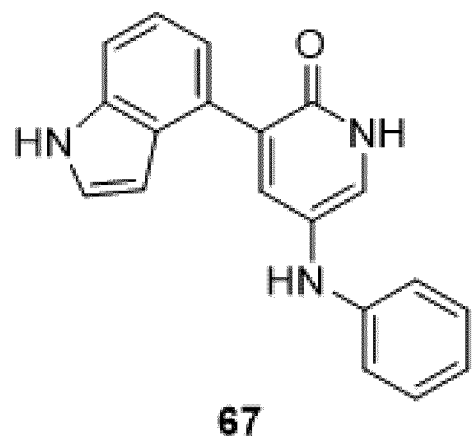
Figure 4:
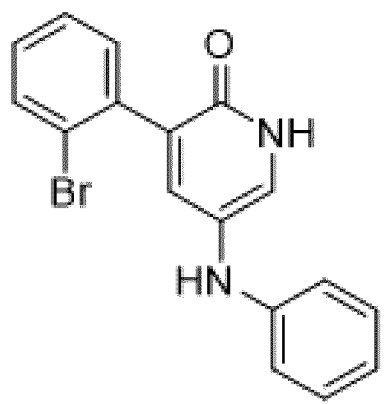

FIG. 3 illustrates the human kinome. Compound 69 was evaluated at the International Center For Kinase Profiling (ICKP, Dundee, Scotland) toward a panel of 50 protein kinases that provide a representative sampling of the human kinome. The results were expressed as the mean percentage of residual activity at 10 μM concentration (duplicate assays). Small disks: ≥65%, larger disk: 19%. See Table 3 for screening values. The black square indicates the kinome region containing protein kinases evaluated in a second screening (FIG. 4, Table 4). The tree was generated using the Kinome Render software, and the illustration reproduced courtesy of Cell Signaling Technology, Inc. (www.cellsignal.com) Chartier et al *PeerJ* 2013, 1:e126.

FIG. 4 illustrates the studies carried out for compounds 67 and 69. Compounds 67 and 69 (FIG. 4B) were evaluated at the International Center For Kinase Profiling (ICKP, Dundee, Scotland) toward a panel of 13 protein kinases. The results (FIG. 4A) were expressed as the mean percentage of residual activity at 1 μM concentration (duplicate assays). Small disks: ≥90%, larger disk: 59%, for both compounds. See Table 4 for screening values. The tree was generated using the Kinome Render software, and the illustration reproduced courtesy of Cell Signaling Technology, Inc. (www.cellsignal.com) Chartier et al *PeerJ* 2013, 1:e126.

Figure 5:
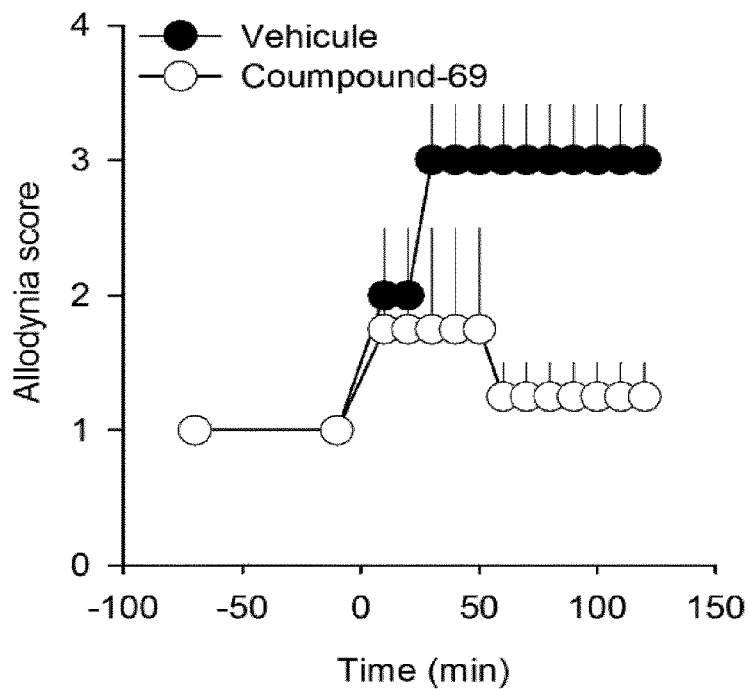
Figure 5:
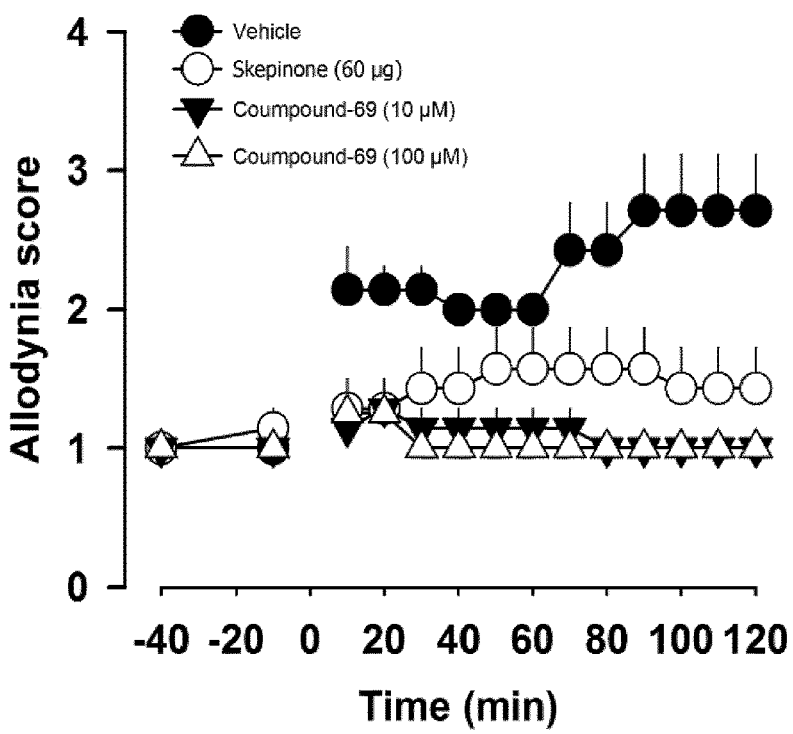

FIG. 5 illustrates the allodynia score for compound 69 over time, compared with control (FIGS. 5A and 5B) and over skepinone (FIG. 5B).

EXAMPLES

1. Synthesis of 3,5-disubstituted pyridin-2(1H)-one derivatives

General

Starting materials were obtained from commercial suppliers and used without further purification. IR spectra were recorded on a Perkin-Elmer Spectrum 65 FT-IR spectrometer ($\bar{v}$ in cm$^{-1}$). NMR spectra, performed on a Bruker AVANCE 400 III HD ($^1$H: 400 MHz, $^{13}$C: 101 MHz) are reported in ppm using the solvent residual peak as an internal standard; the following abbreviations are used: singlet (s), doublet (d), triplet (t), quadruplet (q), doublet of doublets (dd), doublet of doublet of doublets (ddd), doublet of triplets (dt), triplet of doublets (td), triplet of triplets (tt), multiplet (m), broad signal (br s). Coupling constants are expressed in Hertz. Experiments under microwave irradiation were performed using a CEM Discover Benchmate apparatus. High resolution mass spectra were determined on a high-resolution Waters Micro Q-Tof or Thermo Scientific Q Exactive Q-Orbitrap apparatus (UCA START, Université Clermont Auvergne, Clermont-Ferrand, France). Chromatographic purifications were performed by column chromatography using 40-63 μm silica gel. Reactions were monitored by TLC using fluorescent silica gel plates (60 F254 from Macherey Nagel). Melting points were measured on a Stuart SMP3 apparatus and are uncorrected.

The purity of compounds 19-25 and 66-82 was established by HPLC analysis using a Agilent infinity 1260 chromatograph with DAD detector and an Agilent Zorbax SB-Phenyl column (4.6 mm×150 mm, 3.5 μm). Flow rate was 0.8 mL/min and the analysis was performed at 25° C. Detection wavelength is indicated for each compound. Solvents were (A) water/0.1% formic acid, (B) Acetonitrile. Gradient was 100:0 A/B to 30:70 A/B in 8 min and then 30:70 A/B for 3 min.

Abbreviations Used

CFA, complete Freund's adjuvant; ERK, Extracellular signal-regulated kinases; IoN-CCI, chronic constriction injury of the rat's infraorbital nerve; MA, mechanical allodynia; MDH, medullary dorsal horn; p38 MAPK, p38 mitogen-activated protein kinases; PDB, protein data bank; PK, protein kinases; PKC, protein kinase C; SDH, spinal dorsal horn.

An initial series of compounds was synthesized as depicted in Scheme 1:

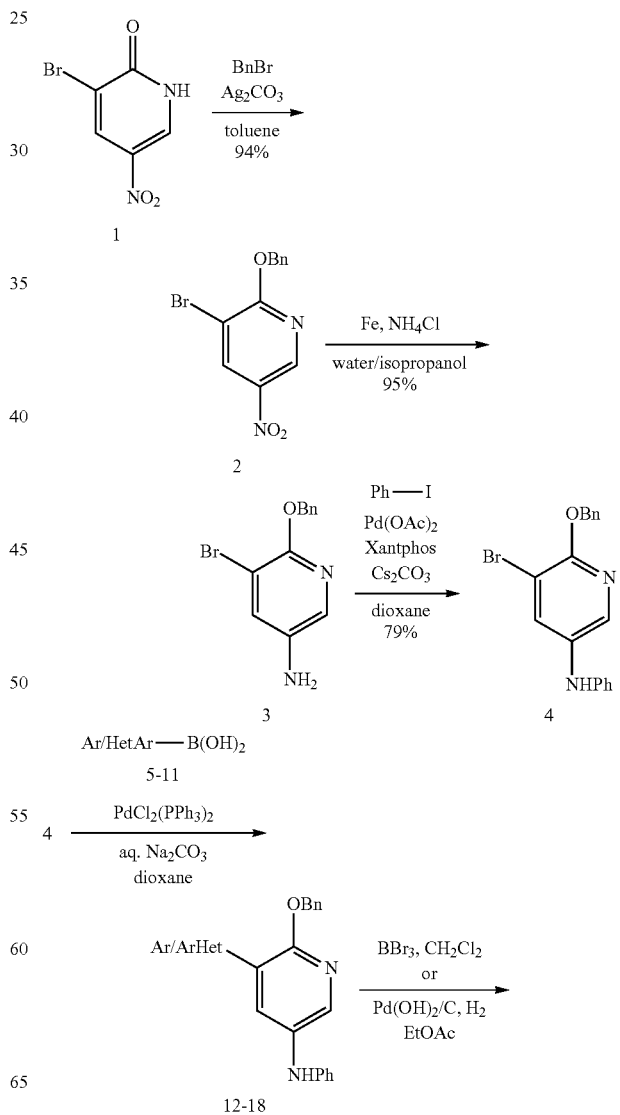

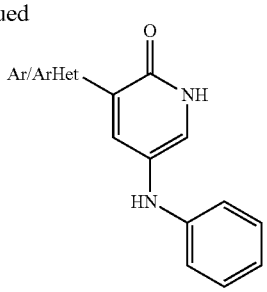

19-25

The synthesis started from commercially available 3-bromo-5-nitropyridin-2(1H-1)-one 1, functionalized in such way that desired substituents could be easily introduced at the 3- and 5-positions. First, compound 1 was regioselectively O-benzylated in the presence of benzyl bromide and silver carbonate leading to pyridine 2 (WO2009/021696). After reduction of the nitro group, Buchwald-Hartwig amination with iodobenzene afforded compound 4 with good yield. From intermediate 4, aryl and heteroaryl substituents were then introduced at the 3-position using a Suzuki cross-coupling with the boronic acids 5-11 (Scheme 1, Table 1) leading to intermediates 12-18. Finally, cleavage of the benzyl group using $BBr_3$ yielded final compounds 19-25 (Table 1).

TABLE 1

Isolated yields for compounds 12-25.

| Boronic acids[a] | | Products 12-18 | | | Products 19-25 | | |
|---|---|---|---|---|---|---|---|
| Cpd | Ar/HetAr | Cpd | Ar/HetAr | % yield | Cpd | Ar/HetAr | % yield |
| 5 | Phenyl | 12 | Phenyl | 94 | 19 | Phenyl | 90 |
| 6 | 4-Fluorophenyl | 13 | 4-Fluorophenyl | 95 | 20 | 4-Fluorophenyl | 97 |
| 7 | Pyridine-4-yl | 14 | Pyridin-4-yl | 93 | 21 | Pyridin-4-yl | 80 |
| 8 | 1-TIPS-1H-indole-3-yl | 15 | 1H-Indolyl-3-yl | 88 | 22 | 1H-Indolyl-3-yl | 73 |
| 9 | Quinolin-8-yl | 16 | Quinolin-8-yl | 83 | 23 | Quinolin-8-yl | 19 |
| 10 | Pyrimidine-5-yl | 17 | Pyrimidin-5-yl | 94 | 24 | Pyrimidin-5-yl | 80 |
| 11 | Isoquinoline-5-yl | 18 | Isoquinolin-5-yl | 95 | 25 | Isoquinolin-5-yl | 44 |

[a]Boronic acids were either commercially available or prepared according to literature procedures (8: EP 2617724, 9: Wada et al *J. Org. Chem.* 2003, 68, 5123-5131, 11: WO2008006480).

According to a similar protocol, further compounds were prepared:

TABLE 2

Structure and isolated yield of compounds 46-85.

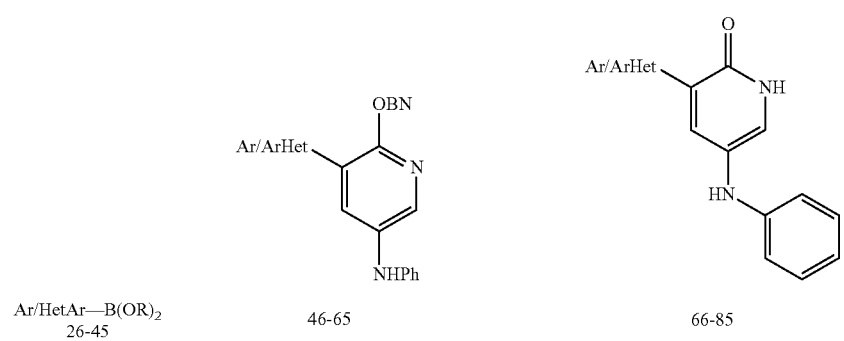

Ar/HetAr—B(OR)$_2$  46-65    66-85
26-45

| Boronic acids/boronate[a,b] | | Products 46-65 | | | Products 66-85 | | |
|---|---|---|---|---|---|---|---|
| Cpd | Ar/HetAr | Cpd | Ar/HetAr | % yield | Cpd | Ar/HetAr | % yield |
| 26 | Quinolin-4-yl | 46 | Quinolin-4-yl | 90 | 66 | Quinolin-4-yl | 69 |
| 27 | 1H-Indol-4-yl[b] | 47 | 1H-Indol-4-yl | quant. | 67 | 1H-Indol-4-yl | 67 |
| 28 | 2-Cl—C$_6$H$_4$ | 48 | 2-Cl—C$_6$H$_4$ | 85 | 68 | 2-Cl—C$_6$H$_4$ | 50 |
| 29 | 2-Br—C$_6$H$_4$ | 49 | 2-Br—C$_6$H$_4$ | —[c] | 69 | 2-Br—C$_6$H$_4$ | 18[d] |
| 30 | 2-(CO$_2$Et)C$_6$H$_4$ | 50 | 2-(CO$_2$Et)C$_6$H$_4$ | 75 | 70 | 2-(CO$_2$Et)C$_6$H$_4$ | 78 |
| 31 | 2-CNC$_6$H$_4$ | 51 | 2-CNC$_6$H$_4$ | —[c] | 71 | 2-(CONH$_2$)C$_6$H$_4$ | 32[d] |
| 32 | 2-NO$_2$—C$_6$H$_4$ | 52 | 2-NO$_2$—C$_6$H$_4$ | 37 | 72 | 2-NO$_2$—C$_6$H$_4$ | 89 |
| 33 | (1,1'-biphenyl)-4-yl | 53 | (1,1'-biphenyl)-4-yl | 91 | 73 | (1,1'-biphenyl)-4-yl | 80 |
| 34 | 3-Cl—C$_6$H$_4$ | 54 | 3-Cl—C$_6$H$_4$ | 95 | 74 | 3-Cl—C$_6$H$_4$ | 92 |
| 35 | 3-AcetylC$_6$H$_4$ | 55 | 3-AcetylC$_6$H$_4$ | quant. | 75 | 3-AcetylC$_6$H$_4$ | 70[e] |
| 36 | 4-HOC$_6$H$_4$ | 56 | 4-HOC$_6$H$_4$ | 75 | 76 | 4-HOC$_6$H$_4$ | 91 |
| 37 | 4-CH$_3$C$_6$H$_4$ | 57 | 4-CH$_3$C$_6$H$_4$ | 86 | 77 | 4-CH$_3$C$_6$H$_4$ | 96 |
| 38 | 4-CF$_3$C$_6$H$_4$ | 58 | 4-CF$_3$C$_6$H$_4$ | 83 | 78 | 4-CF$_3$C$_6$H$_4$ | 95 |
| 39 | 4-CF$_3$OC$_6$H$_4$ | 59 | 4-CF$_3$OC$_6$H$_4$ | 91 | 79 | 4-CF$_3$OC$_6$H$_4$ | 91 |

TABLE 2-continued

Structure and isolated yield of compounds 46-85.

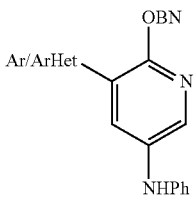

Ar/HetAr—B(OR)$_2$
26-45

46-65

66-85

| | Boronic acids/boronate[a,b] | | Products 46-65 | | | Products 66-85 | |
|---|---|---|---|---|---|---|---|
| Cpd | Ar/HetAr | Cpd | Ar/HetAr | % yield | Cpd | Ar/HetAr | % yield |
| 40 | 4-(CO$_2$Me)C$_6$H$_4$ | 60 | 4-(CO$_2$Me)C$_6$H$_4$ | 60 | 80 | 4-(CO$_2$Me)C$_6$H$_4$ | 90 |
| 41 | 4-(CONH$_2$)C$_6$H$_4$ | 61 | 4-(CONH$_2$)C$_6$H$_4$ | —[c] | 81 | 4-(CONH$_2$)C$_6$H$_4$ | 74[d] |
| 42 | 2,4-diF—C$_6$H$_3$ | 62 | 2,4-diF—C$_6$H$_3$ | —[c] | 82 | 2,4-diF—C$_6$H$_3$ | 62[d] |
| 43 | 1H-Indol-7-yl | 63 | 1H-Indol-7-yl | 49 | 83 | 1H-Indol-7-yl | —[f] |
| 44 | 3-NH$_2$C$_6$H$_4$ | 64 | 3-NHC$_2$C$_6$H$_4$ | 96 | 84 | 3-NH$_2$C$_6$H$_4$ | —[f] |
| 45 | 3-CH$_3$OC$_6$H$_4$ | 65 | 3-CH$_3$OC$_6$H$_4$ | 86 | 85 | 3-HOC$_6$H$_4$ | —[f] |

[a]Boronic acids/boronates were commercially available except 43 which was prepared according to literature procedures Prieto et al *J. Org. Chem.* 2007, 72, 1047-1050.
[b]Compound 27 was a pinacol boronate.
[c]Compounds could not be fully purified by column chromatography and were engaged in the next step without further purification.
[d]Yield over 2 steps from 4.
[e]Compound 55 was debenzylated using TMSI.
[f]Compounds could not be purified.

2-(Benzyloxy)-3-bromo-5-nitropyridine (2)

To a solution under argon of crushed 3-bromo-5-nitropyridin-2(1H)-one 1 (1.90 g, 8.68 mmol, 1 eq.) in anhydrous toluene (26 mL), benzyl bromide (2.2 mL, 18.5 mmol, 2.1 eq.) was added. The mixture was stirred at room temperature for 5 min. Then, the mixture was stirred at 70° C. and crushed Ag$_2$CO$_3$ was added in three portions of 0.35 eq. every hour (3×840 mg, 3×3.05 mmol, 3×0.35 eq.). After 3 h 30 min at 70° C., the mixture was filtered through a pad of Celite and washed with ethyl acetate. The obtained yellow solid was purified by column chromatography (SiO$_2$, cyclohexane to EtOAc/cyclohexane 95:5) to give the desired product 2 with a residual impurity which was eliminated by washing with cyclohexane, to give 2 (2.51 g, 8.12 mmol, 94%) as a white solid.

R$_f$=0.40 (EtOAc/cyclohexane 2:98); Mp 128° C.; IR (ATR) 3075, 1593, 1571, 1518, 1435, 1337, 1318, 1050, 1008, 725 cm$^{-1}$; $^1$H NMR (400 MHz, DMSO-d$_6$) δ 9.10 (d, J=2.5, 1H), 8.85 (d, J=2.5, 1H), 7.50 (d, J=7.3, 2H), 7.45-7.34 (m, 3H), 5.57 (s, 2H); $^{13}$C NMR (101 MHz, DMSO-d$_6$) δ 162.3 (C), 142.8 (CH), 139.6 (C), 137.1 (CH), 135.7 (C), 128.50 (2CH), 128.22 (CH), 127.9 (2CH), 106.3 (C), 69.7 (CH$_2$); HRMS (ESI+) calcd for C$_{12}$H$_{10}$BrN$_2$O$_3$ (M+H)$^+$ 308.9869, found 308.9869.

6-(Benzyloxy)-5-bromopyridin-3-amine (3)

To a solution of compound 2 (5.4 g, 17.5 mmol, 1 eq.) in a 10:1 propan-2-ol/water mixture (375 mL) were added Fe powder (5.89 g, 105 mmol, 6 eq.) and NH$_4$Cl (380 mg, 7.10 mmol, 0.4 eq.). The mixture was refluxed for 4 h. Then, the mixture was filtered through a pad of Celite which was then washed with ethyl acetate. The filtrate was washed with water, and the aqueous phase was extracted with ethyl acetate. The organic phase was dried over MgSO$_4$, filtered and then evaporated. The obtained orange oil was purified by column chromatography (SiO$_2$, EtOAc/cyclohexane 3:7+0.5% NEt$_3$) to give the desired product 3 (4.64 g, 16.6 mmol, 95%) as a brown oil which crystalized in beige solid.

R$_f$=0.38 (EtOAc/cyclohexane 3:7); Mp 81° C.; IR (ATR) 3390, 3305, 3208, 1625, 1452, 1356, 1216, 1046, 982 cm$^{-1}$; $^1$H NMR (400 MHz, DMSO-d$_6$) δ 7.50 (d, J=2.5, 1H), 7.42 (d, J=7.4, 2H), 7.37 (t, J=7.4, 2H), 7.32 (d, J=2.5, 1H), 7.32-7.27 (m, 1H), 5.26 (s, 2H), 5.04 (s, 2H); $^{13}$C NMR (101 MHz, DMSO-d$_6$) δ 150.4 (C), 141.2 (C), 137.6 (C), 130.1 (CH), 128.3 (2CH), 128.2 (CH), 127.6 (CH), 127.4 (2CH), 105.8 (C), 67.3 (CH$_2$); HRMS (ESI+) calcd for C$_{12}$H$_{12}$BrN$_2$O (M+H)$^+$ 279.0128, found 279.0124.

6-(Benzyloxy)-5-bromo-N-phenylpyridin-3-amine (4)

A 5 mL screw-cap tube under argon was charged with compound 3 (444 mg, 1.59 mmol, 1 eq.), Pd(OAc)$_2$ (17.8 mg, 0.08 mmol, 0.05 eq.), Xantphos (46.2 mg, 0.08 mmol, 0.05 eq.) and Cs$_2$CO$_3$ (1.04 g, 3.19 mmol, 2 eq.). Then, anhydrous 1,4-dioxane degassed with argon (8 mL) and iodobenzene (180 µL, 1.61 mmol, 1 eq.) were added. The tube was sealed and the mixture was stirred at 100° C. for 4 h. The resulting suspension was filtered through a pad of Celite which was then washed with ethyl acetate. After evaporation of the filtrate, the brown residue was purified by column chromatography (SiO$_2$, cyclohexane to EtOAc/cyclohexane 1:9) to give a yellow-orange oil 4 (444 mg, 1.25 mmol, 79%) which solidify into a light brown solid after some days in freezer.

$R_f$=0.31 (EtOAc/cyclohexane 1:9); Mp 49° C.; IR (ATR) 3394, 1602, 1502, 1462, 1444, 1356, 1292, 1230, 1050, 738, 694 cm$^{-1}$; $^1$H NMR (400 MHz, DMSO-d$_6$) δ 8.14 (s, 1H, NH), 7.97 (d, J=2.5, 1H), 7.78 (d, J=2.5, 1H), 7.48-7.44 (m, 2H), 7.42-7.37 (m, 2H), 7.35-7.30 (m, 1H), 7.22 (dd, J=8.6, 7.4, 2H), 6.96 (dd, J=8.6, 1.1, 2H), 6.82 (tt, J=7.4, 1.1, 1H), 5.37 (s, 2H); $^{13}$C NMR (101 MHz, DMSO-d$_6$) δ 153.3 (C), 143.7 (C), 137.2 (C), 135.4 (C), 135.2 (CH), 132.7 (CH), 129.4 (2CH), 128.4 (2CH), 127.8 (CH), 127.5 (2CH), 119.8 (CH), 115.7 (2CH), 106.0 (C), 67.7 (CH$_2$); HRMS (ESI+) calcd for C$_{18}$H$_{16}$BrN$_2$O (M+H)$^+$355.0441, found 355.0440.

General Procedures for the Preparation of Compounds 12-18, 46-51, 53-65 and 102-117.

Procedure A (conventional heating): To a solution under argon of brominated derivative in 1,4-dioxane (0.1-0.6 mmol, 1 eq., 0.1 M) were added the boronic acid or boronic ester (1.5 eq.) and a 2 M Na$_2$CO$_3$ aqueous solution (5 eq.). The mixture was degassed with argon for 10 min before the addition of PdCl$_2$(PPh$_3$)$_2$ (0.05 eq.). The solution was refluxed overnight. Ethyl acetate was added and the resulting mixture was washed with water. The organic phase was dried over MgSO$_4$ and filtered. After evaporation under reduced pressure, the crude was purified by column chromatography.

Procedure B (microwave irradiation): A 10 mL microwave tube under argon was charged with brominated derivative (0.2-0.4 mmol, 1 eq.). 1,4-dioxane (0.1 M), boronic acid or boronic ester (1.5 eq.) and a 2 M Na$_2$CO$_3$ aqueous solution (5 eq.) were added. The solution was degassed with argon for 10 min before the addition of PdCl$_2$(PPh$_3$)$_2$ (0.05 eq.). The tube was sealed and the mixture was irradiated for 1 h (Discover mode, Dynamic control type, P$_{max}$=75 W, T=100° C.). The mixture was then filtered through a pad of Celite which was then washed with ethyl acetate. The organic phase was washed with water and then dried over MgSO$_4$ and filtered. After evaporation under reduced pressure, the crude was purified by column chromatography.

General Procedure for the Preparation of Compounds 19-21, 23-25, 66-74, 76-82, 118, 119 and 131.

Procedure C: To a solution under argon and cooled to 0° C. of benzylated compound in anhydrous dichloromethane (0.1-0.5 mmol, 1 eq., 0.02 M) was added dropwise a 1 M BBr$_3$ solution in dichloromethane (4 eq.). The mixture was stirred at room temperature for 1 h. The reaction mixture was then quenched by addition of methanol, or by addition of NEt$_3$ and methanol when indicated. After evaporation under reduced pressure, EtOAc was added. The mixture was washed with water, dried over MgSO$_4$, and filtered. After evaporation under reduced pressure, the crude was purified by column chromatography.

6-(Benzyloxy)-N,5-diphenylpyridin-3-amine (12)

Compound 12 was prepared according to general procedure B, starting from 4 (95 mg, 0.267 mmol). The crude oil was purified by column chromatography (SiO$_2$, cyclohexane to EtOAc/cyclohexane 1:9) to give 12 (89 mg, 0.253 mmol, 94%).

$R_f$=0.70 (EtOAc/cyclohexane 3:7); Mp 118° C.; IR (ATR) 3380, 1601, 1514, 1497, 1466, 1424, 1359, 1298, 1255, 1218, 1022, 753, 728, 657, 695 cm$^{-1}$; $^1$H NMR (400 MHz, DMSO-d$_6$) δ 8.07 (s, 1H), 7.99 (d, J=2.7, 1H), 7.62-7.59 (m, 2H), 7.53 (d, J=2.8, 1H), 7.46-7.32 (m, 7H), 7.31-7.26 (m, 1H), 7.20 (t, J=7.8, 2H), 6.98 (d, J=8.0, 2H), 6.77 (t, J=7.3, 1H), 5.37 (s, 2H); $^{13}$C NMR (101 MHz, DMSO-d$_6$) δ 154.3 (C), 144.4 (C), 137.7 (C), 136.1 (C), 135.7 (CH), 134.6 (C), 130.5 (CH), 129.3 (2CH), 129.0 (2CH), 128.32 (2CH), 128.27 (2CH), 127.6 (CH), 127.5 (CH), 127.4 (2CH), 123.8 (C), 119.1 (CH), 115.2 (2CH), 67.1 (CH$_2$); HRMS (ESI+) calcd for C$_{24}$H$_{21}$N$_2$O (M+H)$^+$353.1648, found 353.1641.

6-(Benzyloxy)-5-(4-fluorophenyl)-N-phenylpyridin-3-amine (13)

Compound 13 was prepared according to general procedure A, starting from 4 (154 mg, 0.434 mmol) and the corresponding boronic acid. The mixture was refluxed for 18 h. The crude oil was purified by column chromatography (SiO$_2$, cyclohexane+0.5% NEt$_3$ to EtOAc/cyclohexane 1:9+ 0.5% NEt$_3$) to give 13 (152 mg, 0.410 mmol, 95%) as a beige solid.

$R_f$=0.70 (EtOAc/cyclohexane 3:7); Mp 104° C.; IR (ATR) 3383, 1599, 1500, 1438, 1223, 843, 757, 734, 697 cm$^{-1}$; $^1$H NMR (400 MHz, DMSO-d$_6$) δ 8.07 (s, 1H), 7.99 (d, J=2.7, 1H), 7.68-7.62 (m, 2H), 7.53 (d, J=2.7, 1H), 7.42-7.17 (m, 9H), 6.98 (d, J=7.9, 2H), 6.77 (t, J=7.3, 1H), 5.37 (s, 2H); $^{13}$C NMR (101 MHz, DMSO-d$_6$) δ 161.6 (d, J$_{CF}$=245, C), 154.2 (C), 144.3 (C), 137.6 (C), 135.7 (CH), 134.6 (C), 132.4 (d, J$_{CF}$=3, C), 131.0 (d, J$_{CF}$=8, 2CH), 130.4 (CH), 129.3 (2CH), 128.3 (2CH), 127.5 (CH), 127.4 (2CH), 122.8 (C), 119.1 (CH), 115.2 (2CH), 115.1 (d, J$_{CF}$=21.5, 2CH), 67.1 (CH$_2$); HRMS (ESI+) calcd for C$_{24}$H$_{20}$FN$_2$O (M+H)$^+$ 371.1554, found 371.1562.

2-(Benzyloxy)-N-phenyl-[3,4'-bipyridin]-5-amine (14)

Compound 14 was prepared according to general procedure B, starting from 4 (103 mg, 0.290 mmol) and the corresponding boronic acid. The mixture was irradiated for 45 min at 100° C. The crude product was purified as above to give 14 (95.7 mg, 0.271 mmol, 93%). $R_f$=0.30 (EtOAc/cyclohexane 5:5); Mp 129° C.; IR (ATR) 3261, 3189, 1594, 1443, 1262, 1229, 996, 829, 748, 698 cm$^{-1}$; $^1$H NMR (400 MHz, DMSO-d$_6$) δ 8.63-8.60 (m, 2H), 8.14 (s, 1H), 8.06 (d, J=2.8, 1 H), 7.66-7.63 (m, 3H), 7.43-7.40 (m, 2H), 7.39-7.34 (m, 2H), 7.32-7.27 (m, 1H), 7.21 (dd, J=8.5, 7.4, 2H), 6.99 (dd, J=8.6, 1.0, 2H), 6.79 (t, J=7.3, 1H), 5.40 (s, 2H); $^{13}$C NMR (101 MHz, DMSO-d$_6$) δ 154.2 (C), 149.6 (2CH), 144.2 (C), 143.7 (C), 137.4 (C) 137.1 (CH), 134.7 (C), 130.3 (CH), 129.4 (2CH), 128.4 (2CH), 127.6 (CH), 127.5 (2CH), 123.7 (2CH), 121.0 (C), 119.3 (CH), 115.3 (2CH), 67.3 (CH$_2$); HRMS (ESI+) calcd for C$_{23}$H$_{20}$N$_3$O (M+H)$^+$ 354.1601, found 354.1602.

6-(Benzyloxy)-5-(1H-indol-3-yl)-N-phenylpyridin-3-amine (15)

1-(Triisopropylsilyl)-1H-indol-3-yl)boronic acid was prepared from 3-bromo-1-(triisopropylsilyl)-1H-indole according to literature procedure (EP 2617724). A solution under argon of 3-bromo-1-(triisopropylsilyl)-1H-indole (500 mg, 1.42 mmol, 1 eq.) in anhydrous THF (5 mL) was cooled to −60° C. A 2.42 M n-butyllithium solution in hexane (0.73 mL, 1.77 mmol, 1.25 eq.) was added dropwise. The mixture was stirred at −60° C. for 1 h. Triisopropyl borate (0.4 mL, 1.73 mmol, 1.22 eq.) was added dropwise and the mixture was stirred at −60° C. for 1 h and at room temperature for 20 h. A saturated aqueous NH$_4$Cl solution (1.5 mL) and toluene (1.5 mL) were added and the mixture was washed with water. The organic phase was dried over MgSO$_4$, filtered and evaporated giving 1:1 mixture of 1-(triisopropylsilyl)-1H-indol-3-yl)boronic acid and 1-(triisopropylsilyl)-1H-indole (427 mg, ratio evaluated by $^1$H NMR). The crude was used without purification. Compound 15 was prepared according to general procedure A, starting from 4 (47.8 mg, 0.135 mmol) and the mixture of 1-(triisopropylsilyl)-1H-indol-3-yl)boronic acid and 1-(triisopropylsilyl)-1H-indole (128 mg). The reaction mixture was refluxed for 18 h. The obtained crude (170 mg) was directly engaged in the next step due to partial deprotection of the indolic part. To a solution of the crude product in THF (1 mL) was added a tetra-n-butylammonium fluoride solution in THF (1 M, 0.36 mL, 0.36 mmol, 2.7 eq.). The mixture was stirred for 1 h 30 min. EtOAc was added and the solution was washed with water and brine. The organic phase was dried over $MgSO_4$ and filtered. After evaporation, the solid was purified by column chromatography ($SiO_2$, cyclohexane+0.5% $NEt_3$ to EtOAc/cyclohexane 25:75+0.5% $NEt_3$) to give 15 (46.4 mg, 0.119 mmol, 88%) as a mauve solid.

$R_f$=0.31 (EtOAc/cyclohexane 2:8); Mp 85° C.; IR (ATR) 3388, 3308, 1593, 1441, 1234, 1019, 740, 733, 693 $cm^{-1}$; $^1$H NMR (400 MHz, DMSO-$d_6$) δ 11.42 (br s, 1H), 8.06 (s, 1H), 7.90 (d, J=2.7, 1H), 7.84 (d, J=2.7, 1H), 7.78-7.74 (m, 2H), 7.47 (d, J=7.4, 2H), 7.44 (d, J=8.4, 1H), 7.39-7.34 (m, 2H), 7.33-7.28 (m, 1H), 7.22 (t, J=7.8, 2H), 7.14 (t, J=7.4, 1H), 7.06 (t, J=7.5, 1H), 7.01 (d, J=7.9, 2H), 6.77 (t, J=7.3, 1H), 5.42 (s, 2H); $^{13}$C NMR (101 MHz, DMSO-$d_6$) δ 154.3 (C), 144.7 (C), 137.8 (C), 136.2 (C), 134.1 (C), 132.8 (CH), 129.3 (2CH), 128.8 (CH), 128.4 (2CH), 127.8 (2CH), 127.6 (CH), 126.4 (CH), 125.5 (C), 121.5 (CH), 119.6 (CH), 119.2 (CH), 118.91 (C), 118.89 (CH), 115.1 (2CH), 112.0 (CH), 109.1 (C), 67.2 ($CH_2$); HRMS (ESI+) calcd for $C_{26}H_{22}N_3O$ (M+H)$^+$392.1757, found 392.1765.

6-(Benzyloxy)-N-phenyl-5-(quinolin-8-yl)pyridin-3-amine (16)

Quinolin-8-ylboronic acid was prepared from 8-iodoquinoline according to literature procedure (Wada et al *J. Org. Chem.* 2003, 68, 5123-5131). To a solution under argon of 8-iodoquinoline (434 mg, 1.70 mmol, 1 eq.) in anhydrous THF (1.35 mL) was added N,N,N',N'-tetramethylethylenediamine (0.26 mL, 1.73 mmol, 1 eq.). The mixture was cooled to −78° C. a 2.5 M n-butyllithium solution in hexane (0.68 mL, 1.70 mmol, 1 eq.) was added dropwise. The mixture was stirred at −78° C. for 4 h. Trimethyl borate (0.57 mL, 5.11 mmol, 3 eq.) was added dropwise and the mixture was stirred at room temperature for 2 h. A 3 M aqueous HCl solution (4 mL) was added and the aqueous layer was washed with diethyl ether and neutralized by solid $NaHCO_3$. The resulting precipitate was filtered and washed with acetone to give quinolin-8-ylboronic acid (112 mg) which was used without further purification.

Compound 16 was prepared according to general procedure A, starting from 4 (145 mg, 0.408 mmol) and the quinolin-8-ylboronic acid (114 mg). The mixture was refluxed for 21 h. The crude solid was purified by column chromatography ($SiO_2$, cyclohexane+0.5% $NEt_3$ to EtOAc/cyclohexane 3:7+0.5% $NEt_3$) to give 16 (137 mg, 0.340 mmol, 83%) as a yellow solid.

$R_f$=0.41 (EtOAc/cyclohexane 3:7); Mp 162° C.; IR (ATR) 3252, 3180, 1592, 1497, 1461, 1228, 1003, 796, 736, 694 $cm^{-1}$; $^1$H NMR (400 MHz, DMSO-$d_6$) δ 8.90 (dd, J=4.1, 1.8, 1H), 8.42 (dd, J=8.3, 1.8, 1H), 8.05 (s, 1H), 8.03-8.00 (m, 2H), 7.81 (dd, J=7.1, 1.5, 1H), 7.67 (dd, J=8.1, 7.2, 1H), 7.56 (dd, J=8.3, 4.1, 1H), 7.56 (d, J=2.7, 1H), 7.24-7.12 (m, 7H), 7.01 (dd, J=8.6, 1.0, 2H), 6.74 (tt, J=7.3, 1.1, 1H), 5.27 (s, 2H); $^{13}$C NMR (101 MHz, DMSO-$d_6$) δ 155.3 (C), 150.2 (CH), 145.7 (C), 144.6 (C), 137.8 (C), 136.3 (CH), 135.8 (CH), 135.4 (C), 133.6 (C), 132.6 (CH), 130.6 (CH), 129.2 (2CH), 128.3 (CH), 128.0 (2CH+C), 127.1 (CH), 126.9 (2CH), 126.1 (CH), 122.7 (C), 121.4 (CH), 118.8 (CH), 114.9 (2CH), 66.59 ($CH_2$); HRMS (ESI+) calcd for $C_{27}H_{22}N_3O$ (M+H)$^+$404.1757, found 404.1755.

6-(Benzyloxy)-N-phenyl-5-(pyrimidin-5-yl)pyridin-3-amine (17)

Compound 17 was prepared according to general procedure A, starting from 4 (122 mg, 0.343 mmol) and the corresponding boronic acid. The mixture was refluxed for 18 h. The crude oil was purified by column chromatography ($SiO_2$, EtOAc/cyclohexane 1:9 to 65:35) to give 17 (115 mg, 0.324 mmol, 94%) as a yellow solid.

$R_f$=0.20 (EtOAc/cyclohexane 3:7); Mp 115° C.; IR (ATR) 3299, 1595, 1536, 1408, 1261, 1228, 1015, 747, 722, 692 $cm^{-1}$; $^1$H NMR (400 MHz, DMSO-$d_6$) δ 9.15 (s, 1H), 9.05 (s, 2H), 8.17 (s, 1H), 8.07 (d, J=2.7, 1H), 7.75 (d, J=2.8, 1H), 7.43-7.40 (m, 2H), 7.39-7.34 (m, 2H), 7.33-7.28 (m, 1H), 7.21 (t, J=7.8, 2H), 7.01 (d, J=7.9, 2H), 6.79 (t, J=7.3, 1H), 5.38 (s, 2H); $^{13}$C NMR (101 MHz, DMSO-$d_6$) δ 157.2 (CH), 156.5 (2CH), 154.3 (C), 144.2 (C), 137.3 (CH), 137.2 (C), 134.8 (C), 130.3 (CH), 130.0 (C), 129.3 (2CH), 128.4 (2CH), 127.68 (CH), 127.65 (2CH), 119.2 (CH), 117.2 (C), 115.3 (2CH), 67.5 ($CH_2$); HRMS (ESI+) calcd for $C_{22}H_{19}N_4O$ (M+H)$^+$355.1553, found 355.1560.

6-(Benzyloxy)-5-(isoquinolin-5-yl)-N-phenylpyridin-3-amine (18)

Isoquinolin-5-ylboronic acid was prepared from 5-bromoisoquinoline according to literature procedure (WO2008006480). Anhydrous THF (19 mL) was cooled to −78° C. then a 2.5 M n-butyllithium solution in hexane (1.2 mL, 3.0 mmol, 1.25 eq.) was added under argon. A solution of 5-bromoisoquinoline (502 mg, 2.41 mmol, 1 eq.) in anhydrous THF (5 mL) was added. The mixture was stirred at −78° C. for 1 h. Triisopropyl borate (0.70 mL, 3.0 mmol, 1.25 eq.) was added dropwise and the mixture was stirred at room temperature for 2 h. A 5% aqueous NaOH solution (1 mL) was slowly added to quench the reaction. Aqueous phase was acidified to pH 5 at 0° C. with a 10% aqueous HCl solution, then was extracted with EtOAc. The organic phase was dried over $MgSO_4$ and filtered. After evaporation, the obtained solid was washed with diethyl ether to give isoquinolin-5-ylboronic acid (135.5 mg, 0.783 mmol, 32%).

Compound 18 was prepared according to general procedure A, starting from 4 (161 mg, 0.453 mmol) and isoquinolin-5-ylboronic acid. The mixture was refluxed for 18 h. The crude solid was purified by column chromatography ($SiO_2$, EtOAc/cyclohexane 1:9 to 65:35) to give 18 (173 mg, 0.429 mmol, 95%) as a white solid.

$R_f$=0.22 (EtOAc/cyclohexane 3:7); Mp 162° C.; IR (ATR) 3279, 1603, 1441, 1361, 1227, 995, 746 $cm^{-1}$; $^1$H NMR (400 MHz, DMSO-$d_6$) δ 9.37 (s, 1H), 8.46 (d, J=5.9, 1H), 8.16 (dd, J=7.5, 1.9, 1H), 8.14 (d, J=2.7, 1H), 8.12 (s, 1H), 7.79-7.72 (m, 2H), 7.51 (d, J=2.8, 1 H), 7.43 (d, J=5.9, 1 H), 7.24-7.17 (m, 5H), 7.15-7.11 (m, 2H), 7.02 (d, J=7.9, 2H), 6.77 (t, J=7.3, 1H), 5.38-5.22 (br s, 2H); $^{13}$C NMR (101 MHz, DMSO-$d_6$) δ 154.7 (C), 152.7 (CH), 144.2 (C), 143.1 (CH), 137.3 (C), 136.4 (CH), 134.5 (C), 133.42 (C), 133.41 (C), 131.7 (CH), 131.6 (CH), 129.3 (2CH), 128.2 (C), 128.1 (2CH), 127.8 (CH), 127.39 (CH), 127.35 (2CH), 127.1 (CH), 121.4 (C), 119.3 (CH), 118.5 (CH), 115.4 (2CH), 66.90 ($CH_2$); HRMS (ESI+) calcd for $C_{27}H_{22}N_3O$ (M+H)$^+$ 404.1757, found 404.1763.

3-Phenyl-5-(phenylamino)pyridin-2(1H)-one (19)

Compound 19 was prepared according to general procedure C, starting from 12 (46.3 mg, 0.131 mmol). The mixture was stirred for 4 h and was quenched with $NEt_3$ (12 eq.) and MeOH (4 eq.). The crude was purified by column chromatography ($SiO_2$, EtOAc/MeOH 99.9:0.1 to 99.2:0.8) to give 19 (31.0 mg, 0.118 mmol, 90%) as a yellow solid.

$R_f$=0.20 ($CH_2Cl_2$/MeOH 97:3); Mp>153° C. (decomposition); IR (ATR) 3294, 1592, 1549, 1495, 1456, 1441, 863, 796, 784, 738 $cm^{-1}$; $^1H$ NMR (400 MHz, DMSO-$d_6$) δ 11.64 (br s, 1H), 7.73-7.69 (m, 2H), 7.52 (d, J=2.9, 1H), 7.51 (s, 1H), 7.41-7.36 (m, 2H), 7.34-7.28 (m, 1H), 7.19 (d, J=2.8, 1H), 7.14 (dd, J=8.4, 7.4, 2H), 6.75 (d, J=8.0, 2H), 6.68 (t, J=7.3, 1H); $^{13}C$ NMR (101 MHz, DMSO-$d_6$) δ 159.5 (C), 146.5 (C), 137.5 (CH), 136.5 (C), 129.9 (C), 129.2 (2CH), 128.2 (2CH), 127.9 (2CH), 127.5 (CH), 127.1 (CH), 122.8 (C), 117.9 (CH), 113.81 (2CH); HRMS (ESI+) calcd for $C_{17}H_{15}N_2O$ (M+H)$^+$263.1179, found 263.1173; HPLC purity≥99%, $t_R$=8.18 min, λ=284 nm.

3-(4-Fluorophenyl)-5-(phenylamino)pyridin-2(1H)-one (20)

Compound 20 was prepared according to general procedure C, starting from 13 (80.5 mg, 0.217 mmol). The mixture was stirred for 1 h. The crude was purified by column chromatography ($SiO_2$, $CH_2Cl_2$/MeOH 99.5:0.5 to 97:3) to give 20 (58.9 mg, 0.210 mmol, 97%) as a yellow solid.

$R_f$=0.35 ($CH_2Cl_2$/MeOH 94:6); Mp>198° C. (decomposition); IR (ATR) 3276, 1593, 1549, 1451, 1226, 830 $cm^{-1}$; $^1H$ NMR (400 MHz, DMSO-$d_6$) δ 11.69 (br s, 1H), 7.81-7.75 (m, 2H), 7.53 (d, J=2, 9, 1H), 7.51 (s, 1H), 7.24-7.11 (m, 5H), 6.74 (d, J=7.9, 2H), 6.68 (t, J=7.3, 1H); $^{13}C$ NMR (101 MHz, DMSO-$d_6$) δ 161.6 (d, $J_{CF}$=245, C), 159.5 (C), 146.5 (C), 137.5 (CH), 132.8 (d, $J_{CF}$=3, C), 130.2 (d, $J_{CF}$=8, 2CH), 129.2 (2CH), 128.8 (C), 127.1 (CH), 122.8 (C), 117.9 (CH), 114.8 (d, $J_{CF}$=21, 2CH), 113.8 (2CH); HRMS (ESI+) calcd for $C_{17}H_{14}FN_2O$ (M+H)$^+$281.1085, found 281.1087; HPLC purity≥99%, $t_R$=8.30 min, λ=282 nm.

5-(Phenylamino)-[3,4'-bipyridin]-2(1H)-one (21)

Compound 21 was prepared according to general procedure C, starting from 14 (59.2 mg, 0.168 mmol). The mixture was stirred for 2 h 30 min. The crude was purified by column chromatography ($SiO_2$, $CH_2Cl_2$/MeOH 99:1 to 95:5) to give 21 (35.5 mg, 0.135 mmol, 80%) as a yellow solid.

$R_f$=0.37 ($CH_2Cl_2$/MeOH 94:6); Mp>230° C. (decomposition); IR (ATR) 3220, 1661, 1631, 1596, 1460, 1325, 1258, 830 $cm^{-1}$; $^1H$ NMR (400 MHz, DMSO-$d_6$) δ 11.85 (br s, 1H), 8.56 (d, J=5.4, 2H), 7.82-7.79 (m, 2H), 7.76 (d, J=2.8, 1 H), 7.54 (s, 1H), 7.30 (d, J=2.8, 1H), 7.15 (t, J=7.8, 2H), 6.75 (d, J=7.9, 2H), 6.69 (t, J=7.3, 1H); $^{13}C$ NMR (101 MHz, DMSO-$d_6$) δ 159.2 (C), 149.4 (2CH), 146.4 (C), 143.6 (C), 138.9 (CH), 129.3 (2CH), 129.2 (CH), 126.6 (C), 122.8 (C), 122.4 (2CH), 118.0 (CH), 113.8 (2CH); HRMS (ESI+) calcd for $C_{16}H_{14}N_3O$ (M+H)$^+$264.1131, found 264.1134; HPLC purity≥97%, $t_R$=6.04 min, λ=270 nm.

3-(1H-Indol-3-yl)-5-(phenylamino)pyridin-2(1H)-one (22)

To a mixture under argon of 20% Pd(OH)$_2$/C (13.61 mg, 0.019 mmol, 0.25 eq.) and ethyl acetate (1 mL), previously degassed with argon, was added a solution of compound 15 (30.9 mg, 0.079 mmol, 1 eq.) in ethyl acetate (4.5 mL) previously degassed with argon. The mixture was then hydrogenated at room temperature for 15 h. The mixture was filtered through a pad of Celite which was then washed with ethyl acetate. The filtrate was evaporated under reduced pressure and the obtained red solid was purified by column chromatography ($SiO_2$, EtOAc+0.5% $NEt_3$ to EtOAc/MeOH 95:5+0.5% $NEt_3$) to give 22 (17.4 mg, 0.058 mmol, 73%) a red powder.

$R_f$=0.37 (EtOAc/MeOH 95:5+0.5% $NEt_3$); Mp>181° C. (decomposition); IR (ATR) 3450-3150, 1597, 1497, 1431, 734, 693 $cm^{-1}$; $^1H$ NMR (400 MHz, DMSO-$d_6$) δ 11.51 (br s, 1H), 11.39 (br s, 1H), 8.32 (d, J=2.6, 1H), 7.82-7.79 (m, 2H), 7.58 (s, 1H), 7.46 (d, J=8.0, 1H), 7.21-7.11 (m, 3H), 7.10-7.04 (m, 2H), 6.82 (d, J=8.0, 2H), 6.69 (t, J=7.3, 1H); $^{13}C$ NMR (101 MHz, DMSO-$d_6$) δ 159.5 (C), 146.5 (C), 136.2 (C), 132.6 (CH), 129.3 (2CH), 127.5 (CH), 126.3 (C), 125.1 (C), 122.7 (C), 122.2 (CH), 121.4 (CH), 119.7 (CH), 119.2 (CH), 117.9 (CH), 113.9 (2CH), 112.1 (CH), 109.6 (C); HRMS (ESI+) calcd for $C_{19}H_{16}N_3O$ (M+H)$^+$302.1288, found 302.1292; HPLC purity≥97%, $t_R$=8.19 min, λ=280 nm.

5-(Phenylamino)-3-(quinolin-8-yl)pyridin-2(1H)-one (23)

Compound 23 was prepared according to general procedure C, starting from 16 (80.3 mg, 0.199 mmol). The mixture was stirred for 2 h 40 min and was quenched with $NEt_3$ (12 eq.) and MeOH (4 eq.). After evaporation, EtOAc was added. The mixture was washed once with water and twice with a saturated aqueous $NaHCO_3$ solution, dried over $MgSO_4$ and filtered. After evaporation, the crude was purified by column chromatography ($SiO_2$, $CH_2Cl_2$/MeOH 99:1+0.5% $NEt_3$ to 96:4+0.5% $NEt_3$). The residue was dissolved in EtOAc and washed with water to eliminate the remaining triethylamine salts. After drying over $MgSO_4$, filtration and evaporation, 23 (11.9 mg, 0.0380 mmol, 19%) was obtained as a kaki powder. The poor yield could be explained by the poor solubility of the final product. Compound 23 was again prepared according to general procedure C, starting from 16 (133.8 mg, 0.332 mmol). The mixture was stirred for 3 h, quenched with $NEt_3$ (12 eq.) and MeOH (4 eq.) and then concentrated. The crude was filtered and washed with water, acetone and $CH_2Cl_2$. The compound 23 with important traces of $CH_2Cl_2$ was obtained (70 mg, containing about 10.5% wt $CH_2Cl_2$).

$R_f$=0.27 ($CH_2Cl_2$/MeOH 95:5); Mp>255° C. (decomposition); IR (ATR) 3245, 1649, 1578, 1557, 1494, 1335, 1258, 795, 750, 705 $cm^{-1}$; $^1H$ NMR (400 MHz, DMSO-$d_6$) δ 11.52 (br s, 1H), 8.88 (dd, J=4.1, 1.8, 1H), 8.39 (dd, J=8.3, 1.8, 1H), 7.97 (dd, J=8.2, 1.5, 1H), 7.85 (dd, J=7.1, 1.5, 1H), 7.63 (dd, J=8.1, 7.2, 1H), 7.56-7.51 (m, 3H), 7.23 (br s, 1H), 7.15 (dd, J=8.5, 7.3, 2H), 6.83 (dd, J=8.6, 1.0, 2H), 6.66 (tt, J=7.3, 1.0, 1H); $^{13}C$ NMR (101 MHz, DMSO-$d_6$) δ 159.8 (C), 150.0 (CH), 146.4 (C), 145.8 (C), 140.2 (CH), 136.3 (CH), 135.5 (C), 130.6 (CH), 129.3 (C), 129.2 (2CH), 128.1 (C), 127.9 (CH), 126.6 (CH), 125.9 (CH), 122.3 (C), 121.3 (CH), 117.8 (CH), 113.8 (2CH); HRMS (ESI+) calcd for $C_{20}H_{16}N_3O$ (M+H)$^+$314.1288, found 314.1291; HPLC purity≥96%, $t_R$=6.77 min, λ=282 nm.

5-(Phenylamino)-3-(pyrimidin-5-yl)pyridin-2(1H)-one (24)

Compound 24 was prepared according to general procedure C, starting from 17 (80.5 mg, 0.227 mmol). The mixture was stirred for 3 h 20 min and was quenched with NEt$_3$ (12 eq.) and MeOH (4 eq.). After evaporation, EtOAc was added. The mixture was washed with a saturated NaHCO$_3$ solution, dried over MgSO$_4$, and filtered. After evaporation, the crude was purified by column chromatography (SiO$_2$, CH$_2$Cl$_2$/MeOH 98:2 to 95:5) to give 24 (47.8 mg, 0.181 mmol, 80%) as a yellow solid.

R$_f$=0.12 (CH$_2$Cl$_2$/MeOH 95:5); Mp>160° C. (decomposition); IR (ATR) 3408, 3287, 1597, 1548, 1475, 742, 717, 694 cm$^{-1}$; $^1$H NMR (400 MHz, DMSO-d$_6$) δ 11.90 (br s, 1H), 9.15 (s, 2H), 9.10 (s, 1H), 7.82 (d, J=2.9, 1H), 7.56 (s, 1H), 7.30 (d, J=2.8, 1H), 7.14 (t, J=7.8, 2H), 6.76 (d, J=8.0, 2H), 6.68 (t, J=7.3, 1H); $^{13}$C NMR (101 MHz, DMSO-d$_6$) δ 159.2 (C), 156.9 (CH), 155.7 (2CH), 146.4 (C), 138.8 (CH), 130.2 (C), 129.2 (2CH), 128.9 (CH), 123.8 (C), 123.0 (C), 118.0 (CH), 113.8 (2CH); HRMS (ESI+) calcd for C$_{15}$H$_{13}$N$_4$O (M+H)$^+$265.1084, found 265.1090; HPLC purity≥96%, t$_R$=7.61 min, λ=284 nm.

3-(Isoquinolin-5-yl)-5-(phenylamino)pyridin-2(1H)-one (25)

Compound 25 was prepared according to general procedure C, starting from 18 (172 mg, 0.426 mmol). The mixture was stirred for 2 h 30 min and was quenched with NEt$_3$ (16 eq.) and MeOH (6 eq.). After evaporation, EtOAc was added. The mixture was washed with a saturated NaHCO$_3$ solution, dried over MgSO$_4$, and filtered. After evaporation, the crude was purified by column chromatography (SiO$_2$, CH$_2$Cl$_2$/MeOH 98:2 to 90:10) to give 25 (58.6 mg, 0.187 mmol, 44%) as a yellow solid.

R$_f$=0.16 (CH$_2$Cl$_2$/MeOH 94:6); Mp>209° C. (decomposition); IR (ATR) 3274, 1646, 1583, 1554, 1496, 1462, 745 cm$^{-1}$; $^1$H NMR (400 MHz, DMSO-d$_6$) δ 11.73 (br s, 1H), 9.34 (s, 1H), 8.47 (d, J=5.9, 1H), 8.15-8.11 (m, 1H), 7.74-7.70 (m, 2H), 7.56-7.53 (m, 2H), 7.44 (d, J=2.9, 1H), 7.35 (d, J=2.9, 1H), 7.15 (dd, J=8.5, 7.4, 2H), 6.80 (dd, J=8.6, 1.0, 2H), 6.68 (tt, J=7.3, 1.0, 1H); $^{13}$C NMR (101 MHz, DMSO-d$_6$) δ 159.4 (C), 152.6 (CH), 146.3 (C), 142.8 (CH), 139.9 (CH), 134.3 (C), 133.6 (C), 131.5 (CH), 129.3 (C), 129.2 (2CH), 128.3 (C), 128.0 (CH), 127.6 (CH), 127.0 (CH), 122.8 (C), 118.7 (CH), 118.0 (CH), 114.0 (2CH); HRMS (ESI+) calcd for C$_{20}$H$_{16}$N$_3$O (M+H)$^+$314.1288, found 314.1292; HPLC purity≥96%, t$_R$=6.47 min, λ=278 nm.

6-(Benzyloxy)-5-(quinolin-4-yl)-N-phenylpyridin-3-amine (46)

Compound 46 was prepared according to general procedure A, starting from 4 (201 mg, 0.566 mmol) and the corresponding boronic acid. The mixture was refluxed for 16 h. The crude oil was purified by column chromatography (SiO$_2$, EtOAc/cyclohexane 1:9 to 3:7) to give 46 (205 mg, 0.508 mmol, 90%) as a yellow powder.

R$_f$=0.16 (EtOAc/cyclohexane 2:8); Mp 156° C.; IR (ATR) 3232, 3179, 1597, 1438, 1229, 1022, 730, 694 cm$^{-1}$; $^1$H NMR (400 MHz, DMSO-d$_6$) δ 8.95 (d, J=4.4, 1H), 8.17 (s, 1H), 8.16 (d, J=2.8, 1H), 8.09 (d, J=8.4, 1H), 7.79 (ddd, J=8.4, 6.8, 1.6, 1H), 7.66 (dd, J=8.4, 1.4, 1 H), 7.58 (ddd, J=8.3, 6.8, 1.4, 1 H), 7.54 (d, J=2.8, 1 H), 7.52 (d, J=4.4, 1 H), 7.24-7.17 (m, 5H), 7.14-7.10 (m, 2H), 7.02 (dd, J=8.7, 1.1, 2H), 6.78 (tt, J=7.3, 1.0, 1H), 5.39-5.21 (br s, 2H); $^{13}$C NMR (101 MHz, DMSO-d$_6$) δ 154.3 (C), 150.1 (CH), 147.7 (C), 144.0 (C), 142.9 (C), 137.3 (C), 136.9 (CH), 134.5 (C), 131.0 (CH), 129.5 (CH), 129.4 (CH), 129.3 (2CH), 128.1 (2CH), 127.4 (CH), 127.3 (CH), 126.8 (CH), 126.2 (C), 125.9 (CH), 122.2 (CH), 120.3 (C), 119.4 (CH), 115.5 (2CH), 67.0 (CH$_2$); HRMS (ESI+) calcd for C$_{27}$H$_{22}$N$_3$O (M+H)$^+$404.1757, found 404.1763.

6-(Benzyloxy)-5-(1H-indol-4-yl)-N-phenylpyridin-3-amine (47)

Compound 47 was prepared according to general procedure A, starting from 4 (189 mg, 0.53 mmol) and the corresponding pinacol boronic ester. The mixture was refluxed for 16 h. The crude oil was purified by column chromatography (SiO$_2$, EtOAc/cyclohexane 5:95 to EtOAc/cyclohexane 15:85) to give 47 (207 mg, 0.53 mmol, quant.) as a grey powder. R$_f$=0.30 (EtOAc/cyclohexane 2:8); Mp 66° C.; IR (ATR) 3394, 1595, 1496, 1441, 1350, 1228, 748, 694 cm$^{-1}$; $^1$H NMR (400 MHz, DMSO-d$_6$) δ 11.19 (s, 1H), 8.06 (s, 1H), 8.02 (d, J=2.7, 1H), 7.58 (d, J=2.7, 1H), 7.43-7.10 (m, 11H), 6.99 (d, J=7.9, 2H), 6.76 (t, J=7.3, 1H), 6.32-6.30 (m, 1H), 5.35 (s, 2H); $^{13}$C NMR (101 MHz, DMSO-d$_6$) δ 154.7 (C), 144.5 (C), 137.7 (C), 136.0 (C), 135.3 (CH), 134.1 (C), 131.3 (CH), 129.3 (2CH), 128.1 (2CH), 127.9 (C), 127.4 (2CH), 127.3 (CH), 126.5 (C), 125.5 (CH), 123.7 (C), 120.7 (CH), 120.0 (CH), 119.0 (CH), 115.2 (2CH), 111.1 (CH), 100.5 (CH), 66.9 (CH$_2$); HRMS (ESI+) calcd for C$_{26}$H$_{22}$N$_3$O (M+H)$^+$392.1757, found 392.1751.

6-(Benzyloxy)-5-(2-chlorophenyl)-N-phenylpyridin-3-amine (48)

Compound 48 was prepared according to general procedure A, starting from 4 (125.2 mg, 0.352 mmol) and the corresponding boronic acid. The mixture was refluxed for 15 h 30 min. The crude oil was purified by column chromatography (SiO$_2$, pentane to EtOAc/pentane 1:9) to give 48 (116 mg, 0.300 mmol, 85%) a red oil.

R$_f$=0.34 (EtOAc/cyclohexane 1:9); IR (ATR) 3390, 1599, 1497, 1425, 1231, 736, 693 cm$^{-1}$; $^1$H NMR (400 MHz, DMSO-d$_6$) δ 8.10 (s, 1H), 8.03 (d, J=2.8, 1H), 7.58-7.53 (m, 1H), 7.47-7.38 (m, 4H), 7.33-7.23 (m, 5H), 7.20 (dd, J=8.5, 7.3, 2H), 6.97 (d, J=8.7, 1.1, 2H), 6.77 (tt, J=7.3, 1.0, 1H), 5.30 (s, 2H); $^{13}$C NMR (101 MHz, DMSO-d$_6$) δ 154.4 (C), 144.2 (C), 137.6 (C), 136.4 (CH), 135.2 (C), 134.0 (C), 132.6 (C), 131.8 (CH), 131.2 (CH), 129.6 (CH), 129.32 (2CH), 129.28 (CH), 128.2 (2CH), 127.4 (CH), 127.3 (2CH), 127.1 (CH), 121.9 (C), 119.2 (CH), 115.2 (2CH), 67.0 (CH$_2$); HRMS (ESI+) calcd for C$_{24}$H$_{20}$ClN$_2$O (M+H)$^+$ 387.1259, found 387.1248.

6-(Benzyloxy)-5-(2-bromophenyl)-N-phenylpyridin-3-amine (49)

Compound 49 was prepared according to general procedure A, starting from 4 (114.7 mg, 0.323 mmol) and the corresponding boronic acid. The mixture was refluxed for 16 h. The crude was chromatographed (SiO$_2$, cyclohexane to EtOAc/cyclohexane 1:9) but some impurity remained in the obtained orange oil (71 mg). Compound 49 was used for the next step without further purification. R$_f$=0.29 (EtOAc/cyclohexane 1:9).

Ethyl 2-(2-(benzyloxy)-5-(phenylamino)pyridin-3-yl)benzoate (50)

Compound 50 was prepared according to general procedure A, starting from 4 (123.5 mg, 0.348 mmol) and the corresponding boronic acid. The mixture was refluxed for 15 h. The crude oil was purified by column chromatography (SiO$_2$, cyclohexane to EtOAc/cyclohexane 1:9) to give 50 (110 mg, 0.259 mmol, 75%) an orange-brown oil. R$_f$=0.40 (EtOAc/cyclohexane 2:8); IR (ATR) 3372, 1708, 1598, 1430, 1253, 746, 693 cm$^{-1}$; $^1$H NMR (400 MHz, DMSO-d$_6$) δ 8.05 (s, 1H), 7.98 (d, J=2.7, 1H), 7.85 (dd, J=7.7, 1.4, 1H), 7.65 (td, J=7.6, 1.5, 1H), 7.50 (td, J=7.6, 1.3, 1 H), 7.41 (dd, J=7.6, 1.3, 1H), 7.39 (d, J=2.7, 1H), 7.33-7.22 (m, 5H), 7.20 (dd, J=8.6, 7.3, 2H), 6.96 (dd, J=8.6, 1.1, 2H), 6.76 (tt, J=7.3, 1.1, 1H), 5.24 (s, 2H), 3.98 (q, J=7.1, 2H), 0.95 (t, J=7.1, 3H); $^{13}$C NMR (101 MHz, DMSO-d$_6$) δ 166.8 (C), 154.3 (C), 144.6 (C), 137.4 (C), 136.6 (C), 135.5 (CH), 134.1 (C), 132.1 (CH), 131.1 (CH), 131.0 (C), 130.4 (CH), 129.5 (CH), 129.3 (2CH), 128.1 (2CH), 128.0 (CH), 127.4 (CH), 127.3 (2CH), 124.9 (C), 118.9 (CH), 115.0 (2CH), 66.8 (CH$_2$), 60.4 (CH$_2$), 13.6 (CH$_3$); HRMS (ESI+) calcd for C$_{27}$H$_{25}$N$_2$O$_3$ (M+H)$^+$425.1860, found 425.1857.

2-(2-(Benzyloxy)-5-(phenylamino)pyridin-3-yl)benzonitrile (51)

Compound 51 was prepared according to general procedure A, starting from 4 (152 mg, 0.428 mmol) and the corresponding boronic acid. The mixture was refluxed for 15 h. The crude was chromatographed (SiO$_2$, pentane to EtOAc/pentane) but some impurities remained in the obtained white solid (131.6 mg). Compound 51 was used for the next step without further purification. R$_f$=0.35 (EtOAc/pentane 5:5).

6-(Benzyloxy)-5-(2-nitrophenyl)-N-phenylpyridin-3-amine (52)

To a solution under argon of 4 (201.4 mg, 0.567 mmol, 1 eq.) in 1,4-dioxane (0.5 mL) were added the 2-nitrophenylboronic acid (95.1 mg, 0.57, 1 eq.) and a 2 M aqueous K$_2$CO$_3$ solution (4 eq.). The mixture was degassed with argon for 10 min before the addition of Pd(dppf)Cl$_2$ (24.4 mg, 0.033 mmol, 0.06 eq.). The solution was stirred at 100° C. Additional portions of boronic acid were added after 2 h 30 min (47.3 mg, 0.283 mmol, 0.5 eq.), 17 h 30 min (31.6 mg, 0.189 mmol, 0.33 eq.) and 24 h (47.4 mg, 0.284 mmol, 0.5 eq.). The mixture was then stirred at 100° C. overnight. Ethyl acetate was added and the resulting mixture was washed with water. The organic phase was dried over MgSO$_4$ and filtered. After evaporation under reduced pressure, the crude was purified by column chromatography (SiO$_2$, cyclohexane to EtOAc/cyclohexane 1:9) to give the desired product 52 (83.1 mg, 0.209 mmol, 37%) as an orange powder.

R$_f$=0.41 (EtOAc/cyclohexane 2:8); Mp 141° C.; IR (ATR) 3370, 1453, 1351, 1295, 1250, 1219, 990, 730, 693 cm$^{-1}$; $^1$H NMR (400 MHz, DMSO-d$_6$) δ 8.14 (s, 1H), 8.05 (dd, J=8.1, 1.2, 1H), 8.01 (d, J=2.7, 1H), 7.80 (td, J=7.6, 1.3, 1H), 7.64 (ddd, J=8.1, 7.5, 1.5, 1H), 7.60 (dd, J=7.6, 1.3, 1H), 7.55 (d, J=2.7, 1H), 7.33-7.19 (m, 7H), 7.00 (dd, J=8.6, 1.1, 2H), 6.79 (tt, J=7.3, 1.1, 1H), 5.21 (br s, 2H); $^{13}$C NMR (101 MHz, DMSO-d$_6$) δ 153.5 (C), 148.6 (C), 144.2 (C), 137.0 (C), 136.1 (CH), 134.7 (C), 133.8 (CH), 132.6 (CH), 130.6 (C), 129.9 (CH), 129.4 (CH), 129.3 (2CH), 128.2 (2CH), 127.5 (CH), 127.4 (2CH), 124.3 (CH), 121.3 (C), 119.3 (CH), 115.3 (2CH), 67.2 (CH$_2$); HRMS (ESI+) calcd for C$_{24}$H$_{20}$N$_3$O$_3$ (M+H)$^+$398.1499, found 398.1487.

5-([1,1'-biphenyl]-4-yl)-6-(benzyloxy)-N-phenylpyridin-3-amine (53)

Compound 53 was prepared according to general procedure A, starting from 4 (119 mg, 0.335 mmol) and the corresponding boronic acid. The mixture was refluxed for 16 h. The crude oil was purified by column chromatography (SiO$_2$, cyclohexane to EtOAc/cyclohexane 1:9) to give 53 (30.8 mg) and a second fraction containing trace of 4-phenylphenol. CH$_2$Cl$_2$ was added to the second fraction which was washed with a 0.5 M aqueous NaOH solution, and then with water. The organic phase was dried over MgSO$_4$, filtered and evaporated to give pure 53 (99.8 mg). Compound 53 (130.6 mg, 0.305 mmol, 91%) was obtained as a light brown solid.

R$_f$=0.27 (EtOAc/cyclohexane 1:9); Mp 109° C.; IR (ATR) 3304, 1595, 1437, 1232, 1006, 841, 721, 690 cm$^{-1}$; $^1$H NMR (400 MHz, DMSO-d$_6$) δ 8.09 (s, 1H), 8.00 (d, J=2.7, 1H), 7.76-7.69 (m, 6H), 7.60 (d, J=2.8, 1H), 7.51-7.41 (m, 4H), 7.40-7.34 (m, 3H), 7.32-7.26 (m, 1H), 7.21 (dd, J=8.6, 7.3, 2H), 7.00 (dd, J=8.7, 1.1, 2H), 6.78 (tt, J=7.3, 1.1, 1H), 5.41 (s, 2H); $^{13}$C NMR (101 MHz, DMSO-d$_6$) δ 154.3 (C), 144.4 (C), 139.6 (C), 139.3 (C), 137.7 (C), 135.7 (CH), 135.2 (C), 134.6 (C), 130.3 (CH), 129.5 (2CH), 129.3 (2CH), 129.0 (2CH), 128.3 (2CH), 127.6 (CH), 127.5 (CH), 127.4 (2CH), 126.6 (2CH), 126.5 (2CH), 123.3 (C), 119.1 (CH), 115.2 (2CH), 67.1 (CH$_2$); HRMS (ESI+) calcd for C$_{30}$H$_{25}$N$_2$O (M+H)$^+$429.1961, found 429.1972.

6-(Benzyloxy)-5-(3-chlorophenyl)-N-phenylpyridin-3-amine (54)

Compound 54 was prepared according to general procedure A, starting from 4 (117 mg, 0.329 mmol). The mixture was refluxed for 16 h. The crude oil was purified by column chromatography (SiO$_2$, cyclohexane to EtOAc/cyclohexane 1:9) to give 54 (121.3 mg, 0.314 mmol, 95%) as a red oil.

R$_f$=0.40 (EtOAc/cyclohexane 1:9); IR (ATR) 3378, 1602, 1589, 1439, 1409, 1359, 1298, 1256, 1217, 1013, 894, 754, 728, 692 cm$^{-1}$; $^1$H NMR (400 MHz, DMSO-d$_6$) δ 8.09 (s, 1H), 8.02 (d, J=2.7, 1H), 7.71 (t, J=1.7, 1H), 7.58 (d, J=2.7, 1H), 7.56 (dt, J=7.5, 1.5, 1H), 7.46 (t, J=7.7, 1H), 7.44-7.40 (m, 3H), 7.39-7.33 (m, 2H), 7.32-7.27 (m, 1H), 7.21 (dd, J=8.5, 7.4, 2H), 6.99 (dd, J=8.6, 1.0, 2H), 6.78 (tt, J=7.3, 1.1, 1H), 5.38 (s, 2H); $^{13}$C NMR (101 MHz, DMSO-d$_6$) δ 154.1 (C), 144.3 (C), 138.2 (C), 137.5 (C), 136.3 (CH), 134.6 (C), 132.9 (C), 130.4 (CH), 130.2 (CH), 129.4 (2CH), 128.9 (CH), 128.3 (2CH), 127.7 (CH), 127.6 (CH), 127.5 (CH), 127.4 (2CH), 122.2 (C), 119.2 (CH), 115.2 (2CH), 67.2 (CH$_2$); HRMS (ESI+) calcd for C$_{24}$H$_{20}$ClN$_2$O(M+H)$^+$ 387.1259, found 387.1268.

1-(3-(2-(Benzyloxy)-5-(phenylamino)pyridin-3-yl)phenyl)ethan-1-one (55)

Compound 55 was prepared according to general procedure A, starting from 4 (117.5 mg, 0.331 mmol) and the corresponding boronic acid. The mixture was refluxed for 15 h. The crude oil was purified by column chromatography (SiO$_2$, cyclohexane to EtOAc/cyclohexane 15:85) to give 55 (130.6 mg, 0.331 mmol, quant.) a brown oil.

R$_f$=0.41 (EtOAc/cyclohexane 2:8); IR (ATR) 3367, 1669, 1596, 1535, 1497, 1490, 1442, 1417, 1246, 1218, 1009, 734, 693 cm$^{-1}$; $^1$H NMR (400 MHz, DMSO-d$_6$) δ 8.21 (td, J=1.8, 0.5, 1H), 8.10 (s, 1H), 8.04 (d, J=2.7, 1H), 7.93 (ddd, J=7.8, 1.8, 1.1, 1H), 7.86 (ddd, J=7.7, 1.9, 1.1, 1 H), 7.62 (d, J=2.8, 1 H), 7.59 (td, J=7.8, 0.5, 1 H), 7.45-7.41 (m, 2H), 7.38-7.32 (m, 2H), 7.32-7.26 (m, 1H), 7.21 (dd, J=8.6, 7.3, 2H), 6.99 (dd, J=8.7, 1.1, 2H), 6.78 (tt, J=7.3, 1.1, 1H), 5.38 (s, 2H), 2.56 (s, 3H); $^{13}$C NMR (101 MHz, DMSO-d$_6$) δ 197.7 (C), 154.3 (C), 144.4 (C), 137.5 (C), 136.8 (C), 136.4 (C), 136.2 (CH), 134.6 (C), 133.6 (CH), 130.6 (CH), 129.3 (2CH), 129.0 (CH), 128.7 (CH), 128.3 (2CH), 127.58 (2CH), 127.57 (CH), 127.2 (CH), 122.8 (C), 119.1 (CH), 115.2 (2CH), 67.2 (CH$_2$), 26.7 (CH$_3$); HRMS (ESI+) calcd for C$_{26}$H$_{23}$N$_2$O$_2$ (M+H)$^+$395.1754, found 395.1748.

4-(2-(Benzyloxy)-5-(phenylamino)pyridin-3-yl)phenol (56)

Compound 56 was prepared according to general procedure A, starting from 4 (147 mg, 0.414 mmol) and the corresponding boronic acid. The mixture was refluxed for 15 h. The crude oil was purified by column chromatography (SiO$_2$, EtOAc/cyclohexane 5:95 to 2:8). The obtained yellow solid was then dissolved in ethyl acetate and washed with water. The organic phase was dried over MgSO$_4$, filtered and evaporated to give 56 (115 mg, 0.312 mmol, 75%) as a pale yellow solid.

R$_f$=0.24 (EtOAc/cyclohexane 8:2); Mp 172° C.; IR (ATR) 3389, 1597, 1528, 1249, 1211, 1023, 725, 689 cm$^{-1}$; $^1$H NMR (400 MHz, DMSO-d$_6$) δ 9.55 (s, 1H), 7.99 (s, 1H), 7.92 (d, J=2.7, 1H), 7.47 (d, J=2.7, 1H), 7.43 (d, J=8.7, 2H), 7.43-7.39 (m, 2H), 7.38-7.33 (m, 2H), 7.31-7.26 (m, 1H), 7.20 (dd, J=8.4, 7.4, 2H), 6.96 (dd, J=8.6, 1.0, 2H), 6.80 (d, J=8.7, 2H), 6.76 (tt, J=7.3, 1.0, 1H), 5.36 (s, 2H); $^{13}$C NMR (101 MHz, DMSO-d$_6$) δ 157.0 (C), 154.3 (C), 144.5 (C), 137.8 (C), 134.8 (CH), 134.4 (C), 130.2 (2CH), 130.0 (CH), 129.3 (2CH), 128.3 (2CH), 127.4 (CH), 127.3 (2CH), 126.6 (C), 123.9 (C), 118.9 (CH), 115.10 (2CH), 115.06 (2CH), 67.0 (CH$_2$); HRMS (ESI+) calcd for C$_{24}$H$_{21}$N$_2$O$_2$ (M+H)$^+$ 369.1598, found 369.1587.

6-(Benzyloxy)-N-phenyl-5-(p-tolyl)pyridin-3-amine (57)

Compound 57 was prepared according to general procedure A, starting from 4 (120 mg, 0.338 mmol) and the corresponding boronic acid. The mixture was refluxed for 15 h. The crude oil was purified by column chromatography (SiO$_2$, cyclohexane to EtOAc/cyclohexane 1:9) to give 57 containing trace of 4-methylphenol. EtOAc was added and the organic phase washed with a 0.5 M aqueous NaOH solution, and then with water. The organic phase was dried over MgSO$_4$, filtered and evaporated to give 57 (106 mg, 0.289 mmol, 86%) as an orange solid.

R$_f$=0.37 (EtOAc/cyclohexane 1:9); Mp 72° C.; IR (ATR) 3313, 1594, 1440, 1231, 1025, 868, 822, 730, 692 cm$^{-1}$; $^1$H NMR (400 MHz, DMSO-d$_6$) δ 8.05 (s, 1H), 7.97 (d, J=2.7, 1H), 7.51 (d, J=2.8, 1H), 7.50 (d, J=8.2, 2H), 7.42-7.39 (m, 2H), 7.38-7.33 (m, 2H), 7.31-7.26 (m, 1H), 7.23 (d, J=7.8, 2H), 7.20 (dd, J=8.6, 7.3, 2H), 6.97 (dd, J=8.7, 1.1, 2H), 6.76 (tt, J=7.3, 1.1, 1H), 5.36 (s, 2H), 2.32 (s, 3H); $^{13}$C NMR (101 MHz, DMSO-d$_6$) δ 154.3 (C), 144.5 (C), 137.7 (C), 137.0 (C), 135.4 (CH), 134.5 (C), 133.2 (C), 130.4 (CH), 129.3 (2CH), 128.85 (2×2CH), 128.3 (2CH), 127.49 (CH), 127.46 (2CH), 123.8 (C), 119.0 (CH), 115.1 (2CH), 67.1 (CH$_2$), 20.8 (CH$_3$); HRMS (ESI+) calcd for C$_{25}$H$_{23}$N$_2$O (M+H)$^+$ 367.1805, found 367.1797.

6-(Benzyloxy)-N-phenyl-5-(4-(trifluoromethyl)phenyl)pyridin-3-amine (58)

Compound 58 was prepared according to general procedure A, starting from 4 (152 mg, 0.43 mmol) and the corresponding boronic acid. The mixture was refluxed for 18 h. The crude green oil was purified by column chromatography (SiO$_2$, EtOAc/cyclohexane 5:95 to 2:8) to give 58 (149 mg, 0.35 mmol, 83%) as a pale yellow oil which solidified to a yellow solid.

R$_f$=0.51 (EtOAc/cyclohexane 2:8); Mp 109° C.; IR (ATR) 3383, 3336, 1598, 1442, 1322, 1123, 1111, 1068, 845, 738, 693 cm$^{-1}$; $^1$H NMR (400 MHz, DMSO-d$_6$) δ 8.10 (s, 1H), 8.05 (d, J=2.8, 1H), 7.84 (d, J=8.2, 2H), 7.78 (d, J=8.4, 2H), 7.61 (d, J=2.8, 1H), 7.42-7.39 (m, 2H), 7.38-7.33 (m, 2H), 7.31-7.26 (m, 1H), 7.21 (dd, J=8.5, 7.3, 2H), 7.00 (dd, J=8.6, 1.1, 2H), 6.78 (tt, J=7.3, 1.1, 1H), 5.40 (s, 2H); $^{13}$C NMR (101 MHz, DMSO-d$_6$) δ 154.1 (C), 144.2 (C), 140.3 (C), 137.5 (C), 136.5 (CH), 134.7 (C), 130.5 (CH), 129.8 (2CH), 129.3 (2CH), 128.3 (2CH), 127.9 (q, J$_{CF}$=32, C), 127.52 (CH), 127.46 (2CH), 125.1 (q, J$_c$F=4, 2CH), 124.2 (q, J$_c$F=272, C), 122.2 (C), 119.2 (CH), 115.3 (2CH), 67.2 (CH$_2$); HRMS (ESI+) calcd for C$_{25}$H$_{20}$F$_3$N$_2$O (M+H)$^+$ 421.1522, found 421.1539.

6-(Benzyloxy)-N-phenyl-5-(4-(trifluoromethoxy)phenyl)pyridin-3-amine (59)

Compound 59 was prepared according to general procedure A, starting from 4 (115.1 mg, 0.324 mmol) and the corresponding boronic acid. The mixture was refluxed for 16 h. The crude was purified by column chromatography (SiO$_2$, cyclohexane to EtOAc/cyclohexane 1:9) to give 59 (128.1 mg, 0.293 mmol, 91%) as a grey solid.

R$_f$=0.36 (EtOAc/cyclohexane 1:9); Mp 83° C.; IR (ATR) 3394, 1598, 1443, 1258, 1206, 1163, 1047, 1017, 734, 695 cm$^{-1}$; $^1$H NMR (400 MHz, DMSO-d$_6$) δ 8.09 (s, 1H), 8.01 (d, J=2.7, 1H), 7.74 (d, J=8.9, 2H), 7.57 (d, J=2.8, 1H), 7.45-7.33 (m, 6H), 7.31-7.26 (m, 1H), 7.20 (dd, J=8.5, 7.4, 2H), 6.99 (dd, J=8.6, 1.0, 2H), 6.78 (tt, J=7.4, 1.0, 1H), 5.38 (s, 2H); $^{13}$C NMR (101 MHz, DMSO-d$_6$) δ 154.1 (C), 147.7 (q, J=2, C), 144.3 (C), 137.6 (C), 136.1 (CH), 135.4 (C), 134.6 (C), 131.0 (2CH), 130.4 (CH), 129.3 (2CH), 128.3 (2CH), 127.5 (CH), 127.4 (CH), 122.3 (C), 120.8 (2CH), 120.1 (q, J=256, C), 119.2 (CH), 115.3 (2CH), 67.1 (CH$_2$); HRMS (ESI+) calcd for C$_{25}$H$_{20}$F$_3$N$_2$O$_2$ (M+H)$^+$437.1463, found 437.1471.

Methyl 4-(2-(benzyloxy)-5-(phenylamino)pyridin-3-yl)benzoate (60)

Compound 60 was prepared according to general procedure A, starting from 4 (98.9 mg, 0.278 mmol) and the corresponding boronic acid. The mixture was refluxed for 16 h. The crude was purified by column chromatography (SiO$_2$, cyclohexane to EtOAc/cyclohexane 15:85) to give 60 (68.8 mg, 0.168 mmol, 60%) as a yellow powder.

R$_f$=0.46 (EtOAc/cyclohexane 2:8); Mp 139° C.; IR (ATR) 3374, 1707, 1695, 1598, 1280, 1261, 861, 729, 695 cm$^{-1}$; $^1$H NMR (400 MHz, DMSO-d$_6$) δ 8.11 (s, 1H), 8.04 (d, J=2.7, 1 H), 8.00 (d, J=8.6, 2H), 7.77 (d, J=8.6, 2H), 7.60 (d, J=2.7, 1 H), 7.43-7.39 (m, 2H), 7.39-7.33 (m, 2H), 7.32-7.26 (m, 1H), 7.21 (dd, J=8.5, 7.3, 2H), 6.99 (dd, J=8.6, 1.1, 2H), 6.78 (tt, J=7.3, 1.1, 1H), 5.38 (s, 2H), 3.86 (s, 3H); $^{13}$C NMR (101 MHz, DMSO-d$_6$) δ 166.0 (C), 154.2 (C), 144.3 (C), 141.0 (C), 137.5 (C), 136.5 (CH), 134.7 (C), 130.5 (CH), 129.39 (2CH), 129.35 (2CH), 129.1 (2CH), 128.6 (C), 128.4 (2CH), 127.6 (CH), 127.5 (2CH), 122.6 (C), 119.2 (CH), 115.3 (2CH), 67.3 (CH$_2$), 52.2 (CH$_3$); HRMS (ESI+) calcd for C$_{26}$H$_{23}$N$_2$O$_3$ (M+H)$^+$411.1703, found 411.1702.

4-(2-(Benzyloxy)-5-(phenylamino)pyridin-3-yl)benzamide (61)

Compound 61 was prepared according to general procedure A, starting from 4 (115 mg, 0.324 mmol) and the corresponding boronic acid. The mixture was refluxed for 16 h. The crude was purified by column chromatography (SiO$_2$, EtOAc/cyclohexane 3:7 to 6:4) but some impurities remained in the obtained white powder (133 mg). Compound 61 was used for the next step without further purification. R$_f$=0.09 (EtOAc/cyclohexane 3:7).

6-(Benzyloxy)-5-(2,4-difluorophenyl)-N-phenylpyridin-3-amine (62)

Compound 62 was prepared according to general procedure A, starting from 4 (115 mg, 0.324 mmol) and the corresponding boronic acid. The mixture was refluxed for 22 h. Due to the presence of residual starting material 4, catalyst PdCl$_2$(PPh$_3$)$_2$ was added (5.1 mg, 0.0073 mmol, 0.02 eq.) and the mixture was refluxed for additional 17 h. The crude was chromatographed (SiO$_2$, pentane to EtOAc/pentane 6:94) but some impurities remained in the obtained pink-brown oil (97.6 mg). Compound 62 was used for the next step without further purification. R$_f$=0.21 (EtOAc/pentane 5:95).

6-(Benzyloxy)-5-(1H-indol-7-yl)-N-phenylpyridin-3-amine (63)

Indole-7-boronic acid was prepared from 7-bromoindole according to literature procedure (Prieto et al. *J. Org. Chem.* 2007, 72, 1047-1050). To a solution under argon cooled to 0° C. of 7-bromoindole (171 mg, 0.87 mmol, 1 eq.) in anhydrous THF (1.4 mL) was added a suspension of KH (30% dispersion in mineral oil, 121.6 mg, 0.91 mmol, 1 eq.) in anhydrous THF (0.33 mL) cooled to 0° C. The mixture was stirred at 0° C. for 20 min then was cooled to −78° C. and a 1.08 M t-butyllithium solution in pentane (1.65 mL, 1.78 mmol, 2 eq.) cooled to −78° C. was added dropwise. The mixture was then stirred at room temperature for 15 min in the dark. The mixture was cooled to −78° C. and trimethyl borate was added (0.19 mL, 1.7 mmol, 2 eq.). The mixture was stirred at room temperature for 3 h. Water was added and the mixture was washed with EtOAc. Aqueous phase was acidified with a 10% HCl solution (pH 1) and was extracted with EtOAc. The organic phase was dried over MgSO$_4$, filtered and evaporated giving a 46:54 mixture of indole-7-boronic acid and indole (213 mg, ratio evaluated by $^1$H-NMR). The obtained crude was used without purification.

Compound 63 was prepared according to general procedure A, starting from 4 (105.1 mg, 0.296 mmol) and the mixture of indole-7-boronic acid and indole obtained in the preceding step. The reaction mixture was refluxed for 15.5 h. The crude oil was purified by column chromatography (SiO$_2$, cyclohexane to EtOAc/cyclohexane 2:8) to give 63 (57 mg, 0.146 mmol, 49%) as a beige powder.

R$_f$=0.32 (EtOAc/cyclohexane 2:8); Mp 135° C.; IR (ATR) 3389, 3316, 1596, 1497, 1420, 1230, 1023, 798, 722, 692 cm$^{-1}$; $^1$H NMR (400 MHz, DMSO-d$_6$) δ 10.91 (s, 1H), 8.09 (s, 1H), 8.08 (d, J=2.8, 1H), 7.57-7.53 (m, 1H), 7.55 (d, J=2.8, 1H), 7.30 (t, J=2.9, 1H), 7.24-7.17 (m, 7H), 7.08-6.99 (m, 4H), 6.76 (tt, J=7.3, 1.1, 1H), 6.47 (dd, J=3.1, 1.9, 1H), 5.34 (s, 2H); $^{13}$C NMR (101 MHz, DMSO-d$_6$) δ 154.9 (C), 144.5 (C), 137.5 (C), 135.7 (CH), 134.3 (C), 133.6 (C), 131.2 (CH), 129.3 (2CH), 128.0 (2CH), 127.9 (C), 127.5 (2CH), 127.3 (CH), 125.5 (CH), 122.2 (CH), 122.0 (C), 120.6 (C), 119.9 (CH), 119.0 (CH), 118.8 (CH), 115.1 (2CH), 101.1 (CH), 67.1 (CH$_2$); HRMS (ESI+) calcd for C$_{26}$H$_{22}$N$_3$O (M+H)$^+$392.1757, found 392.1754.

5-(3-Aminophenyl)-6-(benzyloxy)-N-phenylpyridin-3-amine (64)

Compound 64 was prepared according to general procedure A, starting from 4 (121.6 mg, 0.342 mmol) and the corresponding boronic acid. The mixture was refluxed for 15 h 30 min. The crude oil was purified by column chromatography (SiO$_2$, EtOAc/cyclohexane 2:8 to 25:75) to give 64 (120.2 mg, 0.327 mmol, 96%) a light yellow oil.

R$_f$=0.07 (EtOAc/cyclohexane 1:9); Mp 106° C.; IR (ATR) 3380, 1586, 1426, 1360, 1020, 754, 735, 693 cm$^{-1}$; $^1$H NMR (400 MHz, DMSO-d$_6$) δ 8.02 (s, 1H), 7.93 (d, J=2.8, 1H), 7.45 (d, J=2.8, 1H), 7.43-7.39 (m, 2H), 7.37-7.32 (m, 2H), 7.30-7.25 (m, 1H), 7.20 (dd, J=8.6, 7.4, 2H), 7.05 (t, J=7.8, 1H), 6.96 (dd, J=8.6, 1.1, 2H), 6.79-6.72 (m, 3H), 6.54 (ddd, J=8.0, 2.3, 1.0, 1H), 5.36 (s, 2H), 5.11 (br s, 2H); $^{13}$C NMR (101 MHz, DMSO-d$_6$) δ 154.3 (C), 148.5 (C), 144.4 (C), 137.8 (C), 136.7 (C), 135.2 (CH), 134.3 (C), 130.2 (CH), 129.3 (2CH), 128.6 (CH), 128.3 (2CH), 127.4 (CH), 127.3 (2CH), 124.7 (C), 119.0 (CH), 116.6 (CH), 115.2 (2CH), 114.4 (CH), 113.2 (CH), 66.9 (CH$_2$); HRMS (ESI+) calcd for C$_{24}$H$_{22}$N$_3$O (M+H)$^+$368.1757, found 368.1743.

6-(Benzyloxy)-5-(3-methoxyphenyl)-N-phenylpyridin-3-amine (65)

Compound 65 was prepared according to general procedure A, starting from 4 (114 mg, 0.321 mmol) and the corresponding boronic acid. The mixture was refluxed for 15 h 30 min. The crude oil was purified by column chromatography (SiO$_2$, cyclohexane to EtOAc/cyclohexane 8:92) to give a mixture of 65 and 3-methoxyphenol. Ethyl acetate was added and the organic phase was washed with an 0.5 M NaOH aqueous solution of and then with water. The organic phase was dried over MgSO$_4$, filtered and then evaporated to give 65 (106 mg, 0.277 mmol, 86%) a brown oil.

R$_f$=0.57 (EtOAc/cyclohexane 2:8); IR (ATR) 3375, 1587, 1418, 1360, 1262, 1014, 864, 754, 693 cm$^{-1}$; $^1$H NMR (400 MHz, DMSO-d$_6$) δ 8.06 (s, 1H), 8.00 (d, J=2.7, 1H), 7.55 (d, J=2.7, 1H), 7.44-7.41 (m, 2H), 7.38-7.27 (m, 4H), 7.23-7.18 (m, 3H), 7.14 (ddd, J=7.7, 1.5, 1.0, 1H), 6.98 (dd, J=8.6, 1.0, 2H), 6.91 (ddd, J=8.3, 2.6, 0.9, 1H), 6.77 (tt, J=7.3, 1.1, 1H), 5.36 (s, 2H), 3.72 (s, 3H); $^{13}$C NMR (101 MHz, DMSO-d$_6$) δ 158.9 (C), 154.3 (C), 144.4 (C), 137.6 (C), 137.4 (C), 135.7 (CH), 134.5 (C), 130.5 (CH), 129.31 (2CH), 129.30 (CH), 128.3 (2CH), 127.61 (CH), 127.56 (CH), 123.6 (C), 121.2 (CH), 119.1 (CH), 115.1 (2CH), 114.3 (CH), 113.6 (CH), 67.1 (CH$_2$), 55.0 (CH$_3$); HRMS (ESI+) calcd for C$_{25}$H$_{23}$N$_2$O$_2$ (M+H)$^+$383.1751, found 383.1754.

5-(Phenylamino)-3-(quinolin-4-yl)pyridin-2(1H)-one (66)

Compound 66 was prepared according to general procedure C, starting from 46 (100 mg, 0.248 mmol). The mixture was stirred for 3 h and was quenched with NEt$_3$ (12 eq.) and MeOH (4 eq.). After evaporation, EtOAc was added. The mixture was washed with brine, then the organic phase was dried over MgSO$_4$, and filtered. After evaporation, the crude was purified by column chromatography (SiO$_2$, CH$_2$Cl$_2$/MeOH 98:2). EtOAc was added to the obtained product which was then washed with water to remove residual NEt$_3$ salts. The organic phase was dried over MgSO$_4$, filtered and concentrated to give 66 (54 mg, 0.172 mmol, 69%) as a light brown solid.

R$_f$=0.17 (CH$_2$Cl$_2$/MeOH 95:5); Mp>275° C. (decomposition); IR (ATR) 1627, 1592, 1561, 1479, 1337, 1255, 836, 742, 689 cm$^{-1}$; $^1$H NMR (400 MHz, DMSO-d$_6$) δ 11.84 (br s, 1H), 8.91 (d, J=4.4, 1H), 8.06 (d, J=8.3, 1H), 7.80-7.74 (m, 2H), 7.60-7.55 (m, 2H), 7.49 (d, J=3.0, 1H), 7.46 (d, J=4.4, 1H), 7.38 (br s, 1H), 7.15 (dd, J=8.6, 7.3, 2H), 6.80 (dd, J=8.6, 1.0, 2H), 6.68 (tt, J=7.3, 1.1, 1H); $^{13}$C NMR (101 MHz, DMSO-d$_6$) δ 159.0 (C), 150.1 (CH), 147.8 (C), 146.2 (C), 143.5 (C), 139.9 (CH), 129.30 (CH), 129.27 (CH), 129.25 (2CH), 128.7 (CH), 128.1 (C), 126.4 (CH), 126.3 (C), 126.0 (CH), 122.9 (C), 122.1 (CH), 118.1 (CH), 114.0 (2CH); HRMS (ESI+) calcd for C$_{20}$H$_{16}$N$_3$O(M+H)$^+$ 314.1288, found 314.1291; HPLC purity≥96%, t$_R$=6.83 min, λ=280 nm.

3-(1H-Indol-4-yl)-5-(phenylamino)pyridin-2(1H)-one (67)

Compound 67 was prepared according to general procedure C, starting from 47 (96.6 mg, 0.247 mmol). The mixture was stirred for 6 h and was quenched with NEt$_3$ (15 eq.) and MeOH (5 eq.). After evaporation, EtOAc was added. The mixture was washed with H$_2$O, dried over MgSO$_4$, and filtered. After evaporation, the crude was purified by column chromatography (SiO$_2$, EtOAc/cyclohexane 6:4 to 9:1) to give 67 (49.9 mg, 0.166 mmol, 67%) as a yellow solid.

R$_f$=0.13 (EtOAc/cyclohexane 6:4); Mp>143° C. (decomposition); IR (ATR) 3500-3000, 1595, 1495, 1333, 1250, 746, 691 cm$^{-1}$; $^1$H NMR (400 MHz, DMSO-d$_6$) δ 11.56 (br s, 1H), 11.14 (s, 1H), 7.52 (d, J=3.0, 1H), 7.51 (s, 1H), 7.37-7.33 (m, 2H), 7.27 (dd, J=7.3, 0.9, 1H), 7.20 (br s, 1H), 7.15 (dd, J=8.5, 7.3, 2H), 7.09 (t, J=7.7, 1H), 6.77 (dd, J=8.6, 1.0, 2H), 6.68 (tt, J=7.3, 1.1, 1H), 6.37-6.35 (m, 1H); $^{13}$C NMR (101 MHz, DMSO-d$_6$) δ 159.6 (C), 146.6 (C), 138.3 (CH), 136.1 (C), 130.6 (C), 129.2 (2CH), 128.3 (C), 126.7 (CH), 126.1 (C), 125.4 (CH), 122.5 (C), 120.5 (CH), 119.9 (CH), 117.9 (CH), 113.9 (2CH), 110.9 (CH), 100.5 (CH); HRMS (ESI+) calcd for C$_{19}$H$_{16}$N$_3$O (M+H)$^+$ 302.1288, found 302.1282. HPLC purity≥95%, t$_R$=7.82 min, λ=278 nm.

3-(2-Chlorophenyl)-5-(phenylamino)pyridin-2(1H)-one (68)

Compound 68 was prepared according to general procedure C, starting from 48 (82.1 mg, 0.212 mmol). The mixture was stirred for 2 h 40 min and was quenched with NEt$_3$ (12 eq.) and MeOH (6 eq.). The crude was purified by column chromatography (SiO$_2$, EtOAc/cyclohexane 6:4 to 75:25). The product was washed with CH$_2$Cl$_2$ to give 68 (31.4 mg, 0.106 mmol, 50%) as a light yellow-green powder.

R$_f$=0.12 (EtOAc/cyclohexane 7:3); Mp>231° C.; IR (ATR) 3267, 1654, 1593, 1563, 745, 696 cm$^{-1}$; $^1$H NMR (400 MHz, DMSO-d$_6$) δ 11.64 (br s, 1H), 7.53-7.48 (m, 2H), 7.41-7.34 (m, 3H), 7.32 (d, J=2.9, 1H), 7.27-7.23 (br s, 1H), 7.14 (dd, J=8.5, 7.4, 2H), 6.75 (dd, J=8.6, 1.0, 2H), 6.68 (tt, J=7.3, 1.0, 1H); $^{13}$C NMR (101 MHz, DMSO-d$_6$) δ 158.9 (C), 146.4 (C), 139.4 (CH), 135.8 (C), 132.6 (C), 131.9 (CH), 129.5 (C), 129.3 (CH), 129.23 (CH), 129.22 (2CH), 128.0 (CH), 126.9 (CH), 122.3 (C), 118.0 (CH), 113.9 (2CH); HRMS (ESI+) calcd for C$_{17}$H$_{14}$ClN$_2$O (M+H)$^+$ 297.0789, found 297.0781; HPLC purity≥98%, t$_R$=8.19 min, λ=280 nm.

3-(2-Bromophenyl)-5-(phenylamino)pyridin-2(1H)-one (69)

Compound 69 was prepared according to general procedure C, starting from impure compound 49 (65 mg). The mixture was stirred for 3 h and was quenched with NEt$_3$ (13 eq.) and MeOH (7 eq.). After work-up, the crude was purified by column chromatography (SiO$_2$, EtOAc/cyclohexane 7:3 to EtOAc). The product was washed with CH$_2$Cl$_2$ to give 69 (18.6 mg, 0.055 mmol, 18% over 2 steps from 29) as a white solid.

R$_f$=0.32 (EtOAc); Mp>236° C. (decomposition); IR (ATR) 3272, 1596, 744 cm$^{-1}$; $^1$H NMR (400 MHz, DMSO-d$_6$) δ 11.63 (br s, 1H), 7.67 (d, J=7.9, 1 H), 7.52 (s, 1H), 7.44-7.34 (m, 2H), 7.32-7.22 (m, 3H), 7.14 (t, J=7.6, 2H), 6.75 (d, J=7.9, 2H), 6.67 (t, J=7.1, 1H); $^{13}$C NMR (101 MHz, DMSO-d$_6$) δ 158.8 (C), 146.4 (C), 139.3 (CH), 137.8 (C), 132.4 (CH), 131.8 (CH), 131.3 (C), 129.5 (CH), 129.2 (2CH), 127.9 (CH), 127.4 (CH), 123.2 (C), 122.3 (C), 118.0 (CH), 113.9 (2CH); HRMS (ESI+) calcd for C$_{17}$H$_{14}$BrN$_2$O (M+H)$^+$341.0284, found 341.0281; HPLC purity≥95%, t$_R$=8.24 min, λ=280 nm.

Ethyl 2-(2-oxo-5-(phenylamino)-1,2-dihydropyridin-3-yl)benzoate (70)

Compound 70 was prepared according to general procedure C, starting from 50 (83.2 mg, 0.196 mmol). The mixture was stirred for 3 h and was quenched with NEt$_3$ (15 eq.) and MeOH (6 eq.). The crude was purified by column chromatography (SiO$_2$, EtOAc/cyclohexane 5:5 to AcOEt) to give 70 (51.4 mg, 0.154 mmol, 78%) as a brown powder.

R$_f$=0.28 (EtOAc); Mp>83° C. (decomposition); IR (ATR) 3450-3150, 1705, 1595, 1495, 1283, 1250, 748, 693 cm$^{-1}$; $^1$H NMR (400 MHz, DMSO-d$_6$) δ 11.54 (br s, 1H), 7.75 (dd, J=7.5, 1.5, 1H), 7.59 (td, J=7.5, 1.4, 1H), 7.51 (s, 1H), 7.45 (td, J=7.6, 1.3, 1H), 7.35-7.32 (m, 2H), 7.19-7.5 (br s, 1H), 7.14 (dd, J=8.6, 7.3, 2H), 6.74 (dd, J=8.6, 1.1, 2H), 6.67 (tt, J=7.3, 1.0, 1H), 4.10 (q, J=7.1, 2H), 1.13 (t, J=7.1, 3H); $^{13}$C NMR (101 MHz, DMSO-d$_6$) δ 167.1 (C), 159.7 (C), 146.6 (C), 136.9 (CH), 136.8 (C), 133.0 (C), 131.8 (CH), 131.7 (C), 130.5 (CH), 129.2 (2CH), 128.9 (CH), 127.7 (CH), 126.7 (CH), 122.5 (C), 117.9 (CH), 113.7 (2CH), 60.3 (CH$_2$), 13.8 (CH$_3$); HRMS (ESI+) calcd for C$_{20}$H$_{19}$N$_2$O$_3$ (M+H)+335.1390, found 335.1397; HPLC purity≥95%, t$_R$=8.13 min, λ=272 nm.

2-(2-Oxo-5-(phenylamino)-1,2-dihydropyridin-3-yl)benzamide (71)

Compound 71 was prepared according to general procedure C, starting from impure compound 51 (76.6 mg). The mixture was stirred for 5 h 30 min and was quenched with NEt$_3$ (10 eq.) and MeOH (6 eq.). After work-up, the crude was purified by column chromatography (SiO$_2$, EtOAc/MeOH 95:5 to 85:15) to give 71 (24.6 mg, 0.081 mmol, 32% over 2 steps from 31) as a yellow powder.

R$_f$=0.29 (EtOAc/MeOH 85:15); Mp>226° C. (decomposition); IR (ATR) 3500-3000, 1657, 1596, 1494, 746, 691 cm$^{-1}$; $^1$H NMR (400 MHz, DMSO-d$_6$) δ 11.41 (br s, 1H), 7.65 (br s, 1H), 7.50-7.47 (m, 2H), 7.43 (td, J=7.5, 1.5, 1 H), 7.36 (td, J=7.5, 1.4, 1 H), 7.36-7.33 (m, 1H), 7.26 (d, J=2.9, 1H), 7.15 (dd, J=8.5, 7.3, 2H), 7.11 (br s, 2H), 6.75 (dd, J=8.6, 1.0, 2H), 6.66 (tt, J=7.3, 1.1, 1H); $^{13}$C NMR (101 MHz, DMSO-d$_6$) δ 170.4 (C), 159.5 (C), 146.4 (C), 137.4 (CH), 137.2 (C), 135.3 (C), 132.0 (C), 130.6 (CH), 129.2 (2CH), 129.1 (CH), 127.4 (CH), 127.2 (CH), 126.2 (CH), 122.4 (C), 117.8 (CH), 113.8 (2CH); HRMS (ESI+) calcd for C$_{18}$H$_{16}$N$_3$O$_2$ (M+H)$^+$306.1237, found 306.1233; HPLC purity≥94%, t$_R$=6.88 min, λ=294 nm.

3-(2-Nitrophenyl)-5-(phenylamino)pyridin-2(1H)-one (72)

Compound 72 was prepared according to general procedure C, starting from 52 (80.5 mg, 0.203 mmol). The mixture was stirred for 4 h and was quenched with NEt$_3$ (18 eq.) and MeOH (6 eq.). After work-up, the crude was purified by column chromatography (SiO$_2$, EtOAc/cyclohexane 3:7 to 5:5) to give 72 (55.6 mg, 0.181 mmol, 89%) as a red powder. R$_f$=0.58 (Acetone/cyclohexane 5:5); Mp>224° C. (decomposition); IR (ATR) 3375, 1658, 1597, 1519, 1488, 1465, 1336, 741, 695 cm$^{-1}$; $^1$H NMR (400 MHz, DMSO-d$_6$) δ 11.63 (br s, 1H), 7.98 (dd, J=8.1, 1.3, 1H), 7.75 (td, J=7.6, 1.3, 1H), 7.60 (ddd, J=8.1, 7.5, 1.4, 1H), 7.56 (br s, 1H), 7.55 (d, J=2.9, 1H), 7.51 (dd, J=7.6, 1.5, 1H), 7.23 (br s, 1H), 7.16 (dd, J=8.5, 7.3, 2H), 6.77 (dd, J=8.6, 1.0, 2H), 6.69 (tt, J=7.3, 1.1, 1H); $^{13}$C NMR (101 MHz, DMSO-d$_6$) δ 158.6 (C), 148.9 (C), 146.3 (C), 137.7 (CH), 133.5 (CH), 132.1 (CH), 131.0 (C), 129.7 (C), 129.3 (2CH), 129.1 (CH), 127.4 (CH), 123.9 (CH), 122.6 (C), 118.0 (CH), 133.9 (2CH); HRMS (ESI+) calcd for C$_{17}$H$_{14}$N$_3$O$_3$ (M+H)$^+$ 308.1030, found 308.1030; HPLC purity≥97%, t$_R$=8.07 min, λ=276 nm.

3-([1,1-biphenyl]-4-yl)-5-(phenylamino)pyridin-2(1H)-one (73)

Compound 73 was prepared according to general procedure C, starting from 53 (77.6 mg, 0.181 mmol) and the corresponding boronic acid. The mixture was stirred for 3 h and was quenched with NEt$_3$ (14 eq.) and MeOH (7 eq.). After evaporation, EtOAc was added. A precipitate appeared in the organic phase and was filtered and washed with EtOAc and CH$_2$Cl$_2$ to give 73 (48.8 mg, 0.144 mmol, 80%) was obtained as a beige solid. R$_f$=0.09 (EtOAc/cyclohexane 5:5); Mp>245° C. (decomposition); IR (ATR) 3412, 1599, 749, 691 cm$^{-1}$; $^1$H NMR (400 MHz, DMSO-d$_6$) δ 11.67 (br s, 1H), 7.85 (d, J=7.8, 2H), 7.73-7.66 (m, 4H), 7.60 (s, 1H), 7.52 (s, 1H), 7.48 (t, J=7.3, 2H), 7.37 (t, J=6.8, 1H), 7.21 (s, 1H), 7.15 (t, J=7.5, 2H), 6.76 (d, J=7.8, 2H), 6.68 (t, J=7.2, 1H); $^{13}$C NMR (101 MHz, DMSO-d$_6$) δ 159.5 (C), 146.5 (C), 139.8 (C), 139.1 (C), 137.4 (CH), 135.6 (C), 129.4 (C), 129.2 (2CH), 129.0 (2CH), 128.7 (2CH), 127.5 (CH), 127.1 (CH), 126.6 (2CH), 126.2 (2CH), 122.8 (C), 117.9 (CH), 113.8 (2CH); HRMS (ESI+) calcd for C$_{23}$H$_{16}$N$_2$O (M+H)$^+$ 339.1492, found 339.1487; HPLC purity≥97%, t$_R$=9.16 min, λ=284 nm.

3-(3-Chlorophenyl)-5-(phenylamino)pyridin-2(1H)-one (74)

Compound 74 was prepared according to general procedure C, starting from 54 (78.8 mg, 0.204 mmol). The mixture was stirred for 2 h 40 min and was quenched with NEt$_3$ (10 eq.) and MeOH (6 eq.). The crude was purified by column chromatography (SiO$_2$, EtOAc/cyclohexane 5:5 to 7:3) to give 74 (55.4 mg, 0.187 mmol, 92%) as a yellow-brown powder.

R$_f$=0.34 (EtOAc/cyclohexane 7:3); Mp>187° C. (decomposition); IR (ATR) 3275, 1596, 1547, 1449, 1350, 1286, 746, 703, 683 cm$^{-1}$; $^1$H NMR (400 MHz, DMSO-d$_6$) δ 11.75 (br s, 1H), 7.89 (t, J=1.7, 1 H), 7.66 (dt, J=7.4, 1.6, 1 H), 7.62 (d, J=2.9, 1 H), 7.51 (s, 1H), 7.41 (t, J=7.7, 1H), 7.37 (ddd, J=8.0, 2.0, 1.5, 1H), 7.23 (dd, J=2.9, 1H), 7.15 (dd, J=8.6, 7.3, 2H), 6.75 (dd, J=8.6, 1.1, 2H), 6.68 (tt, J=7.3, 1.1, 1H); $^{13}$C NMR (101 MHz, DMSO-d$_6$) δ 159.3 (C), 146.4 (C), 138.5 (C), 138.2 (CH), 132.6 (C), 129.9 (CH), 129.2 (2CH), 128.1 (C), 127.9 (CH), 127.8 (CH), 127.3 (CH), 126.6 (CH), 122.8 (C), 118.0 (CH), 113.8 (2CH); HRMS (ESI+) calcd for C$_{17}$H$_{14}$ClN$_2$O (M+H)$^+$297.0789, found 297.0796; HPLC purity≥99%, t$_R$=8.59 min, λ=284 nm.

3-(3-Acetylphenyl)-5-(phenylamino)pyridin-2(1H)-one (75)

To a solution under argon of 55 (46 mg, 0.117 mg, 1 eq.) in anhydrous CH$_2$Cl$_2$ (0.75 mL) was added dropwise iodotrimethylsilane (20 μL, 0.141 mmol, 1.2 eq.). The mixture was stirred at room temperature overnight. Due to the presence of residual starting material 55, additional iodotrimethylsilane (10 μL, 0.07 mmol, 0.6 eq.) was added and the mixture was stirred for 2 h. The reaction was quenched by addition of NEt$_3$ (0.05 mL) and MeOH (0.75 mL) and the mixture was concentrated. Ethyl acetate was added and the organic phase was washed with water, dried over MgSO$_4$ and filtered. After evaporation under reduced pressure, the crude was purified by column chromatography (SiO$_2$, acetone/cyclohexane 4:6 to 45:55) to give 75 (25 mg, 0.082 mmol, 70%) a yellow powder. R$_f$=0.53 (acetone/cyclohexane 6:4); Mp>188° C. (decomposition); IR (ATR) 3310, 1673, 1621, 1599, 1243, 752, 697 cm$^{-1}$; $^1$H NMR (400 MHz, DMSO-d$_6$) δ 11.74 (br s, 1H), 8.28 (t, J=1.8, 1H), 8.00 (ddd, J=7.8, 1.8, 1.2, 1H), 7.91 (ddd, J=7.8, 1.8, 1.2, 1H), 7.63 (d, J=3.0, 1H), 7.54 (t, J=7.8, 1H), 7.53 (s, 1H), 7.24 (d, J=2.8, 1H), 7.15 (dd, J=8.6, 7.3, 2H), 6.75 (dd, J=8.7, 1.1, 2H), 6.68 (tt, J=7.3, 1.1, 1H), 2.60 (s, 3H); $^{13}$C NMR (101 MHz, DMSO-d$_6$) δ 197.9 (C), 159.4 (C), 146.5 (C), 138.1 (CH), 136.8 (C), 136.6 (C), 132.9 (CH), 129.3 (2CH), 129.0 (C), 128.4 (CH), 127.9 (CH), 127.6 (CH), 127.3 (CH), 122.9 (C), 118.0 (CH), 113.8 (2CH), 26.9 (CH$_3$); HRMS (ESI+) calcd for C$_{13}$H$_{17}$N$_2$O$_2$ (M+H)$^+$305.1285, found 305.1277; HPLC purity≥98%, t$_R$=7.99 min, λ=282 nm.

3-(4-Hydroxyphenyl)-5-(phenylamino)pyridin-2(1H)-one (76)

Compound 76 was prepared according to general procedure C, starting from 56 (90 mg, 0.24 mmol). The mixture was stirred for 2 h and was quenched with NEt$_3$ (27 eq.) and MeOH (9 eq.). After evaporation, EtOAc was added. The mixture was washed with water and brine. The organic phase was dried over MgSO$_4$, filtered and evaporated. The crude was purified by column chromatography (SiO$_2$, EtOAc) to give 76 (62 mg, 0.22 mmol, 91%) as a yellow solid.

R$_f$=0.29 (EtOAc); Mp>238° C. (decomposition); IR (ATR) 3415, 3374, 1598, 1513, 1495, 1173, 1163, 862, 834, 750 cm$^{-1}$; $^1$H NMR (400 MHz, DMSO-d$_6$) δ 11.50 (br s, 1H), 9.51 (s, 1H), 7.57 (d, J=8.8, 2H), 7.46 (s, 1H), 7.42 (d, J=2.9, 1H), 7.14 (dd, J=8.5, 7.3, 2H), 7.11 (d, J=2.9, 1H), 6.76 (d, J=8.8, 2H), 6.73 (dd, J=8.6, 1.0, 2H), 6.67 (tt, J=7.3, 1.0, 1H); $^{13}$C NMR (101 MHz, DMSO-d$_6$) δ 159.7 (C), 157.0 (C), 146.6 (C), 136.0 (CH), 130.0 (C), 129.4 (2CH), 129.2 (2CH), 127.2 (C), 125.8 (CH), 122.7 (C), 117.8 (CH), 114.7 (2CH), 113.8 (2CH); HRMS (ESI+) calcd for C$_{17}$H$_{15}$N$_2$O$_2$ (M+H)$^+$279.1128, found 279.1132; HPLC purity≥97%, t$_R$=7.34 min, λ=284 nm.

5-(Phenylamino)-3-(p-tolyl)pyridin-2(1H)-one (77)

Compound 77 was prepared according to general procedure C, starting from 57 (80.3 mg, 0.219 mmol). The mixture was stirred for 3 h and was quenched with NEt$_3$ (13 eq.) and MeOH (6 eq.). After evaporation, EtOAc was added. The mixture was washed with water and brine. The organic phase was dried over MgSO$_4$, filtered and evaporated. The crude was purified by column chromatography (SiO$_2$, EtOAc/cyclohexane 5:5 to EtOAc/cyclohexane 8:2) to give 77 (58.3 mg, 0.211 mmol, 96%) as a yellow powder. R$_f$=0.17 (EtOAc/cyclohexane 7:3); Mp>195° C. (decomposition); IR (ATR) 3290, 1586, 1550, 818, 797, 744, 622 cm$^{-1}$; $^1$H NMR (400 MHz, DMSO-d$_6$) δ 11.59 (br s, 1H), 7.62 (d, J=8.2, 2H), 7.49 (s, 1H), 7.48 (d, J=2.8, 1H), 7.21-7.11 (m, 5H), 6.74 (dd, J=8.6, 1.0, 2H), 6.67 (tt, J=7.3, 1.1, 1H), 2.31 (s, 3H); $^{13}$C NMR (101 MHz, DMSO-d$_6$) δ 159.6 (C), 146.5 (C), 137.0 (CH), 136.8 (C), 133.6 (C), 129.9 (C), 129.2 (2CH), 128.5 (2CH), 128.0 (2CH), 126.7 (CH), 122.8 (C), 117.9 (CH), 113.80 (2CH), 20.8 (CH$_3$); HRMS (ESI+) calcd for C$_{18}$H$_{17}$N$_2$O (M+H)$^+$277.1335, found 277.1338; HPLC purity≥97%, t$_R$=8.46 min, λ=284 nm.

5-(Phenylamino)-3-(4-(trifluoromethyl)phenyl)pyridin-2(1H)-one (78)

Compound 78 was prepared according to general procedure C, starting from 58 (110 mg, 0.26 mmol). The mixture was stirred for 2 h and was quenched with NEt$_3$ (27 eq.) and MeOH (9 eq.). After work-up, the crude was purified by column chromatography (SiO$_2$, EtOAc/cyclohexane 8:2) to give 78 (82 mg, 0.25 mmol, 95%) as a yellow solid.

R$_f$=0.45 (EtOAc/cyclohexane 8:2); Mp>229° C. (decomposition); IR (ATR) 3292, 1595, 1550, 1455, 1318, 1167, 1123, 1111, 1068, 834, 750 cm$^{-1}$; $^1$H NMR (400 MHz, DMSO-d$_6$) δ 11.77 (br s, 1H), 7.98 (d, J=8.1, 2H), 7.73 (d, J=8.3, 2H), 7.66 (d, J=2.9, 1 H), 7.52 (br s, 1H), 7.27 (d, J=2.9, 1 H), 7.15 (dd, J=8.6, 7.3, 2H), 6.76 (dd, J=8.6, 1.0, 2H), 6.69 (tt, J=7.3, 1.0, 1H); $^{13}$C NMR (101 MHz, DMSO-d$_6$) δ 159.3 (C), 146.4 (C), 140.5 (C), 138.6 (CH), 129.2 (2CH), 128.8 (2CH), 128.3 (CH), 128.1 (C), 127.6 (q, J$_{CF}$=32, C), 124.8 (q, J$_{CF}$=4, 2CH), 124.3 (q, J$_{CF}$=272, C), 122.9 (C), 118.0 (CH), 113.8 (2CH); HRMS (ESI+) calcd for C$_{18}$H$_{14}$F$_3$N$_2$O (M+H)$^+$331.1053, found 331.1042; HPLC purity≥97%, t$_R$=8.73 min, λ=284 nm.

5-(Phenylamino)-3-(4-(trifluoromethoxy)phenyl)pyridin-2(1H)-one (79)

Compound 79 was prepared according to general procedure C, starting from 59 (68 mg, 0.156 mmol). The mixture was stirred for 3 h 40 min and was quenched with NEt$_3$ (14 eq.) and MeOH (8 eq.). After work-up, the crude was purified by column chromatography (SiO$_2$, EtOAc/cyclohexane 8:2) to give 79 (49.2 mg, 0.142 mmol, 91%) as a yellow solid. R$_f$=0.55 (EtOAc); Mp>210° C. (decomposition); IR (ATR) 3282, 1595, 1549, 1454, 1208, 1152, 910, 806, 744 cm$^{-1}$; $^1$H NMR (400 MHz, DMSO-d$_6$) δ 11.74 (br s, 1H), 7.87 (d, J=8.9, 2H), 7.59 (d, J=2.9, 1 H), 7.51 (s, 1H), 7.37 (d, J=8.4, 2H), 7.22 (d, J=2.8, 1 H), 7.14 (dd, J=8.5, 7.4, 2H), 6.75 (dd, J=8.6, 1.0, 2H), 6.68 (tt, J=7.3, 1.0, 1H); $^{13}$C NMR (101 MHz, DMSO-d$_6$) δ 159.4 (C), 147.5 (q, J=2, C), 146.5 (C), 138.0 (CH), 135.7 (C), 130.1 (2CH), 129.2 (2CH), 128.4 (C), 127.7 (CH), 122.8 (C), 120.5 (2CH), 120.1 (q, J=256, C), 118.0 (CH), 113.8 (2CH); HRMS (ESI+) calcd for C$_{18}$H$_{14}$F$_3$N$_2$O$_2$ (M+H)$^+$347.1002, found 347.1002; HPLC purity≥97%, t$_R$=8.80 min, λ=284 nm.

Methyl 4-(2-oxo-5-(phenylamino)-1,2-dihydropyridin-3-yl)benzoate (80)

Compound 80 was prepared according to general procedure C, starting from 60 (51.4 mg, 0.125 mmol). The mixture was stirred for 5 h 20 min and was quenched with NEt$_3$ (29 eq.) and MeOH (10 eq.). After work-up, the crude was purified by column chromatography (SiO$_2$, EtOAc/cyclohexane 9:1 to AcOEt) to give 80 (36.3 mg, 0.113 mmol, 90%) as a yellow-brown solid.

R$_f$=0.31 (EtOAc); Mp>230° C. (decomposition); IR (ATR) 3375, 1694, 1593, 1274, 1106, 746, 706, 689 cm$^{-1}$; $^1$H NMR (400 MHz, DMSO-d$_6$) δ 11.79 (br s, 1H), 7.96 (d, J=8.5, 2H), 7.91 (d, J=8.5, 2H), 7.65 (d, J=2.9, 1H), 7.53 (s, 1H), 7.26 (d, J=2.9, 1H), 7.15 (dd, J=8.6, 7.3, 2H), 6.75 (dd, J=8.6, 1.1, 2H), 6.68 (tt, J=7.3, 1.1, 1H), 3.86 (s, 3H); $^{13}$C NMR (101 MHz, DMSO-d$_6$) δ 166.1 (C), 159.3 (C), 146.5 (C), 141.2 (C), 138.6 (CH), 129.3 (2CH), 128.9 (2CH), 128.5 (C), 128.34 (3CH), 128.27 (C), 122.9 (C), 118.0 (CH), 113.8 (2CH), 52.2 (CH$_2$); HRMS (ESI+) calcd for C$_{19}$H$_{17}$N$_2$O$_3$ (M+H)$^+$321.1234, found 321.1230; HPLC purity≥97%, t$_R$=8.22 min, λ=284 nm.

4-(2-Oxo-5-(phenylamino)-1,2-dihydropyridin-3-yl)benzamide (81)

Compound 81 was prepared according to general procedure C, starting from impure compound 61 (101 mg). The mixture was stirred for 23 h and was quenched with NEt$_3$ (14 eq.) and MeOH (5 eq.). After work-up, the crude was purified by column chromatography (SiO$_2$, acetone/cyclohexane 5:5 to acetone) to give 81 (55.3 mg, 0.181 mmol, 74% over 2 steps from 41) as a yellow-brown solid.

R$_f$=0.14 (acetone/cyclohexane 5:5); Mp>222° C. (decomposition); IR (ATR) 3421, 3272, 3252, 3162, 1664, 1596, 1393, 846, 758, 698 cm$^{-1}$; $^1$H NMR (400 MHz, DMSO-d$_6$) δ 11.73 (br s, 1H), 7.98 (br s, 1H), 7.88 (d, J=8.5, 2H), 7.81 (d, J=8.5, 2H), 7.61 (d, J=2.9, 1 H), 7.52 (s, 1H), 7.36 (br s, 1H), 7.23 (br s, 1H), 7.15 (dd, J=8.5, 7.4, 2H), 6.75 (d, J=8.0, 2H), 6.68 (t, J=7.3, 1H); $^{13}$C NMR (101 MHz, DMSO-d$_6$) δ 167.6 (C), 159.4 (C), 146.5 (C), 139.2 (C), 138.1 (CH), 133.0 (C), 129.3 (2CH), 129.0 (C), 127.9 (2CH), 127.8 (CH), 127.2 (2CH), 122.9 (C), 118.0 (CH), 113.8 (2CH); HRMS (ESI+) calcd for C$_{18}$H$_{16}$N$_3$O$_2$ (M+H)$^+$306.1237, found 306.1232; HPLC purity≥96%, t$_R$=6.97 min, λ=284 nm.

3-(2,4-Difluorophenyl)-5-(phenylamino)pyridin-2(1H)-one (82)

Compound 82 was prepared according to general procedure C, starting from impure compound 62 (65 mg). The mixture was stirred for 2 h 30 min and was quenched with NEt$_3$ (13 eq.) and MeOH (7 eq.). After work-up, the crude was purified by column chromatography (SiO$_2$, EtOAc/cyclohexane 5:5 to 7:3) to give 82 (39.7 mg, 0.133 mmol, 62% over 2 steps from 42) as a green powder.

R$_f$=0.25 (EtOAc/cyclohexane 7:3); Mp>202° C. (decomposition); IR (ATR) 3290, 1593, 1544, 1496, 1454, 1444, 1424, 1362, 1265, 1100, 819, 750 cm$^{-1}$; $^1$H NMR (400 MHz, DMSO-d$_6$) δ 11.71 (br s, 1H), 7.59 (dt, J=8.6, 6.8, 1 H), 7.51 (br s, 1H), 7.43 (d, J=2.9, 1H), 7.28 (ddd, J=10.6, 9.5, 2.6, 1H), 7.27-7.23 (br s, 1H), 7.14 (t, J=7.9, 2H), 7.15-7.08 (m, 1H), 6.74 (d, J=8.0, 2H), 6.68 (t, J=7.3, 1H); $^{13}$C NMR (101 MHz, DMSO-d$_6$) δ 161.8 (dd, J$_{CF}$=247, 12.5, C), 160.8 (dd, J$_{CF}$=249, 12.5, C), 158.9 (C), 146.4 (C), 139.7 (CH), 132.8 (dd, J$_{CF}$=10, 5, CH), 129.2 (2CH), 128.1 (CH), 124.8 (C), 122.4 (C), 120.8 (dd, J$_{CF}$=14.5, 4, C), 118.0 (CH), 113.8 (2CH), 111.1 (dd, J$_{CF}$=21, 3.5, CH), 104.0 (t, J$_{CF}$=26, CH); HRMS (ESI+) calcd for C$_{17}$H$_{13}$F$_2$N$_2$O (M+H)$^+$299.0991, found 299.0992; HPLC purity≥97%, t$_R$=8.19 min, λ=282 nm.

Indolyl derivatives were also prepared according to the following synthetic pathways:
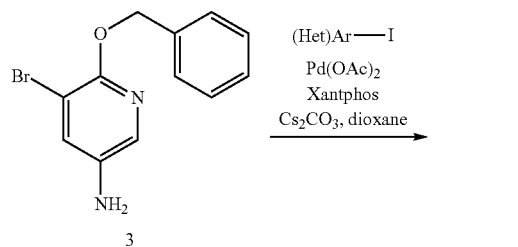
(Het)Ar =
86, 102, 118, 2-F—C$_6$H$_4$
87, 103, 119, 3-F—C$_6$H$_4$
88, 104, 120, 4-F—C$_6$H$_4$
89, 105, 121, 2-OCH$_3$—C$_6$H$_4$
90, 106, 122, 3-OCH$_3$—C$_6$H$_4$
91, 107, 123, 4-OCH$_3$—C$_6$H$_4$
92, 108, 124, 2-(CO$_2$Et)—C$_6$H$_4$
93, 109, 125, 3-(CO$_2$Et)—C$_6$H$_4$
94, 110, 126, 4-(CO$_2$Et)—C$_6$H$_4$
95, 111, 127, 2-NO$_2$—C$_6$H$_4$
96, 112, 128, 3-NO$_2$—C$_6$H$_4$
97, 113, 129, 4-NO$_2$—C$_6$H$_4$
98, 114, 130, 2-CH$_3$—C$_6$H$_4$
99, 115, 131, pyridin-2-yl
100, 116, 132, pyridin-3-yl
101, 117, 133, pyridin-4-yl
134, 3-OH—C$_6$H$_4$
135, 2-NH$_2$—C$_6$H$_4$
145, 2-OH—C$_6$H$_4$
146, 4-OH—C$_6$H$_4$
147, 3-NH$_2$—C$_6$H$_4$
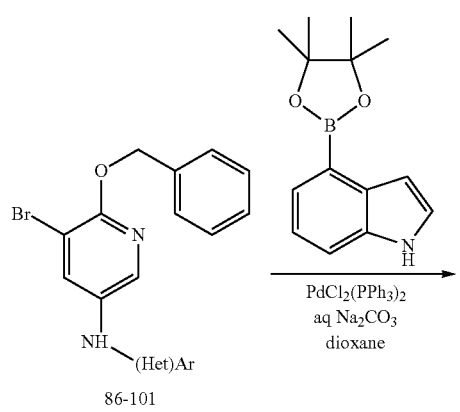
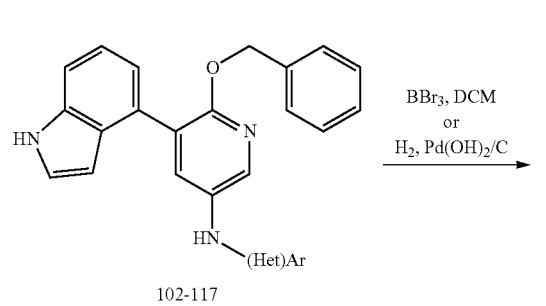
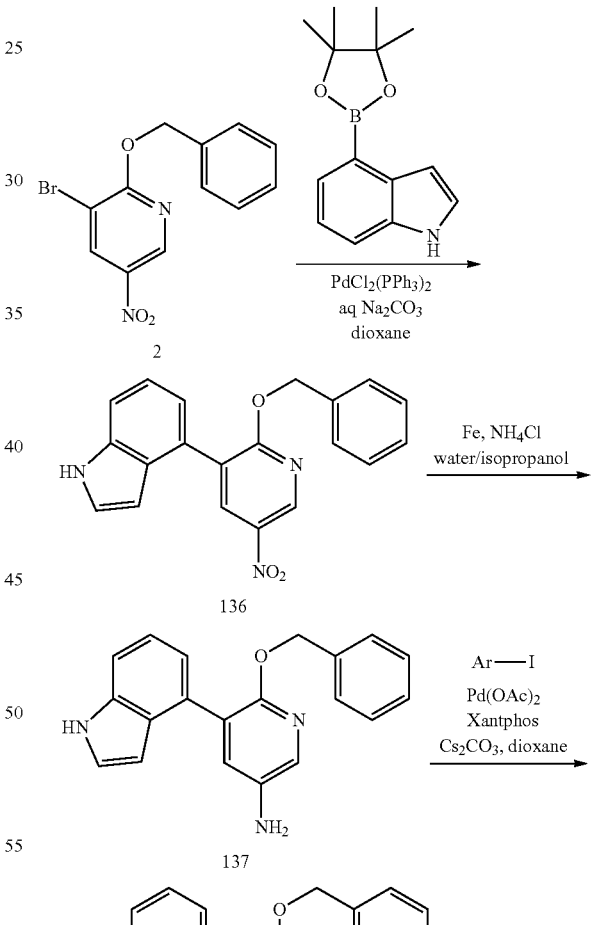

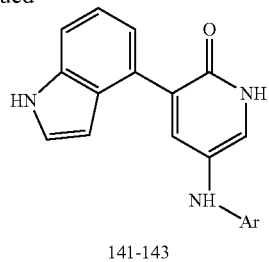

141-143

Ar =
138, 141, 2-Br—C$_6$H$_4$
139, 142, 3-Br—C$_6$H$_4$
140, 143, 4-Br—C$_6$H$_4$

General Procedure for the Preparation of Compounds 86-101 and 138-140.

Procedure D: A 5-9 mL screw-cap tube under argon was charged with compound 3 or 137 (1.6-0.2 mmol, 1 eq.), Pd(OAc)$_2$ (0.05 eq.), Xantphos (0.05 eq.) and Cs$_2$CO$_3$ (2 eq.). Then, anhydrous 1,4-dioxane (0.2 M) degassed with argon and the iodide derivative (1 eq.) were added. The tube was sealed and the mixture was stirred at 100° C. for several hours. The resulting suspension was filtered through a pad of Celite which was then washed with ethyl acetate. After evaporation of the filtrate, the brown residue was purified by column chromatography.

General Procedure for the Preparation of Compounds 121-126, 130, 132 and 135.

Procedure E: To a solution under argon of benzylated derivative (0.1-0.5 mmol, 1 eq.) in MeOH (0.3 M) degassed with argon was added 20% Pd(OH)$_2$/C (0.4 eq.). The mixture was then hydrogenated at room temperature for 6 h in the dark. The mixture was filtered through a pad of Celite and then washed with ethyl acetate. The filtrate was evaporated under reduced pressure and the obtained crude was purified by column chromatography.

6-(Benzyloxy)-5-bromo-N-(2-fluorophenyl)pyridin-3-amine (86)

Compound 86 was prepared according to general procedure D, starting from 3 (199 mg, 0.713 mmol) in 7 mL of anhydrous 1,4-dioxane. The mixture was heated for 20 h. The crude oil was purified by column chromatography (SiO$_2$, cyclohexane to EtOAc/cyclohexane 8:92) to give 86 (134 mg, 0.360 mmol, 50%) as a beige solid.

R$_f$=0.55 (EtOAc/cyclohexane 1:9); Mp 67° C.; IR (ATR) 3306, 1619, 1443, 1356, 1295, 1219, 1181, 1098, 1056, 1012, 733 cm$^{-1}$; $^1$H NMR (400 MHz, DMSO-d$_6$) δ 7.96 (s, 1H), 7.94 (d, J=2.5, 1H), 7.73 (d, J=2.5, 1H), 7.48-7.44 (m, 2H), 7.42-7.37 (m, 2H), 7.35-7.30 (m, 1H), 7.20 (ddd, J=11.9, J$_2$=8.1, 1.4, 1H), 7.14 (td, J=8.3, J$_2$=1.7, 1H), 7.06 (td, J=7.7, 1.3, 1H), 6.90 (dddd, J=8.1, 7.3, 4.9, 1.8, 1H), 5.37 (s, 2H); $^{13}$C NMR (101 MHz, DMSO-d$_6$) δ 153.5 (C), 152.8 (d, J$_{CF}$=242, C), 137.1 (C), 135.5 (CH), 135.0 (C), 133.0 (CH), 131.5 (d, J$_{CF}$=11, C), 128.4 (2CH), 127.7 (CH), 127.5 (2CH), 124.9 (d, J$_{CF}$=3, CH), 121.0 (d, J$_{CF}$=7, CH), 117.7 (d, J$_{CF}$=3, CH), 115.8 (d, J$_{CF}$=19, CH), 105.8 (C), 67.7 (CH$_2$); HRMS (ESI+) calcd for C$_{18}$H$_{15}$BrFN$_2$O(M+H)$^+$373.0346, found 373.0343.

6-(Benzyloxy)-5-bromo-N-(3-fluorophenyl)pyridin-3-amine (87)

Compound 87 was prepared according to general procedure D, starting from 3 (202 mg, 0.724 mmol). The mixture was heated for 2 h 30 min. The crude oil was purified by column chromatography (SiO$_2$, cyclohexane to EtOAc/cyclohexane 5:95) to give 87 (153 mg, 0.410 mmol, 57%) as a brown solid.

R$_f$=0.72 (EtOAc/cyclohexane 3:7); Mp 43° C.; IR (ATR) 3431, 1619, 1594, 1466, 1450, 1432, 1354, 1293, 1260, 1217, 1136, 1051, 970, 691 cm$^{-1}$; $^1$H NMR (400 MHz, DMSO-d$_6$) δ 8.34 (s, 1H), 8.01 (d, J=2.5, 1 H), 7.84 (d, J=2.5, 1 H), 7.49-7.45 (m, 2H), 7.42-7.37 (m, 2H), 7.35-7.30 (m, 1H), 7.22 (td, J=8.2, 7.0, 1 H), 6.74 (ddd, J=8.2, 2.2, 0.7, 1 H), 6.67 (dt, J=11.7, 2.3, 1 H), 6.57 (dddd, J=8.9, 8.1, 2.5, 0.9, 1 H), 5.39 (s, 2H); $^{13}$C NMR (101 MHz, DMSO-d$_6$) δ 163.2 (d, J$_{CF}$=241, C), 154.1 (C), 146.3 (d, J$_{CF}$=11, C), 137.0 (C), 136.8 (CH), 134.3 (CH), 134.2 (C), 130.9 (d, J$_{CF}$=10, CH), 128.4 (2CH), 127.8 (CH), 127.5 (2CH), 110.9 (d, J$_{CF}$=2, CH), 106.0 (C), 105.5 (d, J$_{CF}$=21, CH), 101.4 (d, J$_{CF}$=25, CH), 67.8 (CH$_2$); HRMS (ESI+) calcd for C$_{18}$H$_{15}$BrFN$_2$O (M+H)$^+$373.0346, found 373.0369.

6-(Benzyloxy)-5-bromo-N-(4-fluorophenyl)pyridin-3-amine (88)

Compound 88 was prepared according to general procedure D, starting from 3 (202 mg, 0.724 mmol). The mixture was heated for 2 h 45 min. The crude oil was purified by column chromatography (SiO$_2$, cyclohexane to EtOAc/cyclohexane 5:95) to give 88 (193.6 mg, 0.519 mmol, 72%) as a brown solid.

R$_f$=0.73 (EtOAc/cyclohexane 3:7); Mp 43° C.; IR (ATR) 3394, 1506, 1444, 1215, 1052, 825, 735 cm$^{-1}$; $^1$H NMR (400 MHz, DMSO-d$_6$) δ 8.06 (5, 1 H), 7.92 (d, J=2.5, 1 H), 7.72 (d, J=2.5, 1 H), 7.47-7.43 (m, 2H), 7.42-7.36 (m, 2H), 7.35-7.29 (m, 1H), 7.07 (t, J=8.8, 2H), 6.99 (dd, J=9.0, 4.7, 2H), 5.36 (5, 2H); $^{13}$C NMR (101 MHz, DMSO-d$_6$) δ 156.4 (d, J$_{CF}$=236, C), 153.1 (C), 140.0 (d, J$_{CF}$=2, C), 137.2 (C), 135.9 (C), 134.5 (CH), 132.0 (CH), 128.4 (2CH), 127.7 (CH), 127.5 (2CH), 117.8 (d, J$_{CF}$=8, 2CH), 115.9 (d, J$_{CF}$=22, 2CH), 106.0 (C), 67.7 (CH$_2$); HRMS (ESI+) calcd for C$_{18}$H$_{15}$BrFN$_2$O (M+H)$^+$373.0346, found 373.0349.

6-(Benzyloxy)-5-bromo-N-(2-methoxyphenyl)pyridin-3-amine (89)

Compound 89 was prepared according to general procedure D, starting from 3 (200.2 mg, 0.717 mmol) in 3.6 mL of anhydrous 1,4-dioxane. The mixture was heated for 1 h 30 min. The crude oil was purified by two column chromatographies (SiO$_2$, cyclohexane to EtOAc/cyclohexane 8:92 and SiO$_2$, cyclohexane to Et$_2$O/cyclohexane 1:9) to give 89 (232 mg, 0.602 mmol, 84%) as a beige oil.

R$_f$=0.39 (EtOAc/cyclohexane 1:9); IR (ATR) 3392, 3283, 1594, 1509, 1445, 1237, 733, 695 cm$^{-1}$; $^1$H NMR (400 MHz, DMSO-d$_6$) δ 7.93 (d, J=2.5, 1H), 7.72 (d, J=2.5, 1H), 7.48-7.43 (m, 3H), 7.41-7.36 (m, 2H), 7.35-7.29 (m, 1H), 7.03 (dd, J=7.4, 1.9, 1H), 7.00 (dd, J=7.7, 1.4, 1H), 6.90-6.81 (m, 2H), 5.35 (s, 2H), 3.81 (s, 3H); $^{13}$C NMR (101 MHz, DMSO-d$_6$) δ 152.9 (C), 149.1 (C), 137.2 (C), 135.8 (C), 135.1 (CH), 132.7 (CH), 132.3 (C), 128.4 (2CH), 127.7 (CH), 127.5 (2CH), 120.9 (CH), 120.8 (CH), 115.6 (CH), 111.5 (CH), 105.7 (C), 67.6 (CH$_2$), 55.5 (CH$_3$); HRMS (ESI+) calcd for C$_{19}$H$_{18}$BrN$_2$O$_2$ (M+H)$^+$385.0546, found 385.0551.

6-(Benzyloxy)-5-bromo-N-(3-methoxyphenyl)pyridin-3-amine (90)

Compound 90 was prepared according to general procedure D, starting from 3 (151.1 mg, 0.541 mmol) in 5 mL of anhydrous 1,4-dioxane. The mixture was heated for 1 h 30 min. The crude oil was purified by column chromatography (SiO$_2$, cyclohexane to EtOAc/cyclohexane 1:9) to give 90 (125.4 mg, 0.325 mmol, 60%) as a brown orange solid.

R$_f$=0.45 (EtOAc/cyclohexane 1:9); Mp 61° C.; IR (ATR) 3375, 1619-1583, 1493, 1438, 1356, 1278 1215, 1158, 1052, 841, 765, 744, 692 cm$^{-1}$; $^1$H NMR (400 MHz, DMSO-d$_6$) δ 8.12 (s, 1H), 7.97 (d, J=2.5, 1H), 7.79 (d, J=2.5, 1H), 7.48-7.44 (m, 2H), 7.42-7.36 (m, 2H), 7.35-7.30 (m, 1H), 7.12 (t, J=8.1, 1H), 6.54 (dd, J=8.0, 1.7, 1H), 6.47 (t, J=2.2, 1H), 6.40 (dd, J=8.1, 2.2, 1H), 5.39 (s, 2H), 3.70 (s, 3H); $^{13}$C NMR (101 MHz, DMSO-d$_6$) δ 160.4 (C), 153.4 (C), 145.1 (C), 137.1 (C), 135.7 (CH), 135.2 (C), 133.2 (CH), 130.2 (CH), 128.4 (2CH), 127.8 (CH), 127.5 (2CH), 108.0 (CH), 105.9 (C), 105.2 (CH), 101.3 (CH), 67.8 (CH$_2$), 54.9 (CH$_3$); HRMS (ESI+) calcd for C$_{19}$H$_{18}$BrN$_2$O$_2$ (M+H)$^+$385.0546, found 385.0548.

6-(Benzyloxy)-5-bromo-N-(4-methoxyphenyl)pyridin-3-amine (91)

Compound 91 was prepared according to general procedure D, starting from 3 (200.7 mg, 0.719 mmol) in 3.6 mL of anhydrous 1,4-dioxane. The mixture was heated for 20 h. The crude oil was purified by column chromatography (SiO$_2$, cyclohexane to EtOAc/cyclohexane 1:9) to give 91 (190.9 mg, 0.496 mmol, 69%) as a beige solid.

R$_f$=0.20 (cyclohexane/EtOAc 9:1); Mp 86° C.; IR (ATR) 3390, 1508, 1437, 1360, 1242, 1052, 1020, 727, 693 cm$^{-1}$; $^1$H NMR (400 MHz, DMSO-d$_6$) δ 7.84 (br s, 1H), 7.83 (d, J=2.5, 1H), 7.60 (d, J=2.5, 1H), 7.46-7.43 (m, 2H), 7.41-7.36 (m, 2H), 7.34-7.29 (m, 1H), 6.98 (d, J=9.0, 2H), 6.87 (d, J=9.0, 2H), 5.33 (s, 2H), 3.71 (s, 3H); $^{13}$C NMR (101 MHz, DMSO-d$_6$) δ 154.0 (C), 152.2 (C), 137.4 (C), 137.3 (C), 136.1 (C), 132.7 (CH), 130.1 (CH), 128.4 (2CH), 127.7 (CH), 127.5 (2CH), 119.5 (2CH), 114.8 (2CH), 106.0 (C), 67.6 (CH$_2$), 55.2 (CH$_3$); HRMS (ESL) calcd for C$_{19}$H$_{18}$BrN$_2$O$_2$ (M+H)$^+$385.0546, found 385.0557.

Ethyl 2-((6-(benzyloxy)-5-bromopyridin-3-yl)amino)benzoate (92)

Compound 92 was prepared according to general procedure D, starting from 3 (50.1 mg, 0.179 mmol). The mixture was heated for 1 h 30 min. The crude oil was purified by column chromatography (SiO$_2$, cyclohexane to EtOAc/cyclohexane 3:97) to give 92 (69.0 mg, 0.161 mmol, 90%) as a white solid.

R$_f$=0.68 (EtOAc/cyclohexane 1:9); Mp 90° C.; IR (ATR) 3281, 1668, 1584, 1517, 1431, 1361, 1243, 1225, 736, 697 cm$^{-1}$; $^1$H NMR (400 MHz, DMSO-d$_6$) δ 9.15 (s, 1H), 8.13 (d, J=2.4, 1H), 8.04 (d, J=2.4, 1H), 7.90 (dd, J=8.0, 1.6, 1H), 7.50-7.46 (m, 2H), 7.43-7.37 (m, 3H), 7.36-7.31 (m, 1H), 6.93 (dd, J=8.5, 1.0, 1H), 6.81 (ddd, J=8.1, 7.1, 1.1, 1H), 5.43 (s, 2H), 4.32 (q, J=7.1, 2H), 1.33 (t, J=7.1, 3H); $^{13}$C NMR (101 MHz, DMSO-d$_6$) δ 167.5 (C=O), 155.7 (C), 147.6 (C), 140.9 (CH), 138.3 (CH), 136.9 (C), 134.6 (CH), 132.2 (C), 131.3 (CH), 128.4 (2CH), 127.8 (CH), 127.5 (2CH), 117.7 (CH), 113.6 (CH), 112.0 (C), 106.0 (CH), 68.0 (CH$_2$), 60.6 (CH$_2$), 14.1 (CH$_3$); HRMS (ESI+) calcd for C$_{21}$H$_{20}$BrN$_2$O$_3$ (M+H)$^+$427.0652, found 427.0654.

Ethyl 3-((6-(benzyloxy)-5-bromopyridin-3-yl)amino)benzoate (93)

Compound 93 was prepared according to general procedure D, starting from 3 (199 mg, 0.713 mmol). The mixture was heated for 1 h 45 min. The crude oil was purified by column chromatography (SiO$_2$, cyclohexane to EtOAc/cyclohexane 1:9) to give 93 (252.6 mg, 0.591 mmol, 83%) as a brown solid.

R$_f$=0.19 (EtOAc/cyclohexane 1:9); Mp 99° C.; IR (ATR) 3378, 3336, 1694, 1450, 1358, 1304, 1276, 1052, 739 cm$^{-1}$; $^1$H NMR (400 MHz, DMSO-d$_6$) δ 8.38 (s, 1H), 8.02 (d, J=2.5, 1H), 7.84 (d, J=2.5, 1H), 7.52-7.50 (m, 1H), 7.49-7.46 (m, 2H), 7.43-7.31 (m, 5H), 7.21 (ddd, J=7.6, 2.5, 1.6, 1H), 5.40 (s, 2H), 4.29 (q, J=7.1, 2H), 1.31 (t, J=7.1, 3H); $^{13}$C NMR (101 MHz, DMSO-d$_6$) δ 165.8 (C=O), 153.9 (C), 144.5 (C), 137.1 (C), 136.3 (CH), 134.5 (C), 133.9 (CH), 130.9 (C), 129.8 (CH), 128.4 (2CH), 127.7 (CH), 127.5 (2CH), 119.9 (CH), 119.3 (CH), 115.4 (CH), 106.0 (C), 67.8 (CH$_2$), 60.7 (CH$_2$), 14.1 (CH$_3$); HRMS (ESI+) calcd for C$_{21}$H$_{20}$BrN$_2$O$_3$ (M+H)$^+$427.0652, found 427.0652.

Ethyl 4-((6-(benzyloxy)-5-bromopyridin-3-yl)amino)benzoate (94)

Compound 94 was prepared according to general procedure D, starting from 3 (200.8 mg, 0.719 mmol). The mixture was heated for 2 h 15 min. The crude oil was purified by column chromatography (SiO$_2$, cyclohexane to EtOAc/cyclohexane 1:9) to give 94 (201.9 mg, 0.473 mmol, 66%) as a white solid.

R$_f$=0.16 (EtOAc/cyclohexane 1:9); Mp 139° C.; IR (ATR) 3316, 1677, 1595, 1464, 1367, 1285, 1244, 1176, 1054, 1008, 767, 730, 696 cm$^{-1}$; $^1$H NMR (400 MHz, DMSO-d$_6$) δ 8.71 (s, 1H), 8.08 (d, J=2.5, 1H), 7.91 (d, J=2.5, 1H), 7.80 (d, J=8.8, 2H), 7.49-7.45 (m, 2H), 7.43-7.38 (m, 2H), 7.36-7.31 (m, 1H), 6.94 (d, J=8.9, 2H), 5.40 (s, 2H), 4.24 (q, J=7.1, 2H), 1.28 (t, J=7.1, 3H); $^{13}$C NMR (101 MHz, DMSO-d$_6$) δ 165.5 (C=O), 154.7 (C), 148.9 (C), 138.0 (CH), 137.0 (C), 135.5 (CH), 133.1 (C), 131.2 (2CH), 128.4 (2CH), 127.8 (CH), 127.6 (2CH), 119.6 (C), 113.4 (2CH), 106.1 (C), 67.9 (CH$_2$), 60.0 (CH$_2$), 14.3 (CH$_3$); HRMS (ESI+) calcd for C$_{21}$H$_{20}$BrN$_2$O$_3$ (M+H)$^+$427.0652, found 427.0662.

6-(Benzyloxy)-5-bromo-N-(2-nitrophenyl)pyridin-3-amine (95)

Compound 95 was prepared according to general procedure D, starting from 3 (200.9 mg, 0.720 mmol) in 3.6 mL of anhydrous 1,4-dioxane. The mixture was heated for 2 h 30 min. The crude oil was purified by column chromatography (SiO$_2$, cyclohexane to EtOAc/cyclohexane 7:97) to give 95 (249.1 mg, 0.622 mmol, 86%) as an orange solid.

R$_f$=0.78 (cyclohexane/EtOAc 7:3); Mp 106° C.; IR (ATR) 3340, 1616, 1571, 1498, 1471, 1439, 1350, 1256, 1149, 1056, 1023, 732 cm$^{-1}$; $^1$H NMR (400 MHz, DMSO-d$_6$) δ 9.32 (s, 1H), 8.18 (d, J=2.4, 1H), 8.14-8.10 (m, 2H), 7.53-7.47 (m, 3H), 7.44-7.38 (m, 2H), 7.37-7.32 (m, 1H), 6.99 (dd, J=8.7, 1.1, 1H), 6.88 (ddd, J=8.4, 7.0, 1.2, 1H), 5.45 (s, 2H); $^{13}$C NMR (101 MHz, DMSO-d$_6$) δ 156.5 (C), 142.8 (C), 142.7 (CH), 140.0 (CH), 136.8 (C), 136.2 (C), 133.2 (C), 131.0 (C), 128.4 (2CH), 127.9 (CH), 127.6 (2CH), 126.1 (CH), 118.0 (CH), 116.4 (CH), 105.9 (C), 68.1 (CH$_2$); HRMS (ESI+) calcd for C$_{18}$H$_{15}$BrN$_3$O$_3$ (M+H)$^+$ 400.0291, found 400.0291.

6-(Benzyloxy)-5-bromo-N-(3-nitrophenyl)pyridin-3-amine (96)

Compound 96 was prepared according to general procedure D, starting from 3 (168.7 mg, 0.604 mmol) in 3 mL of anhydrous 1,4-dioxane. The mixture was heated for 3 h. The crude oil was purified by column chromatography (SiO$_2$, EtOAc/cyclohexane 1:9 to 17:83) to give 96 (184.2 mg, 0.460 mmol, 76%) as an orange solid.

R$_f$=0.58 (cyclohexane/EtOAc 7:3); Mp 105° C.; IR (ATR) 3387, 1519, 1448, 1340, 1235, 1052, 976, 845, 743, 730, 691, 667 cm$^{-1}$; $^1$H NMR (400 MHz, DMSO-d$_6$) δ 8.65 (s, 1H), 8.08 (d, J=2.5, 1H), 7.93 (d, J=2.5, 1H), 7.64 (t, J=2.2, 1H), 7.59 (ddd, J=8.1, 2.2, 0.9, 1H), 7.49-7.38 (m, 5H), 7.36-7.31 (m, 1H) 7.31 (ddd, J=8.3, 2.4, 0.9, 1H), 5.41 (s, 2H); $^{13}$C NMR (101 MHz, DMSO-d$_6$) δ 154.7 (C), 148.8 (C), 145.9 (C), 137.8 (CH), 137.0 (C), 135.3 (CH), 133.3 (C), 130.6 (CH), 128.4 (2CH), 127.8 (CH), 127.6 (2CH), 120.6 (CH), 113.2 (CH), 108.1 (CH), 106.2 (C), 67.9 (CH$_2$); HRMS (ESI+) calcd for C$_{18}$H$_{15}$BrN$_3$O$_3$ (M+H)$^+$400.0291, found 400.0295.

6-(Benzyloxy)-5-bromo-N-(4-nitrophenyl)pyridin-3-amine (97)

Compound 97 was prepared according to general procedure D, starting from 3 (200.8 mg, 0.719 mmol) in 3.5 mL of anhydrous 1,4-dioxane. The mixture was heated for 2 h. The crude oil was purified by column chromatography (SiO$_2$, EtOAc/cyclohexane 1:9 to 15/85) to give 97 (217.5 mg, 0.543 mmol, 76%) as an orange solid.

R$_f$=0.17 (cyclohexane/EtOAc 9:1); Mp 153° C.; IR (ATR) 3304, 1599, 1587, 1464, 1445, 1277, 1183, 1105, 1049, 983, 831, 738, 690 cm$^{-1}$; $^1$H NMR (400 MHz, DMSO-d$_6$) δ 9.21 (s, 1H), 8.13 (d, J=2.5, 1H), 8.09 (d, J=9.3, 2H), 8.01 (d, J=2.5, 1H), 7.50-7.46 (m, 2H), 7.43-7.38 (m, 2H), 7.37-7.31 (m, 1H), 6.94 (d, J=9.3, 2H), 5.43 (s, 2H); $^{13}$C NMR (101 MHz, DMSO-d$_6$) δ 155.6 (C), 151.3 (C), 139.6 (CH), 138.2 (C), 136.9 (CH), 136.8 (C), 131.8 (C), 128.4 (2CH), 127.8 (CH), 127.6 (2CH), 126.2 (2CH), 113.0 (2CH), 106.2 (C), 68.1 (CH$_2$); HRMS (ESI+) calcd for C$_{18}$H$_{15}$BrN$_3$O$_3$ (M+H)$^+$400.0291, found 400.0291.

6-(Benzyloxy)-5-bromo-N-(o-tolyl)pyridin-3-amine (98)

Compound 98 was prepared according to general procedure D, starting from 3 (151.1 mg, 0.541 mmol) in 5 mL of anhydrous 1,4-dioxane. The mixture was heated for 2 h 30 min. The crude oil was purified by column chromatography (SiO$_2$, cyclohexane to EtOAc/cyclohexane 5:95) to give 98 (157.1 mg, 0.425 mmol, 79%) as a brown oil.

R$_f$=0.77 (EtOAc/cyclohexane 3:7); IR (ATR) 3398, 1586, 1498, 1464, 1443, 1358, 1291, 1236, 1051, 736, 696 cm$^{-1}$; $^1$H NMR (400 MHz, DMSO-d$_6$) δ 7.84 (d, J=2.5, 1H), 7.62 (d, J=2.5, 1H), 7.47-7.44 (m, 2H), 7.41-7.36 (m, 2H), 7.35 (s, 1H), 7.34-7.29 (m, 1H), 7.17 (d, J=7.4, 1 H), 7.09 (td, J=7.7, 1.5, 1 H), 7.00 (dd, J=8.0, 1.1, 1 H), 6.86 (td, J=7.3, 1.3, 1H), 5.36 (s, 2H), 2.20 (s, 3H); $^{13}$C NMR (101 MHz, DMSO-d$_6$) δ 152.8 (C), 141.6 (C), 137.2 (C), 136.7 (C), 134.6 (CH), 132.2 (CH), 130.9 (CH), 128.4 (2CH), 127.9 (C), 127.7 (CH), 127.5 (2CH), 126.7 (CH), 121.5 (CH), 117.3 (CH), 105.9 (C), 67.7 (CH$_2$), 17.8 (CH$_3$); HRMS (ESI+) calcd for C$_{13}$H$_{18}$BrN$_2$O (M+H)$^+$369.0597, found 369.0607.

N-(6-(Benzyloxy)-5-bromopyridin-3-yl)pyridin-2-amine (99)

Compound 99 was prepared according to general procedure D, starting from 3 (250 mg, 0.896 mmol) in 4.5 mL of anhydrous 1,4-dioxane. The mixture was heated for 5 h 30 min. The crude oil was purified by column chromatography (SiO$_2$, cyclohexane to EtOAc/cyclohexane 2:8) to give 99 (177 mg, 0.497 mmol, 55%) as a red powder.

R$_f$=0.12 (EtOAc:cyclohexane 1:9); Mp>132° C. (decomposition); IR (ATR) 3250-2900, 1600, 1449, 1438, 1354, 1288, 1219, 1048, 992, 764, 736, 695 cm$^{-1}$; $^1$H NMR (400 MHz, DMSO-d$_6$) δ 9.14 (s, 1H), 8.55 (d, J=2.4, 1H), 8.37 (d, J=2.4, 1H), 8.15 (ddd, J=5.0, 1.9, 0.9, 1H), 7.58 (ddd, J=8.4, 7.1, 2.0, 1H), 7.48-7.44 (m, 2H), 7.42-7.36 (m, 2H), 7.34-7.29 (m, 1H), 6.79-6.75 (m, 2H), 5.38 (s, 2H); $^{13}$C NMR (101 MHz, DMSO-d$_6$) δ 155.4 (C), 152.9 (C), 147.2 (CH), 137.5 (CH), 137.2 (C), 134.9 (CH), 133.9 (C), 132.3 (CH), 128.4 (2CH), 127.7 (CH), 127.5 (2CH), 114.7 (CH), 110.7 (CH), 105.1 (C), 67.6 (CH$_2$); HRMS (ESI+) calcd for C$_{17}$H$_{16}$BrN$_3$O (M+H)$^+$356.0393, found 356.0394.

6-(Benzyloxy)-5-bromo-N-(pyridin-3-yl)pyridin-3-amine (100)

Compound 100 was prepared according to general procedure D, starting from 3 (201 mg, 0.720 mmol) in 3.6 mL of anhydrous 1,4-dioxane. The mixture was heated for 2 h 45 min. The crude oil was purified by column chromatography (SiO$_2$, EtOAc/cyclohexane 3:7+0.5% NEt$_3$). To eliminate traces of acetic acid, CH$_2$Cl$_2$ was added to the product and the solution was washed with an aqueous saturated NaHCO$_3$ solution, dried over MgSO$_4$, and filtered. Evaporation gave compound 100 (218.8 mg, 0.614 mmol, 85%) as a red powder.

R$_f$=0.15 (EtOAc/cyclohexane 3:7); Mp 68° C.; IR (ATR) 3239, 1583, 1448, 1356, 1287, 1048, 992, 792, 732, 691 cm$^{-1}$; $^1$H NMR (400 MHz, DMSO-d$_6$) δ 8.31 (s, 1H), 8.25 (d, J=2.8, 1H), 8.02 (dd, J=4.6, 1.4, 1H), 8.01 (d, J=2.5, 1H), 7.84 (d, J=2.5, 1H), 7.48-7.45 (m, 2H), 7.42-7.37 (m, 2H), 7.37-7.30 (m, 2H), 7.21 (dd, J=8.3, 4.6, 1H), 5.38 (s, 2H); $^{13}$C NMR (101 MHz, DMSO-d$_6$) δ 153.9 (C), 140.5 (CH), 140.4 (C), 138.2 (CH), 137.1 (C), 136.0 (CH), 134.3 (C), 133.4 (CH), 128.4 (2CH), 127.7 (CH), 127.5 (2CH), 123.9 (CH), 121.1 (CH), 106.1 (C), 67.8 (CH$_2$); HRMS (ESI+) calcd for C$_{17}$H$_{16}$BrN$_3$O (M+H)$^+$356.0393, found 356.0398.

6-(Benzyloxy)-5-bromo-N-(pyridin-4-yl)pyridin-3-amine (101)

Compound 101 was prepared according to general procedure D, starting from 3 (150.4 mg, 0.539 mmol) in 2.6 mL of anhydrous 1,4-dioxane. The mixture was heated for 2 h 45 min. The crude oil was purified by column chromatography (SiO$_2$, EtOAc/cyclohexane 9:1+0.5% NEt$_3$ to EtOAc+0.5% NEt$_3$). To eliminate traces of acetic acid, CH$_2$Cl$_2$ was added to the product and the solution was washed with an aqueous saturated NaHCO$_3$ solution, dried over MgSO$_4$, and filtered. Evaporation gave compound 101 (138 mg, 0.387 mmol, 72%) as an orange solid.

R$_f$=0.23 (EtOAc+0.5% NEt$_3$); Mp 138° C.; IR (ATR) 3500-3000, 1587, 1470, 1436, 1358, 1056, 992, 811, 729, 693 cm$^{-1}$; $^1$H NMR (400 MHz, DMSO-d$_6$) δ 8.71 (s, 1H), 8.19-8.16 (m, 2H), 8.08 (d, J=2.5, 1H), 7.94 (d, J=2.5, 1H), 7.49-7.45 (m, 2H), 7.43-7.37 (m, 2H), 7.36-7.31 (m, 1H), 6.78-6.75 (m, 2H), 5.41 (s, 2H); $^{13}$C NMR (101 MHz, DMSO-d$_6$) δ 155.1 (C), 150.7 (C), 150.1 (2CH), 138.9 (CH), 136.9 (C), 136.3 (CH), 132.2 (C), 128.4 (2CH), 127.8 (CH), 127.6 (2CH), 108.7 (2CH), 106.1 (C), 68.0 (CH$_2$); HRMS (ESI+) calcd for C$_{17}$H$_{15}$BrN$_3$O (M+H)$^+$356.0393, found 356.0398.

6-(Benzyloxy)-N-(2-fluorophenyl)-5-(1H-indol-4-0) pyridin-3-amine (102)

Compound 102 was prepared according to general procedure A, starting from 86 (191 mg, 0.512 mmol) and the indole-4-boronic acid pinacol ester. The mixture was refluxed for 17 h. The crude oil was purified by column chromatography (SiO$_2$, EtOAc/cyclohexane 5:95 to 1:9) to give 102 (198 mg, 0.484 mmol, 94%) as a beige solid.

R$_f$=0.36 (EtOAc/cyclohexane 2:8); Mp 56° C.; IR (ATR) 3406, 1619, 1507, 1443, 1231, 987, 742, 695 cm$^{-1}$; $^1$H NMR (400 MHz, DMSO-d$_6$) δ 11.19 (s, 1H), 7.99 (d, J=2.8, 1H), 7.89 (d, J=1.4, 1H), 7.54 (d, J=2.8, 1H), 7.42-7.10 (m, 11H), 7.04 (td, J=7.6, 1.4, 1H), 6.83 (dddd, J=8.0, 7.5, 4.8, 1.7, 1H), 6.32 (ddd, J=3.0, 2.0, 0.9, 1H), 5.35 (s, 2H); $^{13}$C NMR (101 MHz, DMSO-d$_6$) δ 155.0 (C), 152.6 (d, J$_{CF}$=241, C), 137.7 (C), 136.0 (C), 135.7 (CH), 133.6 (C), 132.4 (d, J$_{CF}$=11, C), 131.6 (CH), 128.1 (2CH), 127.8 (C), 127.4 (2CH), 127.3 (CH), 126.5 (C), 125.5 (CH), 124.8 (d, J$_{CF}$=3, CH), 123.6 (C), 120.7 (CH), 120.05 (CH), 120.04 (d, J$_{CF}$=7, CH), 116.9 (d, J$_{CF}$=3, CH), 115.7 (d, J$_{CF}$=19, CH), 111.1 (CH), 100.5 (CH), 66.9 (CH$_2$); HRMS (ESI+) calcd for C$_{26}$H$_{21}$FN$_3$O (M+H)$^+$410.1663, found 410.1656.

6-(Benzyloxy)-N-(3-fluorophenyl)-5-(1H-indol-4-0) pyridin-3-amine (103)

Compound 103 was prepared according to general procedure A, starting from 87 (112 mg, 0.300 mmol) and the indole-4-boronic acid pinacol ester. The mixture was refluxed for 16 h. The crude oil was purified by column chromatography (SiO$_2$, cyclohexane to EtOAc/cyclohexane 2:8) to give 103 (122 mg, 0.298 mmol, 99%) as a light green powder.

R$_f$=0.31 (EtOAc/cyclohexane 2:8); Mp 62° C.; IR (ATR) 3391, 1615, 1592, 1443, 1228, 1140, 750 cm$^{-1}$; $^1$H NMR (400 MHz, DMSO-d$_6$) δ 11.20 (5, 1H), 8.30 (5, 1H), 8.05 (d, J=2.7, 1 H), 7.60 (d, J=2.7, 1 H), 7.43-7.11 (m, 10H), 6.77 (dd, J=8.1, 2.1, 1 H), 6.68 (dt, J=11.9, 2.3, 1H), 6.52 (td, J=8.5, 2.5, 1H), 6.32-6.30 (m, 1H), 5.36 (5, 2H); $^{13}$C NMR (101 MHz, DMSO-d$_6$) δ 163.3 (d, J$_{CF}$=241, C), 155.4 (C), 147.1 (d, J$_{CF}$=11, C), 137.6 (C), 136.6 (CH), 136.0 (C), 133.0 (C), 132.5 (CH), 130.9 (d, J$_{CF}$=10, CH), 128.1 (2CH), 127.7 (C), 127.5 (2CH), 127.4 (CH), 126.5 (C), 125.6 (CH), 123.9 (C), 120.7 (CH), 120.1 (CH), 111.2 (CH), 110.6 (d, J$_{CF}$=2, CH), 104.9 (d, J$_{CF}$=21, CH), 101.0 (d, J$_{CF}$=25, CH), 100.5 (CH), 67.0 (CH$_2$); HRMS (ESI+) calcd for C$_{26}$H$_{21}$FN$_3$O (M+H)$^+$410.1663, found 410.1641.

6-(Benzyloxy)-N-(4-fluorophenyl)-5-(1H-indol-4-yl) pyridin-3-amine (104)

Compound 104 was prepared according to general procedure A, starting from 88 (166.2 mg, 0.445 mmol) and the indole-4-boronic acid pinacol ester. The mixture was refluxed for 16 h. The crude oil was purified by column chromatography (SiO$_2$, EtOAc/cyclohexane 1:9 to EtOAc/cyclohexane 2:8) to give 104 (170.2 mg, 0.416 mmol, 93%) as a grey-green solid.

R$_f$=0.21 (EtOAc/cyclohexane 2:8); Mp>82° C. (decomposition); IR (ATR) 3395, 1505, 1213, 751 cm$^{-1}$; $^1$H NMR (400 MHz, DMSO-d$_6$) δ 11.18 (5, 1H), 8.00 (5, 1H), 7.98 (d, J=2.8, 1H), 7.53 (d, J=2.8, 1H), 7.42-7.10 (m, 9H), 7.05 (t, J=8.8, 2H), 7.01 (dd, J=9.2, 4.9, 2H), 6.30 (ddd, J=3.0, 2.0, 0.9, 1H), 5.34 (5, 2H); $^{13}$C NMR (101 MHz, DMSO-d$_6$) δ 156.0 (d, J$_{CF}$=235, C), 154.6 (C), 140.9 (d, J$_{CF}$=2, C), 137.7 (C), 136.0 (C), 134.7 (C), 134.6 (CH), 130.7 (CH), 128.1 (2CH), 127.9 (C), 127.4 (2CH), 127.3 (CH), 126.5 (C), 125.5 (CH), 123.8 (C), 120.7 (CH), 120.0 (CH), 117.1 (d, J$_{CF}$=8, 2CH), 115.8 (d, J$_{CF}$=22, 2CH), 111.1 (CH), 100.6 (CH), 66.9 (CH$_2$); HRMS (ESI+) calcd for C$_{26}$H$_{21}$FN$_3$O (M+H)$^+$410.1663, found 410.1670.

6-(Benzyloxy)-5-(1H-indol-4-yl)-N-(2-methoxyphenyl)pyridin-3-amine (105)

Compound 105 was prepared according to general procedure A, starting from 89 (200 mg, 0.519 mmol) and the indole-4-boronic acid pinacol ester. The mixture was refluxed for h. The crude oil was purified by two column chromatographies (SiO$_2$, EtOAc/cyclohexane 1:9 to 2:8 and SiO$_2$, Et$_2$O/pentane 1:9 to 7:3) to give 105 (175.5 mg, 0.416 mmol, 80%) as a white powder.

R$_f$=0.20 (EtOAc/cyclohexane 2:8); Mp 73° C.; IR (ATR) 3402, 1595, 1507, 1446, 1228, 1114, 1022, 736, 696 cm$^{-1}$; $^1$H NMR (400 MHz, DMSO-d$_6$) δ 11.18 (s, 1H), 8.00 (d, J=2.7, 1H), 7.56 (d, J=2.8, 1H), 7.41-7.21 (m, 8H), 7.15-7.10 (m, 2H), 7.07-7.03 (m, 1H), 6.99-6.95 (m, 1H), 6.83-6.77 (m, 2H), 6.32 (ddd, J=3.0, 2.0, 0.9, 1H), 5.34 (s, 2H), 3.84 (s, 3H); $^{13}$C NMR (101 MHz, DMSO-d$_6$) δ 154.7 (C), 148.6 (C), 137.8 (C), 136.0 (C), 135.8 (CH), 134.3 (C), 133.5 (C), 131.7 (CH), 128.2 (2CH), 128.0 (C), 127.5 (2CH), 127.3 (CH), 126.6 (C), 125.5 (CH), 123.5 (C), 120.8 (CH), 120.7 (CH), 120.1 (CH), 119.8 (CH), 114.3 (CH), 111.3 (CH), 111.0 (CH), 100.7 (CH), 66.9 (CH$_2$), 55.5 (CH$_3$); HRMS (ESI+) calcd for C$_{27}$H$_{24}$N$_3$O$_2$ (M+H)$^+$422.1863, found 422.1865.

6-(Benzyloxy)-5-(1H-indol-4-yl)-N-(3-methoxyphenyl)pyridin-3-amine (106)

Compound 106 was prepared according to general procedure A, starting from 90 (125.4 mg, 0.325 mmol). The mixture was refluxed for 15 h. The crude oil was purified by column chromatography (SiO$_2$, pentane/Et$_2$O 9:1 to 45:55) to give 106 (116 mg, 0.275 mmol, 85%) as a pink powder.

R$_f$=0.14 (EtOAc/cyclohexane 2:8); Mp>53° C. (decomposition); IR (ATR) 3390, 1594, 1494, 1445, 1226, 1154, 750, 692 cm$^{-1}$; $^1$H NMR (400 MHz, DMSO-d$_6$) δ 11.19 (s, 1H), 8.07 (s, 1H), 8.01 (d, J=2.8, 1H), 7.58 (d, J=2.8, 1H), 7.42-7.21 (m, 6H), 7.36 (t, J=2.8, 1H), 7.16-7.11 (m, 2H), 7.09 (t, J=8.1, 1H), 6.56 (dd, J=8.0, 1.9, 1H), 6.51 (t, J=2.2, 1H), 6.35 (dd, J=8.0, 2.3, 1H), 6.32-6.30 (m, 1H), 5.35 (s, 2H), 3.70 (s, 3H); $^{13}$C NMR (101 MHz, DMSO-d$_6$) δ 160.4 (C), 154.9 (C), 145.9 (C), 137.7 (C), 136.0 (C), 135.7 (CH), 133.9 (C), 131.6 (CH), 130.1 (CH), 128.1 (2CH), 127.8 (C), 127.4 (2CH), 127.3 (CH), 126.5 (C), 125.5 (CH), 123.7 (C), 120.7 (CH), 120.0 (CH), 111.1 (CH), 107.6 (CH), 104.5 (CH), 100.8 (CH), 100.5 (CH), 66.9 (CH$_2$), 54.8 (CH$_3$); HRMS (ESI+) calcd for C$_{27}$H$_{24}$N$_3$O$_2$ (M+H)$^+$422.1863, found 422.1862.

6-(Benzyloxy)-5-(1H-indol-4-yl)-N-(4-methoxyphenyl)pyridin-3-amine (107)

Compound 107 was prepared according to general procedure A, starting from 91 (192 mg, 0.498 mmol). The mixture was refluxed for 15 h. The crude oil was purified by column chromatography (SiO$_2$, EtOAc/cyclohexane 9:1 to 15:85) to give 107 (196 mg, 0.465 mmol, 93%) as a grey solid.

R$_f$=0.16 (EtOAc/cyclohexane 2:8); Mp>61° C. (decomposition); IR (ATR) 3391, 1508, 1446, 1224, 1022, 751, 696 cm$^{-1}$; $^1$H NMR (400 MHz, DMSO-d$_6$) δ 11.17 (s, 1H), 7.90

(d, J=2.8, 1H), 7.75 (s, 1H), 7.45 (d, J=2.8, 1H), 7.38 (ddd, J=7.1, 2.0, 0.9, 1H), 7.35 (dd, J=3.1, 2.5, 1H), 7.33-7.20 (m, 5H), 7.15-7.08 (m, 2H), 6.99 (d, J=9.0, 2H), 6.84 (d, J=9.0, 2H), 6.29 (ddd, J=3.0, $J_2$=2.0, 1.0, 1H), 5.32 (s, 2H), 3.68 (s, 3H); $^{13}$C NMR (101 MHz, DMSO-$d_6$) δ 153.8 (C), 153.4 (C), 137.9 (C), 137.2 (C), 136.0 (2C), 132.9 (CH), 129.1 (CH), 128.14 (C), 128.11 (2CH), 127.4 (2CH), 127.3 (CH), 126.5 (C), 125.5 (CH), 123.6 (C), 120.7 (CH), 120.0 (CH), 118.7 (2CH), 114.7 (2CH), 111.0 (CH), 100.6 (CH), 66.8 (CH$_2$), 55.2 (CH$_3$); HRMS (ESI+) calcd for $C_{27}H_{24}N_3O_2$ (M+H)$^+$422.1863, found 422.1867.

Ethyl 2-((6-(benzyloxy)-5-(1H-indol-4-yl)pyridin-3-yl)amino)benzoate (108)

Compound 108 was prepared according to general procedure A, starting from 92 (115 mg, 0.269 mmol) and the indole-4-boronic acid pinacol ester. The mixture was refluxed for 14 h. The crude oil was purified by column chromatography (SiO$_2$, cyclohexane to EtOAc/cyclohexane 12:88) to give 108 (97.6 mg, 0.211 mmol, 78%) as a beige solid.

$R_f$=0.13 (EtOAc/cyclohexane 1:9); Mp 63° C.; IR (ATR) 3411, 3311, 1677, 1582, 1500, 1444, 1227, 1079, 746, 696 cm$^{-1}$; $^1$H NMR (400 MHz, DMSO-$d_6$) δ 11.19 (br s, 1H), 9.23 (s, 1H), 8.15 (d, J=2.7, 1H), 7.90 (dd, J=8.0, 1.6, 1H), 7.70 (d, J=2.7, 1H), 7.43-7.22 (m, 8H), 7.17-7.11 (m, 2H), 7.01 (dd, J=8.6, 0.8, 1H), 6.77 (ddd, J=8.1, 7.1, 1.1, 1H), 6.33 (ddd, J=3.0, 2.0, 0.9, 1H), 5.40 (s, 2H), 4.33 (q, J=7.1, 2H), 1.34 (t, J=7.1, 3H); $^{13}$C NMR (101 MHz, DMSO-$d_6$) δ 167.6 (C=O), 157.0 (C), 148.3 (C), 140.7 (CH), 137.4 (C), 136.04 (CH), 136.02 (C), 134.6 (CH), 131.3 (CH), 131.1 (C), 128.2 (2CH), 127.5 (2CH), 127.4 (C+CH), 126.5 (C), 125.6 (CH), 124.1 (C), 120.7 (CH), 120.1 (CH), 117.1 (CH), 113.3 (CH), 111.5 (C), 111.2 (CH), 100.6 (CH), 67.2 (CH$_2$), 60.5 (CH$_2$), 14.1 (CH$_3$); HRMS (ESI+) calcd for $C_{29}H_{26}N_3O_3$ (M+H)$^+$464.1969, found 464.1970.

Ethyl 3-((6-(benzyloxy)-5-(1H-indol-4-yl)pyridin-3-yl)amino)benzoate (109)

Compound 109 was prepared according to general procedure A, starting from 93 (250 mg, 0.585 mmol) and the indole-4-boronic acid pinacol ester. The mixture was refluxed for 14 h. The crude oil was purified by column chromatography (SiO$_2$, EtOAc/cyclohexane 1:9 to 15:85) to give 109 (212.9 mg, 0.459 mmol, 79%) as a beige solid.

$R_f$=0.16 (EtOAc/cyclohexane 2:8); Mp>186° C. (decomposition); IR (ATR) 3345, 3177, 1697, 1436, 1300, 1223, 746 cm$^{-1}$; $^1$H NMR (400 MHz, DMSO-$d_6$) δ 11.20 (s, 1H), 8.33 (s, 1H), 8.05 (d, J=2.8, 1H), 7.61 (d, J=2.8, 1H), 7.58-7.56 (m, 1H), 7.43-7.19 (m, 10H), 7.16-7.11 (m, 2H), 6.34 (ddd, J=3.0, 2.0, 1.0, 1H), 5.37 (s, 2H), 4.29 (q, J=7.1, 2H), 1.30 (t, J=7.1, 3H); $^{13}$C NMR (101 MHz, DMSO-$d_6$) δ 165.9 (C=O), 155.3 (C), 145.3 (C), 137.6 (C), 136.4 (CH), 136.1 (C), 133.2 (C), 132.3 (CH), 130.9 (C), 129.7 (CH), 128.1 (2CH), 127.7 (C), 127.5 (2CH), 127.4 (CH), 126.5 (C), 125.6 (CH), 123.9 (C), 120.7 (CH), 120.1 (CH), 119.3 (CH), 119.2 (CH), 114.7 (CH), 111.2 (CH), 100.5 (CH), 67.0 (CH$_2$), 60.7 (CH$_2$), 14.2 (CH$_3$); HRMS (ESI+) calcd for $C_{29}H_{26}N_3O_3$ (M+H)$^+$464.1969, found 464.1974.

Ethyl 4-((6-(benzyloxy)-5-(1H-indol-4-yl)pyridin-3-yl)amino)benzoate (110)

Compound 110 was prepared according to general procedure A, starting from 94 (152 mg, 0.356 mmol) and the indole-4-boronic acid pinacol ester. The mixture was refluxed for 15 h. The crude oil was purified by column chromatography (SiO$_2$, EtOAc/cyclohexane 1:9 to 2:8) to give 110 (144.5 mg, 0.312 mmol, 88%) as a light yellow solid.

$R_f$=0.3 (EtOAc/cyclohexane 3:7); Mp>188° C. (decomposition); IR (ATR) 3390, 3314, 1683, 1597, 1456, 1283, 1229, 1174, 1120, 980, 746, 697 cm$^{-1}$; $^1$H NMR (400 MHz, DMSO-$d_6$) δ 11.20 (s, 1H), 8.69 (s, 1H), 8.11 (d, J=2.7, 1H), 7.79 (d, J=8.9, 2H), 7.64 (d, J=2.7, 1H), 7.43-7.22 (m, 6H), 7.38 (t, J=2.8, 1H), 7.17-7.11 (m, 2H), 6.97 (d, J=8.9, 2H), 6.32 (ddd, J=2.9, 1.9, 0.8, 1H), 5.38 (s, 2H), 4.23 (q, J=7.1, 2H), 1.28 (t, J=7.1, 3H); $^{13}$C NMR (101 MHz, DMSO-$d_6$) δ 165.6 (C=O), 156.0 (C), 149.5 (C), 137.7 (CH), 137.5 (C), 136.0 (C), 133.5 (CH), 132.0 (C), 131.2 (2CH), 128.2 (2CH), 127.53 (C), 127.50 (2CH), 127.4 (CH), 126.5 (C), 125.6 (CH), 124.0 (C), 120.7 (CH), 120.1 (CH), 119.0 (C), 113.1 (2CH), 111.2 (CH), 100.5 (CH), 67.1 (CH$_2$), 59.9 (CH$_2$), 14.3 (CH$_3$); HRMS (ESI+) calcd for $C_{29}H_{26}N_3O_3$ (M+H)$^+$464.1969, found 464.1966.

6-(Benzyloxy)-5-(1H-indol-4-yl)-N-(2-nitrophenyl)pyridin-3-amine (111)

Compound 111 was prepared according to general procedure A, starting from 95 (248 mg, 0.620 mmol). The mixture was refluxed for 14 h 20 min. The crude oil was purified by column chromatography (SiO$_2$, EtOAc/cyclohexane 1:9 to 2:8) to give 111 (234 mg, 0.536 mmol, 87%) as an orange solid.

$R_f$=0.24 (cyclohexane/EtOAc 8:2); Mp 87° C.; IR (ATR) 3414, 3347, 3177, 1615, 1571, 1495, 1345, 1260, 1218, 735, 693 cm$^{-1}$, $^1$H NMR (400 MHz, DMSO-$d_6$) δ 11.20 (s, 1H), 9.43 (s, 1H), 8.20 (d, J=2.7, 1H), 8.12 (dd, J=8.6, 1.6, 1H), 7.76 (d, J=2.7, 1H), 7.51 (ddd, J=8.6, 6.7, 1.6, 1H), 7.41 (ddd, J=7.3, 1.7, 1.0, 1H), 7.38-7.23 (m, 6H), 7.19-7.12 (m, 2H), 7.08 (dd, J=8.7, 1.2, 1 H), 6.84 (ddd, J=8.4, 6.9, 1.2, 1H), 6.37 (ddd, J=3.0, 1.9, 0.8, 1H), 5.42 (s, 2H); $^{13}$C NMR (101 MHz, DMSO-$d_6$) δ 157.7 (C), 143.4 (C), 142.3 (CH), 137.6 (CH), 137.3 (C), 136.2 (CH), 136.0 (C), 132.9 (C), 130.0 (C), 128.2 (2CH), 127.53 (2CH), 127.49 (CH), 127.2 (C), 126.5 (C), 126.2 (CH), 125.6 (CH), 124.2 (C), 120.7 (CH), 120.1 (CH), 117.5 (CH), 116.2 (CH), 111.3 (CH), 100.6 (CH), 67.3 (CH$_2$); HRMS (ESI+) calcd for $C_{26}H_{21}N_4O_3$ (M+H)$^+$437.1608, found 437.1617.

6-(Benzyloxy)-5-(1H-indol-4-yl)-N-(3-nitrophenyl)pyridin-3-amine (112)

Compound 112 was prepared according to general procedure A, starting from 96 (170 mg, 0.425 mmol). The mixture was refluxed for 15 h. The crude oil was purified by column chromatography (SiO$_2$, EtOAc/cyclohexane 1:9 to 25:75) to give 112 (180.7 mg, 0.414 mmol, 97%) as an orange solid.

$R_f$=0.35 (cyclohexane/EtOAc 7:3); Mp>189° C. (decomposition); IR (ATR) 3364, 1532, 1341, 983, 747, 735, 689 cm$^{-1}$; $^1$H NMR (400 MHz, DMSO-$d_6$) δ 11.21 (s, 1H), 8.64 (s, 1H), 8.12 (d, J=2.7, 1H), 7.70 (t, J=2.2, 1H), 7.66 (d, J=2.7, 1H), 7.55 (ddd, J=7.9, 2.3, 0.8, 1H), 7.45 (t, J=8.1, 1H), 7.40 (ddd, J=6.7, 2.3, 0.8, 1H), 7.37 (t, J=2.8, 1H), 7.36-7.22 (m, 6H), 7.18-7.11 (m, 2H), 6.36-6.34 (m, 1H), 5.39 (s, 2H); $^{13}$C NMR (101 MHz, DMSO-$d_6$) δ 156.0 (C), 148.8 (C), 146.6 (C), 137.5 (C+CH), 136.1 (C), 133.2 (CH), 132.2 (C), 130.6 (CH), 128.2 (2CH), 127.5 (2CH+C), 127.4 (CH), 126.5 (C), 125.6 (CH), 124.1 (C), 120.7 (CH), 120.4 (CH), 120.1 (CH), 112.6 (CH), 111.2 (CH), 107.5 (CH), 100.5 (CH), 67.1 (CH$_2$); HRMS (ESI+) calcd for C$_{26}$H$_{21}$N$_4$O$_3$ (M+H)$^+$437.1608, found 437.1614.

6-(Benzyloxy)-5-(1H-indol-4-yl)-N-(4-nitrophenyl)pyridin-3-amine (113)

Compound 113 was prepared according to general procedure A, starting from 97 (188.9 mg, 0.472 mmol). The mixture was refluxed for 14 h 30 min. The crude oil was purified by column chromatography (SiO$_2$, EtOAc/cyclohexane 2:8 to 7:3) to give 113 (192.2 mg, 0.440 mmol, 93%) as a brown solid.

R$_f$=0.25 (cyclohexane/EtOAc 7:3); Mp 238° C.; IR (ATR) 3375, 1590, 1498, 1455, 1419, 1296, 1110, 1080, 1007, 837, 750, 735 cm$^{-1}$; $^1$H NMR (400 MHz, DMSO-d$_6$) δ 11.21 (s, 1H), 9.24 (s, 1H), 8.17 (d, J=2.7, 1H), 8.09 (d, J=9.2, 2H), 7.69 (d, J=2.7, 1H), 7.41 (ddd, J=7.0, 2.1, 0.9, 1H), 7.38 (t, J=2.8, 1H), 7.36-7.22 (m, 5H), 7.18-7.12 (m, 2H), 6.99 (d, J=9.3, 2H), 6.34-6.32 (m, 1H), 5.40 (s, 2H); $^{13}$C NMR (101 MHz, DMSO-d$_6$) δ 156.8 (C), 151.8 (C), 139.1 (CH), 137.8 (C), 137.4 (C), 136.0 (C), 134.5 (CH), 130.9 (C), 128.2 (2CH), 127.53 (2CH), 127.47 (CH), 127.3 (C), 126.5 (C), 126.3 (2CH), 125.7 (CH), 124.3 (C), 120.7 (CH), 120.2 (CH), 112.7 (2CH), 111.3 (CH), 100.5 (CH), 67.2 (CH$_2$); HRMS (ESI+) calcd for C$_{26}$H$_{21}$N$_4$O$_3$ (M+H)$^+$437.1608, found 437.1614.

6-(Benzyloxy)-5-(1H-indol-4-yl)-N-(o-tolyl)pyridin-3-amine (114)

Compound 114 was prepared according to general procedure A, starting from 98 (120 mg, 0.325 mmol). The mixture was refluxed for 16 h. The crude oil was purified by column chromatography (SiO$_2$, cyclohexane to EtOAc/cyclohexane 15:85) to give 114 (103 mg, 0.254 mmol, 78%) as a brown solid.

R$_f$=0.45 (EtOAc/cyclohexane 2:8); Mp>58° C. (decomposition); IR (ATR) 3406, 1585, 1498, 1443, 1350, 1229, 746, 695 cm$^{-1}$; $^1$H NMR (400 MHz, DMSO-d$_6$) δ 11.17 (s, 1H), 7.91 (d, J=2.8, 1H), 7.47 (d, J=2.8, 1H), 7.40-7.21 (m, 7H), 7.35 (dd, J=3.1, 2.6, 1H), 7.16-7.10 (m, 3H), 7.09-7.03 (m, 2H), 6.81-6.76 (m, 1H), 6.30 (ddd, J=3.0, 1.9, 0.9, 1H), 5.34 (s, 2H), 2.24 (s, 3H); $^{13}$C NMR (101 MHz, DMSO-d$_6$) δ 154.5 (C), 142.7 (C), 137.8 (C), 136.0 (C), 135.3 (C), 135.2 (CH), 131.2 (CH), 130.8 (CH), 128.1 (2CH), 128.0 (C), 127.4 (2CH), 127.3 (CH), 127.1 (C), 126.6 (CH), 126.5 (C), 125.5 (CH), 123.6 (C), 120.7 (CH), 120.5 (CH), 120.0 (CH), 116.2 (CH), 111.0 (CH), 100.6 (CH), 66.9 (CH$_2$), 18.0 (CH$_3$); HRMS (ESI+) calcd for C$_{27}$H$_{24}$N$_3$O (M+H)$^+$ 406.1914, found 406.1916.

N-(6-(Benzyloxy)-5-(1H-indol-4-yl)pyridin-3-yl)pyridin-2-amine (115)

Compound 115 was prepared according to general procedure A, starting from 99 (139 mg, 0.390 mmol) and the indole-4-boronic acid pinacol ester. The mixture was refluxed for 15 h. The crude oil was purified by column chromatography (SiO$_2$, EtOAc/cyclohexane 1:9 to 3:7). To eliminate traces of acetic acid, CH$_2$Cl$_2$ was added to the product and the solution was washed with an aqueous saturated NaHCO$_3$ solution, dried over MgSO$_4$, and filtered. Evaporation gave compound 115 (135 mg, 0.344 mmol, 88%) as a light green solid.

R$_f$=0.17 (EtOAc/cyclohexane 3:7); Mp 98° C.; IR (ATR) 3396, 1599, 1439, 1423, 1352, 1227, 987, 751, 732, 695 cm$^{-1}$; $^1$H NMR (400 MHz, DMSO-d$_6$) δ 11.18 (s, 1H), 9.03 (s, 1H), 8.45 (d, J=2.7, 1H), 8.21 (d, J=2.7, 1H), 8.08 (ddd, J=5.0, 1.9, 0.8, 1H), 7.55 (ddd, J=8.4, 7.1, 2.0, 1H), 7.43-7.21 (m, 6H), 7.37 (dd, J=3.1, 2.5, 1H), 7.17-7.12 (m, 2H), 6.78 (dt, J=8.4, 0.9, 1H), 6.70 (ddd, J=7.1, 5.0, 1.0, 1H), 6.40 (ddd, J=3.0, 1.9, 0.9, 1H), 5.36 (s, 2H); $^{13}$C NMR (101 MHz, DMSO-d$_6$) δ 155.9 (C), 154.4 (C), 147.2 (CH), 137.9 (C), 137.3 (CH), 136.1 (C), 134.9 (CH), 132.9 (C), 131.3 (CH), 128.13 (C), 128.12 (2CH), 127.4 (2CH), 127.3 (CH), 126.7 (C), 125.5 (CH), 122.8 (C), 120.7 (CH), 120.1 (CH), 114.1 (CH), 111.0 (CH), 110.3 (CH), 100.7 (CH), 66.8 (CH$_2$); HRMS (ESI+) calcd for C$_{25}$H$_{21}$N$_4$O (M+H)$^+$393.1710, found 393.1722.

6-(Benzyloxy)-5-(1H-indol-4-yl)-N-(pyridin-3-yl)pyridin-3-amine (116)

Compound 116 was prepared according to general procedure A, starting from 100 (150 mg, 0.421 mmol) and the indole-4-boronic acid pinacol ester. The mixture was refluxed for 15 h. The crude oil was purified by column chromatography (SiO$_2$, EtOAc/cyclohexane 1:9 to 6:4). To eliminate traces of acetic acid, CH$_2$Cl$_2$ was added to the product and the solution was washed with an aqueous saturated NaHCO$_3$ solution, dried over MgSO$_4$, and filtered. Evaporation gave compound 116 (156 mg, 0.397 mmol, 94%) as a green solid.

R$_f$=0.21 (EtOAc/cyclohexane 6:4); Mp>79° C. (decomposition); IR (ATR) 3374, 1579, 1447, 1423, 1229, 751, 694 cm$^{-1}$; $^1$H NMR (400 MHz, DMSO-d$_6$) δ 11.20 (br s, 1H), 8.29 (d, J=2.7, 1 H), 8.26 (s, 1H), 8.06 (d, J=2.8, 1 H), 7.97 (dd, J=4.6, 1.3, 1 H), 7.68-7.51 (m, 1H), 7.59 (d, J=2.8, 1H), 7.44-7.09 (m, 10H), 6.31 (ddd, J=3.0, 1.9, 0.8, 1H), 5.36 (s, 2H); $^{13}$C NMR (101 MHz, DMSO-d$_6$) δ 155.3 (C), 141.1 (C), 139.9 (CH), 138.0 (CH), 137.6 (C), 136.0 (C), 135.8 (CH), 133.1 (C), 131.7 (CH), 128.1 (2CH), 127.7 (C), 127.5 (2CH), 127.4 (CH), 126.5 (C), 125.6 (CH), 124.0 (C), 123.9 (CH), 120.7 (CH), 120.6 (CH), 120.1 (CH), 111.2 (CH), 100.5 (CH), 67.0 (CH$_2$); HRMS (ESI+) calcd for C$_{25}$H$_{21}$N$_4$O (M+H)$^+$393.1710, found 393.1708.

6-(Benzyloxy)-5-(1H-indol-4-yl)-N-(pyridin-4-yl)pyridin-3-amine (117)

Compound 117 was prepared according to general procedure A, starting from 101 (117 mg, 0.328 mmol) and the indole-4-boronic acid pinacol ester. The mixture was refluxed for 16 h. The crude oil was purified by column chromatography (SiO$_2$, acetone/cyclohexane+0.1% NEt$_3$ 5:5 to 7:3). CH$_2$Cl$_2$ was added to the product and the solution was washed with an aqueous saturated NaHCO$_3$ solution, dried over MgSO$_4$, and filtered. Evaporation gave compound 117 (82.9 mg, 0.211 mmol, 64%) as an orange solid.

R$_f$=0.34 (EtOAc/cyclohexane 7:3+0.1% NEt$_3$); Mp 90° C.; IR (ATR) 3500-3000, 1593, 1512, 1445, 1353, 1214, 995, 816, 752, 733 cm$^{-1}$; $^1$H NMR (400 MHz, DMSO-d$_6$) δ 11.21 (s, 1H), 8.69 (s, 1H), 8.17-8.14 (m, 2H), 8.11 (d, J=2.7, 1H), 7.64 (d, J=2.7, 1H), 7.43-7.22 (m, 6H), 7.37 (dd, J=3.0, 2.6, 1H), 7.17-7.12 (m, 2H), 6.82-6.79 (m, 2H), 6.32 (ddd, J=2.9, 1.9, 0.9, 1H), 5.39 (s, 2H); $^{13}$C NMR (101 MHz, DMSO-d$_6$) δ 156.3 (C), 151.1 (C), 150.1 (2CH), 138.4 (CH), 137.5 (C), 136.0 (C), 134.0 (CH), 131.2 (C), 128.2 (2CH), 127.5 (2CH), 127.46 (C), 127.44 (CH), 126.5 (C), 125.7 (CH), 124.1 (C), 120.7 (CH), 120.1 (CH), 111.3 (CH), 108.5 (2CH), 100.5 (CH), 67.1 (CH$_2$); HRMS (ESI+) calcd for C$_{25}$H$_{21}$N$_4$O (M+H)$^+$393.1710, found 393.1710.

5-((2-Fluorophenyl)amino)-3-(1H-indol-4-yl)pyridin-2(1H)-one (118)

Compound 118 was prepared according to general procedure C, starting from 102 (65.0 mg, 0.159 mmol) and with 3.2 eq. of BBr$_3$. The mixture was stirred for 1 h and was quenched with NEt$_3$ (12 eq.) and MeOH (4 eq.). The crude was purified by column chromatography (SiO$_2$, EtOAc+ 0.5% NEt$_3$) to give 118 (41 mg, 0.128 mmol, 81%) as a beige solid.

R$_f$=0.22 (EtOAc); Mp>141° C. (decomposition); IR (ATR) 3353, 1649, 1609, 1505, 1337, 881, 739 cm$^{-1}$; $^1$H NMR (400 MHz, DMSO-d$_6$) δ 11.61 (br s, 1H), 11.13 (s, 1H), 7.54 (d, J=2.9, 1H), 7.39 (d, J=1.6, 1H), 7.36 (dt, J=8.1, 0.9, 1H), 7.34 (t, J=2.8, 1H), 7.28 (dd, J=7.3, 1.0, 1H), 7.23 (d, J=2.9, 1H), 7.12 (ddd, J=12.2, 8.1, 1.4, 1H), 7.10 (t, J=7.7, 1H), 7.00 (td, J=7.7, 1.4, 1 H), 6.89 (td, J=8.5, 1.6, 1 H), 6.74-6.67 (m, 1H), 6.40-6.38 (m, 1H); $^{13}$C NMR (101 MHz, DMSO-d$_6$) δ 159.7 (C), 151.5 (d, J$_{CF}$=240, C), 138.4 (CH), 136.1 (C), 134.7 (d, J$_{CF}$=11, C), 130.5 (C), 128.3 (C), 127.6 (CH), 126.1 (C), 125.3 (CH), 124.8 (d, J$_{CF}$=3, CH), 121.7 (C), 120.4 (CH), 119.9 (CH), 118.2 (d, J$_{CF}$=7, CH), 115.3 (d, J$_{CF}$=18, CH), 114.6 (d, J$_{CF}$=3, CH), 110.9 (CH), 100.6 (CH); HRMS (ESI+) calcd for C$_{19}$H$_{15}$FN$_3$O (M+H)$^+$ 320.1194, found 320.1195; HPLC purity≥96%, t$_R$=7.93 min, λ=272 nm.

5-((3-Fluorophenyl)amino)-3-(1H-indol-4-yl)pyridin-2(1H)-one (119)

Compound 119 was prepared according to general procedure C, starting from 103 (91.0 mg, 0.222 mmol) and with 3 eq. of BBr$_3$. The mixture was stirred for 3 h and was quenched with NEt$_3$ (10 eq.) and MeOH (6 eq.). The crude was filtered and washed with water, acetone and a mixture of CH$_2$Cl$_2$ and cyclohexane to give 119 (40.8 mg, 0.128 mmol, 57%) as a dark green solid.

R$_f$=0.20 (CH$_2$Cl$_2$/MeOH 95:5); Mp>166° C.; IR (ATR) 3181, 1651, 1602, 1139, 751 cm$^{-1}$; $^1$H NMR (400 MHz, DMSO-d$_6$) δ 11.63 (br s, 1H), 11.14 (s, 1H), 7.78 (s, 1H), 7.50 (d, J=3.0, 1H), 7.36 (d, J=8.3 Hz, 1H), 7.34 (t, J=2.8, 1H), 7.27 (dd, J=7.3, 0.9, 1H), 7.26 (br s, 1H), 7.16 (td, J=8.2, 7.0, 1H), 7.10 (t, J=7.7, 1H), 6.57 (dd, J=8.3, 2.2, 0.8, 1H), 6.48 (dt, J=11.9, 2.3, 1H), 6.47-6.41 (m, 1H), 6.37-6.34 (m, 1H); $^{13}$C NMR (101 MHz, DMSO-d$_6$) δ 163.3 (d, J$_{CF}$=240, C), 159.8 (C), 149.0 (d, J$_{CF}$=11, C), 138.6 (CH), 136.1 (C), 130.78 (C), 130.76 (d, J$_{CF}$=10, CH), 128.2 (C), 128.1 (CH), 126.1 (C), 125.4 (CH), 121.4 (C), 120.5 (CH), 119.9 (CH), 111.0 (CH), 109.6 (CH), 103.8 (d, J$_{CF}$=21, CH), 100.4 (CH), 99.9 (d, J$_{CF}$=25, CH); HRMS (ESI+) calcd for C$_{19}$H$_{15}$FN$_3$O (M+H)$^+$320.1194, found 320.1211; HPLC purity≥95%, t$_R$=7.93 min, λ=288 nm.

5-((4-Fluorophenyl)amino)-3-(1H-indol-4-yl)pyridin-2(1H)-one (120)

To a solution under argon and cooled to −10° C. of 104 (119 mg, 0.291 mmol, 1 eq.) in anhydrous dichloromethane (15 mL) was added dropwise a 1 M BBr$_3$ solution in dichloromethane (4.1 eq.). The mixture was stirred at 0° C. for 15 h in the dark. The reaction mixture was then quenched by addition of NEt$_3$ (12 eq.) and MeOH (9 eq.). After evaporation under reduced pressure, EtOAc was added and the mixture was washed with water and an aqueous saturated NaCl solution. The organic phase was dried over MgSO$_4$, and filtered. After evaporation under reduced pressure, the crude was purified by column chromatography (SiO$_2$, CH$_2$Cl$_2$/MeOH 98:2 to 95:5) to give 120 (64.9 mg, 0.203 mmol, 70%) as a beige solid.

R$_f$=0.28 (CH$_2$Cl$_2$/MeOH 95:5); Mp>146° C. (decomposition); IR (ATR) 3242, 1651, 1599, 1504, 1210, 754 cm$^{-1}$; $^1$H NMR (400 MHz, DMSO-d$_6$) δ 11.54 (br s, 1H), 11.13 (5, 1H), 7.49 (d, J=3.0, 1 H), 7.45 (5, 1H), 7.36 (dt, J=8.0, 0.9, 1H), 7.34 (dd, J=3.2, 2.5 Hz, 1H), 7.26 (dd, J=7.3, 1.0, 1H), 7.18 (br s, 1H), 7.09 (dd, J=8.1, 7.4, 1H), 7.00 (t, J=8.9, 2H), 6.77 (dd, J=9.1, 4.6, 2H), 6.35 (ddd, J=3.1, 2.0, 0.9, 1H); $^{13}$C NMR (101 MHz, DMSO-d$_6$) δ 159.5 (C=O), 155.4 (d, J$_{CF}$=234, C), 143.1 (d, J$_{CF}$=2, C), 138.0 (CH), 136.1 (C), 130.7 (C), 128.3 (C), 126.3 (CH), 126.1 (C), 125.3 (CH), 123.0 (C), 120.4 (CH), 119.9 (CH), 115.7 (d, J$_{CF}$=22, 2CH), 115.2 (d, J$_{CF}$=7.5, 2CH), 110.9 (CH), 100.5 (CH); HRMS (ESI+) calcd for C$_{13}$H$_{15}$FN$_3$O (M+H)$^+$320.1194, found 320.1176; HPLC purity≥98%, t$_R$=7.89 min, λ=276 nm.

3-(1H-Indol-4-yl)-5-((2-methoxyphenyl)amino)pyridin-2(1H)-one (121)

Compound 121 was prepared according to general procedure E, starting from 105 (148 mg, 0.351 mmol) in 3.6 mL of MeOH. The mixture was stirred for 6 h in the dark. The mixture was filtered through a pad of Celite and the solid was washed with EtOAc and MeOH. After evaporation under reduced pressure, the solid was washed with CH$_2$Cl$_2$ to give 121 (97.8 mg, 0.295 mmol, 84%) as a beige solid.

R$_f$=0.51 (CH$_2$Cl$_2$/MeOH 95:5+0.5% NEt$_3$); Mp>240° C. (decomposition); IR (ATR) 3395, 3351, 3314, 1653, 1619, 1595, 1556, 1503, 1454, 1342, 1251, 1116, 1021, 738 cm$^{-1}$; $^1$H NMR (400 MHz, DMSO-d$_6$) δ 11.51 (br s, 1H), 11.13 (s, 1H), 7.53 (d, J=3.0, 1H), 7.35 (dt, J=8.1, 1.0, 1 H), 7.33 (t, J=2.8, 1 H), 7.27 (dd, J=7.4, 1.0, 1 H), 7.20 (br d, J=2.8, 1H), 7.09 (dd, J=8.0, 7.4, 1H), 6.91 (dd, J=8.0, 1.4, 1H), 6.85 (s, 1H), 6.80-6.66 (m, 3H), 6.39-6.37 (m, 1H), 3.82 (s, 3H); $^{13}$C NMR (101 MHz, DMSO-d$_6$) δ 159.7 (C=O), 147.3 (C), 138.8 (CH), 136.1 (C), 136.0 (C), 130.3 (C), 128.4 (C), 127.5 (CH), 126.1 (C), 125.3 (CH), 122.2 (C), 120.8 (CH), 120.4 (CH), 119.9 (CH), 118.0 (CH), 111.9 (CH), 110.83 (CH), 110.82 (CH), 100.6 (CH), 55.4 (CH$_3$); HRMS (ESI+) calcd for C$_{20}$H$_{18}$N$_3$O$_2$ (M+H)$^+$332.1394, found 332.1393; HPLC purity≥97%, t$_R$=8.00 min, λ=276 nm.

3-(1H-Indol-4-yl)-5-((3-methoxyphenyl)amino)pyridin-2(1H)-one (122)

Compound 122 was prepared according to general procedure E, starting from 106 (204.5 mg, 0.485 mmol) in 2 mL of MeOH. The mixture was stirred for 6 h in the dark. The mixture was filtered through a pad of Celite and the solid was washed with EtOAc and MeOH. After evaporation under reduced pressure, the solid was washed with CH$_2$Cl$_2$ to give 122 (129.3 mg, 0.390 mmol, 80%) as a brown solid.

R$_f$=0.45 (CH$_2$Cl$_2$/MeOH 95:5+0.5% NEt$_3$); Mp>141° C. (decomposition); IR (ATR) 3500-3000, 1650, 1591, 1153, 752, 688 cm$^{-1}$; $^1$H NMR (400 MHz, DMSO-d$_6$) δ 11.52 (br s, 1H), 11.14 (s, 1H), 7.52 (s, 1H), 7.51 (d, J=3.0, 1H), 7.36 (dt, J=8.1, 0.9, 1H), 7.34 (t, J=2.8, 1 H), 7.26 (dd, J=7.3, 1.0, 1 H), 7.20 (br d, J=2.6, 1 H), 7.09 (t, J=7.7, 1 H), 7.05 (t, J=8.1, 1H), 6.37-6.33 (m, 2H), 6.30 (t, J=2.2, 1H), 6.27 (ddd, J=8.1, J$_2$=2.5, 0.8, 1H), 3.68 (s, 3H); $^{13}$C NMR (101 MHz, DMSO-d$_6$) δ 160.4 (C=O), 159.6 (C), 148.0 (C), 138.5 (CH), 136.1 (C), 130.5 (C), 130.0 (CH), 128.3 (C), 127.0 (CH), 126.1 (C), 125.3 (CH), 122.3 (C), 120.5 (CH), 119.9 (CH), 110.9 (CH), 106.6 (CH), 103.4 (CH), 100.5 (CH), 99.7 (CH), 54.8 (CH$_3$); HRMS (ESI+) calcd for $C_{20}H_{18}N_3O_2$ (M+H)+332.1394, found 332.1392; HPLC purity≥97%, $t_R$=7.81 min, λ=278 nm.

3-(1H-Indol-4-yl)-5-((4-methoxyphenyl)amino)pyridin-2(1H)-one (123)

Compound 123 was prepared according to general procedure E, starting from 107 (100.6 mg, 0.239 mmol) in 1 mL of MeOH. The mixture was stirred for 6 h in the dark. The mixture was filtered through a pad of Celite and the solid was washed with EtOAc and MeOH. After evaporation under reduced pressure, compound 123 (78.4 mg, 0.237 mmol, 99%) was obtained as a red solid.

$R_f$=0.39 ($CH_2Cl_2$/MeOH 95:5+0.5% $NEt_3$); Mp>132° C. (decomposition); IR (ATR) 3500-3000, 1651, 1605, 1506, 1233, 1036, 820, 756 cm$^{-1}$; $^1$H NMR (400 MHz, DMSO-$d_6$) δ 11.44 (br s, 1H), 11.13 (s, 1H), 7.49 (d, J=3.0, 1H), 7.37-7.33 (m, 2H), 7.25 (d, J=7.3, 1H), 7.19 (s, 1H), 7.09 (br s, 1H), 7.09 (t, J=7.7, 1 H), 6.83-6.76 (m, 4H), 6.36-6.34 (m, 1H), 3.66 (s, 3H); $^{13}$C NMR (101 MHz, DMSO-$d_6$) δ 159.3 (C=O), 152.5 (C), 139.7 (C), 137.2 (CH), 136.1 (C), 130.5 (C), 128.5 (C), 126.1 (C), 125.3 (CH), 124.6 (C), 124.0 (CH), 120.4 (CH), 119.9 (CH), 116.5 (2CH), 114.7 (2CH), 110.8 (CH), 100.6 (CH), 55.3 ($CH_3$); HRMS (ESI+) calcd for $C_{20}H_{18}N_3O_2$ (M+H)+332.1394, found 332.1398; HPLC purity≥96%, $t_R$=7.71 min, λ=280 nm.

Ethyl 2-((5-(1H-indol-4-yl)-6-oxo-1,6-dihydropyridin-3-yl)amino)benzoate (124)

Compound 124 was prepared according to general procedure E, starting from 108 (104.6 mg, 0.226 mmol) in 2 mL of MeOH. The mixture was stirred for 6 h in the dark. The mixture was filtered through a pad of Celite and the solid was washed with EtOAc and MeOH. After evaporation under reduced pressure, compound 124 (84 mg, 0.225 mmol, quant.) was obtained as an orange solid.

$R_f$=0.35 ($CH_2Cl_2$/MeOH 98:2+0.5% $NEt_3$); Mp>263° C. (decomposition); IR (ATR) 3285, 1680, 1654, 1627, 1452, 1238, 750 cm$^{-1}$; $^1$H NMR (400 MHz, DMSO-$d_6$) δ 11.79 (br s, 1H), 11.13 (s, 1H), 8.88 (s, 1H), 7.87 (dd, J=8.1, 1.7, 1H), 7.51 (d, J=3.0, 1H), 7.43-7.37 (m, 2H), 7.36 (dt, J=8.1, 0.9, 1H), 7.33 (t, J=2.8, 1H), 7.26 (dd, J=7.4, 0.9, 1H), 7.09 (t, J=7.7, 1H), 6.82 (dd, J=8.6, 0.9, 1 H), 6.72 (ddd, J=8.2, 7.2, 1.2, 1 H), 6.38-6.35 (m, 1H), 4.31 (q, J=7.1, 2H), 1.33 (t, J=7.1, 3H); $^{13}$C NMR (101 MHz, DMSO-$d_6$) δ 167.5 (C=O), 160.3 (C=O), 149.8 (C), 140.0 (CH), 136.1 (C), 134.6 (CH), 131.5 (CH), 131.2 (CH), 130.9 (C), 128.2 (C), 126.1 (C), 125.3 (CH), 120.4 (CH), 119.9 (CH), 119.3 (C), 116.4 (CH), 113.2 (CH), 110.9 (CH), 110.7 (C), 100.5 (CH), 60.4 ($CH_2$), 14.2 ($CH_3$); HRMS (ESI+) calcd for $C_{22}H_{20}N_3O_3$ (M+H)+374.1499, found 374.1490; HPLC purity≥96%, $t_R$=8.65 min, λ=270 nm.

Ethyl 3-((5-(1H-indol-4-yl)-6-oxo-1,6-dihydropyridin-3-yl)amino)benzoate (125)

Compound 125 was prepared according to general procedure E, starting from 109 (169.3 mg, 0.365 mmol) in 4 mL of MeOH. The mixture was stirred for 20 h in the dark. The mixture was filtered through a pad of Celite and the solid was washed with EtOAc and MeOH. The obtained crude was purified by column chromatography ($NEt_3$-treated $SiO_2$, $CH_2Cl_2$/MeOH 95:5) to give 125 containing $NEt_3$ salts. The product was washed with $CH_2Cl_2$ to give 125 (72.1 mg, 0.193 mmol, 53%) as a beige solid.

$R_f$=0.35 ($CH_2Cl_2$/MeOH 95:5+0.5% $NEt_3$); Mp>244° C. (decomposition); IR (ATR) 3365, 3207, 1691, 1660, 1601, 1539, 1465, 1285, 846, 746 cm$^{-1}$; $^1$H NMR (400 MHz, DMSO-$d_6$) δ 11.61 (s, 1H), 11.15 (s, 1H), 7.82 (s, 1H), 7.50 (d, J=2.9, 1H), 7.38-7.25 (m, 7H), 7.10 (t, J=7.7, 1H), 7.02 (dt, J=6.6, 2.5, 1H), 6.39 (ddd, J=3.0, 2.0, 1.0, 1H), 4.28 (q, J=7.1, 2H), 1.29 (t, J=7.1, 3H); $^{13}$C NMR (101 MHz, DMSO-$d_6$) δ 166.0 (C=O), 159.8 (C=O), 147.2 (C), 138.5 (CH), 136.1 (C), 130.83 (C), 130.76 (C), 129.6 (CH), 128.2 (C), 127.8 (CH), 126.1 (C), 125.4 (CH), 121.6 (C), 120.4 (CH), 119.9 (CH), 118.4 (CH), 118.2 (CH), 113.5 (CH), 111.0 (CH), 100.4 (CH), 60.6 ($CH_2$), 14.2 ($CH_3$); HRMS (ESI+) calcd for $C_{22}H_{20}N_3O_3$ (M+H)+374.1499, found 374.1499; HPLC purity≥96%, $t_R$=8.03 min, λ=278 nm.

Ethyl 4-((5-(1H-indol-4-yl)-6-oxo-1,6-dihydropyridin-3-yl)amino)benzoate (126)

Compound 126 was prepared according to general procedure E, starting from 110 (145.4 mg, 0.314 mmol) in 3 mL of MeOH. The mixture was stirred for 6 h 30 min in the dark. The mixture was filtered through a pad of Celite and the solid was washed with EtOAc and MeOH. The filtrate was evaporated under reduced pressure to give 126 (116.6 mg, 0.312 mmol, quant.) as a yellow-brown solid.

$R_f$=0.30 ($CH_2Cl_2$/MeOH 95:5+0.5% $NEt_3$); Mp>255° C. (decomposition); IR (ATR) 3500-3200, 3280, 1687, 1656, 1595, 1454, 1257, 1168, 1098, 756 cm$^{-1}$; $^1$H NMR (400 MHz, DMSO-$d_6$) δ 11.55 (br s, 1H), 11.14 (s, 1H), 8.21 (s, 1H), 7.76 (d, J=8.8, 2H), 7.50 (d, J=2.9, 1 H), 7.37-7.33 (m, 2H), 7.33 (br s, 1H), 7.28 (dd, J=7.3, 0.9, 1 H), 7.09 (t, J=7.7, 1H), 6.78 (d, J=8.9, 2H), 6.37-6.35 (m, 1H), 4.22 (q, J=7.1, 2H), 1.27 (t, J=7.1, 3H); $^{13}$C NMR (101 MHz, DMSO-$d_6$) δ 165.7 (C=O), 160.2 (C=O), 151.3 (C), 138.5 (CH), 136.1 (C), 131.2 (2CH), 130.6 (C), 129.4 (CH), 128.3 (C), 126.1 (C), 125.4 (CH), 120.44 (CH), 120.36 (C), 119.9 (CH), 118.1 (C), 112.3 (2CH), 110.9 (CH), 100.5 (CH), 59.8 ($CH_2$), 14.3 ($CH_3$); HRMS (ESI+) calcd for $C_{22}H_{20}N_3O_3$ (M+H)+374.1499, found 374.1486; HPLC purity≥98%, $t_R$=7.95 min, λ=310 nm.

3-(1H-Indol-4-yl)-5-((2-nitrophenyl)amino)pyridin-2(1H)-one (127)

To a solution under argon and cooled to −10° C. of 111 (119 mg, 0.273 mmol) in anhydrous dichloromethane (14 mL) was added dropwise a 1 M $BBr_3$ solution in dichloromethane (3.7 eq.). The mixture was stirred at 0° C. for 3 h 15 min in the dark. The reaction mixture was then quenched by addition of $NEt_3$ (13 eq.) and MeOH (5 eq.). After evaporation under reduced pressure, EtOAc was added and the mixture was washed with water and an aqueous saturated NaCl solution. The organic phase was dried over $MgSO_4$, and filtered. After evaporation under reduced pressure, the crude was purified by column chromatography ($NEt_3$-treated $SiO_2$, $CH_2Cl_2$/MeOH 98:2 to 95:5). To eliminate traces of $NEt_3$ salts, the product was washed with $CH_2Cl_2$ to give 127 (31 mg, 0.090 mmol, 33%) as an orange solid.

$R_f$=0.33 ($CH_2Cl_2$/MeOH 95:5+0.5% $NEt_3$); Mp>268° C. (decomposition); IR (ATR) 3350, 3232, 1653, 1606, 1498, 1470, 1257, 744, 726, 696 cm$^{-1}$; $^1$H NMR (400 MHz, DMSO-$d_6$) δ 11.87 (s, 1H), 11.13 (s, 1H), 9.18 (s, 1H), 8.10 (dd, J=8.5, 1.6, 1H), 7.55 (d, J=2.9, 1 H), 7.53 (ddd, J=8.5, 7.0, 1.5, 1 H), 7.48 (br s, 1H), 7.36 (dt, J=8.1, 0.9, 1 H), 7.33 (dd, J=3.1, 2.5, 1H), 7.28 (dd, J=7.4, 0.9, 1H), 7.10 (t, J=7.8, 1H), 7.01 (dd, J=8.7, 1.2, 1 H), 6.81 (ddd, J=8.4, 6.9, 1.2, 1

H), 6.42-6.40 (m, 1H); $^{13}$C NMR (101 MHz, DMSO-d$_6$) δ 160.3 (C=O), 144.5 (C), 140.1 (CH), 136.3 (CH), 136.1 (C), 132.4 (C), 132.3 (CH), 131.0 (C), 128.0 (C), 126.2 (CH+C), 125.4 (CH), 120.4 (CH), 119.9 (CH), 118.4 (C), 117.0 (CH), 116.2 (CH), 111.0 (CH), 100.7 (CH); HRMS (ESI+) calcd for C$_{19}$H$_{16}$N$_4$O$_3$ (M+H)$^+$347.1139, found 347.1150; HPLC purity≥96%, t$_R$=8.11 min, λ=276 nm.

3-(1H-Indol-4-yl)-5-((3-nitrophenyl)amino)pyridin-2 (1H)-one (128)

To a solution under argon and cooled to −10° C. of 112 (90 mg, 0.206 mmol) in anhydrous dichloromethane (11 mL) was added dropwise a 1 M BBr$_3$ solution in dichloromethane (4 eq.). The mixture was stirred at 0° C. for 5 h in the dark. The reaction mixture was then quenched by addition of NEt$_3$ (17 eq.) and MeOH (6 eq.). After evaporation under reduced pressure, EtOAc was added and the mixture was washed with water and an aqueous saturated NaCl solution. The organic phase was dried over MgSO$_4$, and filtered. After evaporation under reduced pressure, the crude was purified by column chromatography (NEt$_3$-treated SiO$_2$, 98:2 CH$_2$Cl$_2$/MeOH to 9:1 CH$_2$Cl$_2$/MeOH) to give 128 (65.1 mg, 0.188 mmol, 91%) as an orange brown solid.

R$_f$=0.25 (CH$_2$Cl$_2$/MeOH 95:5+0.5% NEt$_3$); Mp>295° C. (decomposition); IR (ATR) 3396, 3283, 1604, 1655, 1604, 1509, 1455, 1337, 761, 724 cm$^{-1}$; $^1$H NMR (400 MHz, DMSO-d$_6$) δ 11.74 (br s, 1H), 11.15 (s, 1H), 8.15 (s, 1H), 7.53 (d, J=3.0, 1H), 7.51-7.47 (m, 2H), 7.42 (t, J=8.1, 1 H), 7.37 (d, J=8.0, 1 H), 7.37-7.32 (br s, 1H), 7.33 (t, J=2.7, 1H), 7.27 (d, J=7.1, 1H), 7.18-7.14 (m, 1H), 7.10 (t, J=7.7, 1H), 6.38-6.36 (m, 1H); $^{13}$C NMR (101 MHz, DMSO-d$_6$) δ 159.9 (C=O), 148.9 (C), 148.4 (C), 138.6 (CH), 136.1 (C), 131.1 (C), 130.5 (CH), 129.1 (CH), 128.1 (C), 126.1 (C), 125.4 (CH), 120.5 (C), 120.4 (CH), 120.0 (CH), 119.7 (CH), 111.8 (CH), 111.0 (CH), 106.6 (CH), 100.4 (CH); HRMS (ESI+) calcd for C$_{19}$H$_{16}$N$_4$O$_3$ (M+H)$^+$347.1139, found 347.1140; HPLC purity≥95%, t$_R$=7.92 min, λ=260 nm.

3-(1H-Indol-4-yl)-5-((4-nitrophenyl)amino)pyridin-2 (1H)-one (129)

To a solution under argon and cooled to −10° C. of 113 (125 mg, 0.286 mmol) in anhydrous dichloromethane (15 mL) was added dropwise a 1 M BBr$_3$ solution in dichloromethane (4 eq.). The mixture was stirred in the dark at 0° C. for 5 h, then 2 h 30 min at 10° C. The reaction mixture was then quenched by addition of NEt$_3$ (12 eq.) and MeOH (5 eq.). After evaporation under reduced pressure, EtOAc was added and the mixture was washed with water and an aqueous saturated NaCl solution. The organic phase was dried over MgSO$_4$, and filtered. After evaporation under reduced pressure, the crude was purified by column chromatography (NEt$_3$-treated SiO$_2$, CH$_2$Cl$_2$/MeOH 98:2 to 92:8) to give 129 (30.3 mg, 0.087 mmol, 31%) as a red brown solid.

R$_f$=0.22 (CH$_2$Cl$_2$/MeOH 95:5+0.5% NEt$_3$); Mp>295° C. (decomposition); IR (ATR) 3362, 3280, 1655, 1633, 1588, 1467, 1299, 1111, 747 cm$^{-1}$, $^1$H NMR (400 MHz, DMSO-d$_6$) δ 11.82 (s, 1H), 11.15 (s, 1H), 8.82 (s, 1H), 8.07 (d, J=9.3, 2H), 7.53 (d, J=2.9, 1H), 7.41 (br s, 1H), 7.37 (dt, J=8.1, 0.9, 1H), 7.35 (t, J=2.8, 1H), 7.27 (d, J=7.2, 1H), 7.10 (t, J=7.7, 1H), 6.82 (d, J=9.3, 2H), 6.38-6.36 (m, 1H); $^{13}$C NMR (101 MHz, DMSO-d$_6$) δ 160.0 (C=O), 153.2 (C), 138.5 (CH), 137.3 (C), 136.1 (C), 131.1 (C), 130.0 (CH), 128.0 (C), 126.3 (2CH), 126.1 (C), 125.4 (CH), 120.4 (CH), 119.9 (CH), 119.3 (C), 112.2 (2CH), 111.1 (CH), 100.5 (CH); HRMS (ESI+) calcd for C$_{19}$H$_{16}$N$_4$O$_3$ (M+H)$^+$ 347.1139, found 347.1140; HPLC purity≥97%, t$_R$=7.80 min, λ=378 nm.

3-(1H-Indol-4-yl)-5-(o-tolylamino)pyridin-2(1H)-one (130)

Compound 130 was prepared according to general procedure E, starting from 114 (69.4 mg, 0.171 mmol). The mixture was stirred for 6 h at room temperature in the dark. The crude was purified by column chromatography (NEt$_3$-treated SiO$_2$, CH$_2$Cl$_2$/MeOH 95:5) to give 130 containing NEt$_3$ salts. CH$_2$Cl$_2$ was added and the solution was washed with a saturated NaHCO$_3$ solution and water. The organic phase was dried over MgSO$_4$ and filtered. After evaporation under reduced pressure, product 130 (41.8 mg, 0.133 mmol, 77%) was obtained as a red powder.

R$_f$=0.18 (CH$_2$Cl$_2$/MeOH 95:5+0.5% NEt$_3$); Mp>199° C.; IR (ATR) 3500-3000, 1650, 1599, 1557, 1498, 1113, 747, 614 cm$^{-1}$; $^1$H NMR (400 MHz, DMSO-d$_6$) δ 11.53 (br s, 1H), 11.13 (s, 1H), 7.51 (d, J=3.0, 1H), 7.35 (dt, J=8.1, 1.0, 1H), 7.33 (t, J=2.8, 1H), 7.27 (dd, J=7.3, 0.9, 1H), 7.13 (br s, 1H), 7.09 (t, J=7.7, 1H), 7.07 (d, J=7.3, 1H), 7.02 (t, J=7.7, 1H), 6.75 (s, 1H), 6.72 (d, J=8.2, 1H), 6.67 (td, J=7.2, 1.1, 1H), 6.36 (ddd, J=3.1, 2.0, 0.9, 1H), 2.20 (s, 3H); $^{13}$C NMR (101 MHz, DMSO-d$_6$) δ 159.6 (C=O), 144.8 (C), 138.7 (CH), 136.1 (C), 130.5 (CH), 130.4 (C), 128.3 (C), 126.9 (CH), 126.6 (CH), 126.1 (C), 125.3 (CH), 124.3 (C), 123.1 (C), 120.4 (CH), 119.9 (CH), 118.5 (CH), 113.1 (CH), 110.8 (CH), 100.5 (CH), 17.8 (CH$_3$); HRMS (ESI+) calcd for C$_{20}$H$_{18}$N$_3$O (M+H)$^+$316.1444, found 316.1449; HPLC purity≥96%, t$_R$=8.09 min, λ=278 nm.

3-(1H-Indol-4-yl)-5-(pyridin-2-ylamino)pyridin-2 (1H)-one (131)

Compound 131 was prepared according to general procedure C, starting from 115 (102.6 mg, 0.261 mmol) and with 4 eq. of BBr$_3$. The mixture was stirred for 4 h 40 min and was quenched with NEt$_3$ (14 eq.) and MeOH (9 eq.). The crude was purified by column chromatography (SiO$_2$, acetone/cylohexane 5:5+0.5% NEt$_3$ to 6:4+0.5% NEt$_3$) to give 131 (48.5 mg, 0.160 mmol, 61%) as a light orange solid.

R$_f$=0.38 (acetone/cyclohexane 7:3); Mp>171° C. (decomposition); IR (ATR) 3500-3000, 1652, 1596, 1338, 754 cm$^{-1}$; $^1$H NMR (400 MHz, DMSO-d$_6$) δ 11.44 (br s, 1H), 11.13 (s, 1H), 8.67 (s, 1H), 8.10 (dd, J=5.0, 1.5, 1H), 7.97 (d, J=2.8, 1H), 7.78 (d, J=2.8, 1H), 7.51 (ddd, J=8.7, 7.1, 2.0, 1H), 7.38-7.35 (m, 2H), 7.31 (dd, J=7.4, 0.9, 1H), 7.10 (t, J=7.7, 1H), 6.71-6.68 (m, 1H), 6.67 (ddd, J=7.1, 5.1, 0.9, 1H), 6.51-6.49 (m, 1H); $^{13}$C NMR (101 MHz, DMSO-d$_6$) δ 159.1 (C=O), 158.5 (CH), 156.3 (C), 147.2 (CH), 137.1 (CH), 136.1 (C), 136.0 (CH), 129.8 (C), 128.5 (C), 126.2 (C), 125.2 (CH), 122.1 (C), 120.4 (CH), 120.0 (CH), 113.5 (CH), 110.8 (CH), 110.0 (CH), 100.8 (CH); HRMS (ESI+) calcd for C$_{18}$H$_{16}$N$_4$O (M+H)$^+$303.1240, found 303.1247; HPLC purity≥98%, t$_R$=5.82 min, λ=320 nm.

3-(1H-Indol-4-yl)-5-(pyridin-3-ylamino)pyridin-2 (1H)-one (132)

Compound 132 was prepared according to general procedure E, starting from 116 (114.6 mg, 0.292 mmol) and with 0.14 eq. of Pd(OH)$_2$/C. The mixture was stirred under H$_2$ for 3 days in the dark. The crude was purified by column chromatography (SiO$_2$, CH$_2$Cl$_2$/MeOH 95:5 to 9:1) to give 132 (42 mg, 0.139 mmol, 48%) as a light orange solid.

R$_f$=0.35 (CH$_2$Cl$_2$/MeOH 9:1+0.5% NEt$_3$); Mp>179° C. (decomposition); IR (ATR) 3500-3000, 1651, 1579, 1336, 752, 706 cm$^{-1}$; $^1$H NMR (400 MHz, DMSO-d$_6$) δ 11.61 (s, 1H), 11.14 (s, 1H), 8.13 (dd, J=2.6, 0.8, 1H), 7.90 (dd, J=4.4, 1.6, 1H), 7.73 (s, 1H), 7.51 (d, J=3.0, 1 H), 7.36 (dt, J=8.0, 1.0, 1 H), 7.34 (t, J=2.8, 1 H), 7.28 (br s, 1H), 7.26 (dd, J=7.4, 1.0, 1H), 7.18-7.09 (m, 2H), 7.10 (t, J=7.8, 1H), 6.37-6.35 (m, 1H); $^{13}$C NMR (101 MHz, DMSO-d$_6$) δ 159.7 (C=O), 143.0 (C), 138.9 (CH), 138.1 (CH), 136.7 (CH), 136.1 (C), 130.9 (C), 128.2 (C), 127.6 (C), 126.1 (C), 125.4 (CH), 123.9 (CH), 121.4 (C), 120.5 (CH), 119.9 (CH), 119.4 (CH), 111.0 (CH), 100.5 (CH); HRMS (ESI+) calcd for C$_{18}$H$_{16}$N$_4$O (M+H)$^+$303.1240, found 303.1246; HPLC purity≥96%, t$_R$=5.71 min, λ=268 nm.

3-(1H-Indol-4-yl)-5-(pyridin-4-ylamino)pyridin-2 (1H)-one (133)

Compound 133 was prepared by a catalytic hydrogenation performed in an H-cube reactor (H-cube Mini—Thales Nano). A solution of 117 (61 mg, 0.155 mmol) in MeOH (6 mL) was engaged in reaction (Pd(OH)$_2$/C cartridge, room temperature, 1 mL/min, 3 cycles). The crude was purified by column chromatography (NEt$_3$-treated SiO$_2$, CH$_2$Cl$_2$/MeOH 95:5 to 8:2) to give 133 (29 mg, 0.096 mmol, 62%) as a light brown solid.

R$_f$=0.03 (CH$_2$Cl$_2$/MeOH 95:5); Mp>200° C. (decomposition); IR (ATR) 3400-2900, 1655, 1587, 1357, 1332, 1215, 1027, 1000, 808, 755, 638 cm$^{-1}$; $^1$H NMR (400 MHz, DMSO-d$_6$) δ 11.71 (br s, 1H), 11.15 (s, 1H), 8.22 (s, 1H), 8.13-8.10 (m, 2H), 7.50 (d, J=3.0, 1H), 7.37 (dt, J=8.0, 1.0, 1H), 7.35 (t, J=2.7, 1H), 7.33 (br s, 1H), 7.27 (dd, J=7.4, 1.0, 1H), 7.10 (t, J=7.7, 1H), 6.65-6.63 (m, 2H), 6.36 (ddd, J=3.0, 2.0, 0.8, 1H); $^{13}$C NMR (101 MHz, DMSO-d$_6$) δ 159.9 (C=O), 152.6 (C), 149.8 (2CH), 138.6 (CH), 136.1 (C), 130.9 (C), 129.4 (CH), 128.1 (C), 126.1 (C), 125.4 (CH), 120.5 (CH), 119.9 (CH), 119.5 (C), 111.0 (CH), 108.1 (2CH), 100.5 (CH); HRMS (ESI+) calcd for C$_{18}$H$_{15}$N$_4$O (M+H)$^+$303.1240, found 303.1236; HPLC purity≥95%, t$_R$=5.66 min, λ=270 nm.

5-((3-hydroxyphenyl)amino)-3-(1H-indol-4-yl)pyridin-2(1H)-one (134)

To a solution under argon and cooled to −10° C. of 106 (103 mg, 0.244 mmol) in anhydrous dichloromethane (13 mL) was added dropwise a 1 M BBr$_3$ solution in dichloromethane (4.1 eq.). The mixture was stirred at 0° C. for 15 h in the dark. The reaction mixture was then quenched by addition of NEt$_3$ (13 eq.) and MeOH (10 eq.). After evaporation under reduced pressure, EtOAc was added and the mixture was washed with water and an aqueous saturated NaCl solution. The organic phase was dried over MgSO$_4$, and filtered. After evaporation under reduced pressure, the crude was purified by two column chromatographies (SiO$_2$, EtOAc/MeOH 98:2 to 97:3 and SiO$_2$, CH$_2$Cl$_2$/MeOH 99:1 to 92:8) to give 134 (40 mg, 0.126 mmol, 52%) as a beige solid.

R$_f$=0.12 (CH$_2$Cl$_2$/MeOH 95:5); Mp>248° C. (decomposition); IR (ATR) 3500-3000, 1647, 1595, 1155, 751, 738, 684 cm$^{-1}$; $^1$H NMR (400 MHz, DMSO-d$_6$) δ 11.51 (s, 1H), 11.13 (s, 1H), 9.09 (s, 1H), 7.52 (d, J=2.9, 1 H), 7.39 (s, 1H), 7.36 (dt, J=8.2, 0.9, 1 H), 7.34 (t, J=2.9, 1 H), 7.27 (dd, J=7.3, 0.9, 1H), 7.17 (d, J=3.0, 1H), 7.10 (t, J=7.7, 1H), 6.92 (t, J=8.3, 1H), 6.38-6.36 (m, 1H), 6.23-6.20 (m, 2H), 6.11-6.08 (m, 1H); $^{13}$C NMR (101 MHz, DMSO-d$_6$) δ 159.6 (C=O), 158.3 (C), 147.9 (C), 138.6 (CH), 136.1 (C), 130.5 (C), 129.9 (CH), 128.3 (C), 126.7 (C), 126.1 (C), 125.3 (CH), 122.6 (C), 120.4 (CH), 119.9 (CH), 110.9 (CH), 105.33 (CH), 105.27 (CH), 100.7 (CH), 100.6 (CH); HRMS (ESI+) calcd for C$_{19}$H$_{16}$N$_3$O$_2$ (M+H)$^+$318.1237, found 318.1233; HPLC purity≥99%, t$_R$=7.06 min, λ=280 nm.

5-((2-Aminophenyl)amino)-3-(1H-indol-4-yl)pyridin-2(1H)-one (135)

Compound 135 was prepared according to general procedure E, starting from 111 (50.4 mg, 0.115 mmol) and with 0.8 eq. of Pd(OH)$_2$/C. The mixture was stirred under H$_2$ for 4 h 30 min in the dark. The crude was purified by column chromatography (SiO$_2$, CH$_2$Cl$_2$/MeOH 95:5) to give 135 (22.1 mg, 0.070 mmol, 60%) as a brown solid.

R$_f$=0.20 (CH$_2$Cl$_2$/MeOH 95:5+0.5% NEt$_3$); Mp>208° C. (decomposition); IR (ATR) 3500-3000, 1649, 1597, 1556, 1500, 1452, 747 cm$^{-1}$; $^1$H NMR (400 MHz, DMSO-d$_6$) δ 11.34 (s, 1H), 11.11 (s, 1H), 7.45 (d, J=2.7, 1 H), 7.36-7.31 (m, 2H), 7.26 (d, J=7.0, 1H), 7.08 (t, J=7.7, 1H), 6.83 (br s, 1H), 6.76 (d, J=7.7, 1 H), 6.72-6.65 (m, 2H), 6.54 (s, 1H), 6.53-6.48 (m, 1H), 6.40-6.37 (m, 1H), 4.73 (s, 2H); $^{13}$C NMR (101 MHz, DMSO-d$_6$) δ 159.0 (C=O), 139.7 (C), 136.2 (CH), 136.1 (C), 130.9 (C), 130.0 (C), 128.6 (C), 126.2 (C), 125.5 (C), 125.2 (CH), 121.9 (C), 121.8 (CH), 120.4 (CH), 119.9 (CH), 118.3 (CH), 116.8 (CH), 115.0 (CH), 110.7 (CH), 100.6 (CH); HRMS (ESI+) calcd for C$_{19}$H$_{17}$N$_4$O (M+H)$^+$317.1397, found 317.1394.

4-(2-(Benzyloxy)-5-nitropyridin-3-yl)-1H-indole (136)

Compound 136 was prepared according to general procedure A, starting from 2 (1 g, 3.24 mmol). The mixture was refluxed for 14 h 30 min. The crude oil was purified by three column chromatographies (SiO$_2$, EtOAc/cyclohexane 1:9 to 15:85; SiO$_2$, cyclohexane/Et$_2$O 9:1 to 75:25, SiO$_2$; cyclohexane/acetone 75:25) to give 136 (899.9 mg, 2.61 mmol, 81%) as an orange solid.

R$_f$=0.25 (EtOAc/cyclohexane 2:8); Mp 161° C.; IR (ATR) 3277, 1584, 1506, 1332, 1303, 1215, 998, 758, 719 cm$^{-1}$; $^1$H NMR (400 MHz, DMSO-d$_6$) δ 11.30 (s, 1H), 9.13 (d, J=2.8, 1H), 8.47 (d, J=2.8, 1H), 7.47 (dd, J=6.8 Hz, 2.1, 1H), 7.41 (t, J=2.8, 1H), 7.37-7.24 (m, 5H), 7.21-7.15 (m, 2H), 6.35-6.33 (m, 1H), 5.55 (s, 2H); $^{13}$C NMR (101 MHz, DMSO-d$_6$) δ 163.4 (C), 142.5 (CH), 139.6 (C), 136.2 (C), 136.1 (C), 134.1 (CH), 128.3 (2CH), 127.9 (CH), 127.8 (2CH), 126.4 (C), 126.1 (CH), 125.5 (C), 124.2 (C), 120.8 (CH), 120.2 (CH), 112.1 (CH), 100.2 (CH), 68.8 (CH$_2$); HRMS (ESI+) calcd for C$_{20}$H$_{16}$N$_3$O$_3$ (M+H)$^+$346.1186, found 346.1195.

6-(Benzyloxy)-5-(1H-indol-4-yl)pyridin-3-amine (137)

To a solution of compound 136 (72 mg, 0.208 mmol, 1 eq.) in a 10:1 propan-2-ol/water mixture (4.4 mL) were added Fe powder (70.5 mg, 1.26 mmol, 6.1 eq.) and NH$_4$Cl (4.5 mg, 0.084 mmol, 0.4 eq.). The mixture was refluxed for 1 h 30 min. Then, the mixture was filtered through a pad of Celite and the solid was washed with EtOAc. The filtrate was washed with water, and the aqueous phase was extracted with EtOAc. The organic phase was dried over MgSO$_4$, filtered and then evaporated. The obtained orange oil was purified by column chromatography (SiO$_2$, EtOAc/cyclohexane 3:7 to 5:5) to give 137 (46 mg, 0.146 mmol, 70%) as a brown solid.

R$_f$=0.13 (EtOAc/cyclohexane 3:7); Mp 68° C.; IR (ATR) 3404, 1608, 1582, 1455, 1423, 1407, 1355, 1220, 751, 731, 695 cm$^{-1}$; $^1$H NMR (400 MHz, DMSO-d$_6$) δ 11.13 (s, 1H), 7.54 (d, J=2.8, 1H), 7.36 (dt, J=8.1, 1.0, 1H), 7.33 (t, J=2.8 Hz, 1H), 7.29-7.18 (m, 5H), 7.15 (d, J=2.8, 1H), 7.11 (t, J=7.6, 1H), 7.05 (dd, J=7.3, 1.1, 1H), 6.27 (ddd, J=3.0, 1.9, 1.0, 1H), 5.24 (s, 2H), 4.85 (s, 2H); $^{13}$C NMR (101 MHz, DMSO-d$_6$) δ 152.0 (C), 139.7 (C), 138.2 (C), 136.0 (C), 129.8 (CH), 128.7 (C), 128.0 (2CH), 127.3 (2CH), 127.1 (CH), 126.9 (CH), 126.6 (C), 125.2 (CH), 123.3 (C), 120.6 (CH), 119.9 (CH), 110.7 (CH), 100.8 (CH), 66.5 (CH$_2$); HRMS (ESI+) calcd for C$_{20}$H$_{18}$N$_3$O (M+H)$^+$316.1444, found 316.1446.

6-(Benzyloxy)-N-(2-bromophenyl)-5-(1H-indol-4-yl)pyridin-3-amine (138)

Compound 138 was prepared according to general procedure D, starting from 137 (149.5 mg, 0.474 mmol) in 2.4 mL of anhydrous 1,4-dioxane. The mixture was heated for 24 h. Pd(OAc)$_2$ (0.05 eq.) was added and the mixture was heated for 48 h. PdOAc (0.05 eq.) and Xantphos (0.05 eq.) were added and the mixture was heated for 72 h. The crude oil was purified by two column chromatographies (SiO$_2$, cyclohexane to EtOAc/cyclohexane 15:85 and SiO$_2$, pentane/Et$_2$O 9:1 to 8:2) to give 138 (105.8 mg, 0.225 mmol, 47%) as a white solid.

R$_f$=0.42 (EtOAc/cyclohexane 3:7); Mp 74° C.; IR (ATR) 3384, 3500-3100, 1593, 1494, 1441, 1353, 1021, 744, 728, 693 cm$^{-1}$; $^1$H NMR (400 MHz, DMSO-d$_6$) δ 11.18 (s, 1H), 8.03 (d, J=2.8, 1H), 7.57 (d, J=2.7, 1H), 7.55 (dd, J=8.0, 1.5, 1H), 7.46 (s, 1H), 7.41-7.18 (m, 7H), 7.36 (dd, J=3.1, 2.5, 1H), 7.15-7.10 (m, 2H), 7.06 (dd, J=8.2, 1.6, 1H), 6.79-6.74 (m, 1H), 6.33 (ddd, J=3.0, 2.0, 0.9, 1H), 5.37 (s, 2H); $^{13}$C NMR (101 MHz, DMSO-d$_6$) δ 155.6 (C), 142.9 (C), 137.8 (CH), 137.6 (C), 136.0 (C), 133.5 (CH), 133.3 (C), 133.2 (CH), 128.6 (CH), 128.1 (2CH), 127.7 (C), 127.5 (2CH), 127.4 (CH), 126.5 (C), 125.5 (CH), 123.8 (C), 121.1 (CH), 120.7 (CH), 120.1 (CH), 116.5 (CH), 111.9 (C), 111.1 (CH), 100.6 (CH), 67.0 (CH$_2$); HRMS (ESI+) calcd for C$_{26}$H$_{21}$BrN$_3$O (M+H)$^+$470.0863, found 470.0864.

6-(Benzyloxy)-N-(3-bromophenyl)-5-(1H-indol-4-yl)pyridin-3-amine (139)

Compound 139 was prepared according to general procedure D, starting from 137 (150.2 mg, 0.476 mmol) in 2.4 mL of anhydrous 1,4-dioxane. The mixture was heated for 5 h. The crude oil was purified by column chromatography (SiO$_2$, EtOAc/cyclohexane 1:9 to 15:85) to give 139 (104.1 mg, 0.221 mmol, 46%) as an orange solid.

R$_f$=0.52 (EtOAc/cyclohexane 3:7); Mp>155° C. (decomposition); IR (ATR) 3383, 1589, 1446, 1421, 1406, 1229, 989, 751, 695 cm$^{-1}$; $^1$H NMR (400 MHz, DMSO-d$_6$) δ 11.21 (s, 1H), 8.28 (s, 1H), 8.04 (d, J=2.8, 1 H), 7.60 (d, J=2.8, 1 H), 7.42-7.37 (m, 1H), 7.37 (t, J=2.8, 1H), 7.35-7.21 (m, 5H), 7.16-7.11 (m, 3H), 7.08 (t, J=2.1, 1H), 6.93 (ddd, J=8.3, 2.3, 0.9, 1H), 6.89 (ddd, J=7.9, 1.9, 0.9, 1 H), 6.32 (ddd, J=3.0, 2.0, 1.0, 1H), 5.37 (s, 2H); $^{13}$C NMR (101 MHz, DMSO-d$_6$) δ 155.5 (C), 146.8 (C), 137.6 (C), 136.8 (CH), 136.1 (C), 132.8 (C), 132.6 (CH), 131.2 (CH), 128.2 (2CH), 127.6 (C), 127.5 (2CH), 127.4 (CH), 126.5 (C), 125.6 (CH), 123.9 (C), 122.4 (C), 121.0 (CH), 120.7 (CH), 120.1 (CH), 116.7 (CH), 113.4 (CH), 111.2 (CH), 100.4 (CH), 67.0 (CH$_2$); HRMS (ESI+) calcd for C$_{26}$H$_{21}$BrN$_3$O (M+H)$^+$ 470.0863, found 470.0865.

6-(Benzyloxy)-N-(4-bromophenyl)-5-(1H-indol-4-yl)pyridin-3-amine (140)

Compound 140 was prepared according to general procedure D, starting from 137 (150.8 mg, 0.478 mmol) in 2.4 mL of anhydrous 1,4-dioxane. The mixture was heated for 5 h. The crude oil was purified by two column chromatographies (SiO$_2$, cyclohexane to EtOAc/cyclohexane 2:8 and SiO$_2$, pentane/Et$_2$O 9:1 to 8:2) to give 140 (103.8 mg, 0.221 mmol, 46%) as a beige solid.

R$_f$=0.35 (EtOAc/cyclohexane 3:7); Mp 161° C.; IR (ATR) 3398, 3171, 1586, 1496, 1447, 1353, 1225, 1007, 748, 724, 688 cm$^{-1}$; $^1$H NMR (400 MHz, DMSO-d$_6$) δ 11.19 (s, 1H), 8.21 (s, 1H), 8.03 (d, J=2.8, 1H), 7.57 (d, J=2.8, 1H), 7.42-7.21 (m, 8H), 7.36 (dd, J=3.1, 2.5, 1H), 7.16-7.11 (m, 2H), 6.92 (d, J=8.9, 2H), 6.30 (ddd, J=3.0, 2.0, 1.0, 1H), 5.36 (s, 2H); $^{13}$C NMR (101 MHz, DMSO-d$_6$) δ 155.2 (C), 144.2 (C), 137.6 (C), 136.1 (CH), 136.0 (C), 133.4 (C), 132.0 (CH), 131.9 (2CH), 128.1 (2CH), 127.7 (C), 127.5 (2CH), 127.4 (CH), 126.5 (C), 125.6 (CH), 123.9 (C), 120.7 (CH), 120.1 (CH), 116.8 (2CH), 111.1 (CH), 109.4 (C), 100.5 (CH), 67.0 (CH$_2$); HRMS (ESI+) calcd for C$_{26}$H$_{21}$BrN$_3$O (M+H)$^+$470.0863, found 470.0869.

5-((2-Bromophenyl)amino)-3-(1H-indol-4-yl)pyridin-2(1H)-one (141)

To a solution under argon and cooled to −10° C. of 138 (105 mg, 0.223 mmol) in anhydrous dichloromethane (11 mL) was added dropwise a 1 M BBr$_3$ solution in dichloromethane (4 eq.). The mixture was stirred at 0° C. for 3 h 30 min in the dark. The reaction mixture was then quenched by addition of NEt$_3$ (16 eq.) and MeOH (6 eq.). After evaporation under reduced pressure, EtOAc was added and the mixture was washed with water and an aqueous saturated NaCl solution. The organic phase was dried over MgSO$_4$, and filtered. After evaporation under reduced pressure, the crude was purified by column chromatography (SiO$_2$, CH$_2$Cl$_2$/MeOH 98:2 to 94:6). To eliminate traces of NEt$_3$ salts, CH$_2$Cl$_2$ was added and the solution was washed with an aqueous saturated NaCl solution. The organic phase was dried over MgSO$_4$, filtered and evaporated to give 141 (49.8 mg, 0.131 mmol, 59%) as a beige powder.

R$_f$=0.39 (CH$_2$Cl$_2$/MeOH 95:5+0.5% NEt$_3$); Mp>227° C. (decomposition); IR (ATR) 3500-3000, 1650, 1611, 1589, 1555, 1491, 1449, 1020, 743 cm$^{-1}$; $^1$H NMR (400 MHz, DMSO-d$_6$) δ 11.68 (s, 1H), 11.13 (s, 1H), 7.49 (dd, J=7.9, 1.5, 1H), 7.49 (d, J=3.0 Hz, 1H), 7.36 (dt, J=8.0, 0.9, 1H), 7.33 (t, J=2.7, 1H), 7.29 (br s, 1H), 7.28 (d, J=7.2, 1H), 7.18 (ddd, J=8.8, 7.4, 1.5, 1H), 7.09 (t, J=7.7, 1 H), 7.01 (s, 1H), 6.78 (dd, J=8.1, 1.4, 1H), 6.66 (ddd, J=7.9, 7.3, 1.6, 1H), 6.40-6.38 (m, 1H); $^{13}$C NMR (101 MHz, DMSO-d$_6$) δ 159.9 (C=O), 144.4 (C), 139.4 (CH), 136.1 (C), 132.9 (CH), 130.6 (C), 129.6 (CH), 128.5 (CH), 128.2 (C), 126.1 (C), 125.3 (CH), 121.1 (C), 120.4 (CH), 119.9 (CH), 119.4 (CH), 114.3 (CH), 110.9 (CH), 109.6 (C), 100.5 (CH); HRMS (ESI+) calcd for C$_{19}$H$_{16}$BrN$_3$O (M+H)$^+$380.0393, found 380.0388; HPLC purity≥98%, t$_R$=8.35 min, λ=274 nm.

5-((3-Bromophenyl)amino)-3-(1H-indol-4-yl)pyridin-2(1H)-one (142)

To a solution under argon and cooled to −10° C. of 139 (81 mg, 0.172 mmol) in anhydrous dichloromethane (9 mL)

was added dropwise a 1 M BBr$_3$ solution in dichloromethane (4 eq.). The mixture was stirred at 0° C. for 3 h 30 min in the dark. The reaction mixture was then quenched by addition of NEt$_3$ (21 eq.) and MeOH (7 eq.). After evaporation under reduced pressure, EtOAc was added and the mixture was washed with water and an aqueous saturated NaCl solution. The organic phase was dried over MgSO$_4$, and filtered. After evaporation under reduced pressure, the crude was purified by column chromatography (SiO$_2$, CH$_2$Cl$_2$/MeOH 97:3 to 94:6). To eliminate traces of NEt$_3$ salts, the product was washed with CH$_2$Cl$_2$ to give 142 (44.7 mg, 0.118 mmol, 68%) as light green powder.

R$_f$=0.31 (CH$_2$Cl$_2$/MeOH 95:5+0.5% NEt$_3$); Mp>155° C. (decomposition); IR (ATR) 3500-3000, 1649, 1614, 1588, 1556, 1333, 892, 755 cm$^{-1}$; $^1$H NMR (400 MHz, DMSO-d$_6$) δ 11.64 (br s, 1H), 11.15 (s, 1H), 7.77 (s, 1H), 7.50 (d, J=2.9, 1H), 7.36 (dt, J=8.0, 0.9, 1H), 7.35 (t, J=2.8, 1H), 7.27 (d, J=7.2, 1H), 7.26 (br s, 1H), 7.12-7.07 (m, 2H), 6.89 (t, J=2.1, 1 H), 6.82 (ddd, J=7.9, 2.1, 1.0, 1 H), 6.73 (dd, J=8.3, 2.2, 1 H), 6.37-6.35 (m, 1H); $^{13}$C NMR (101 MHz, DMSO-d$_6$) δ 159.8 (C=O), 148.7 (C), 138.6 (CH), 136.1 (C), 131.1 (CH), 130.8 (C), 128.3 (CH), 128.1 (C), 126.1 (C), 125.4 (CH), 122.4 (C), 121.1 (C), 120.4 (CH), 120.0 (CH), 119.9 (CH), 115.6 (CH), 112.5 (CH), 111.0 (CH), 100.4 (CH); HRMS (ESI+) calcd for C$_{19}$H$_{16}$BrN$_3$O (M+H)$^+$380.0393, found 380.0396; HPLC purity≥99%, t$_R$=8.26 min, λ=278 nm.

5-((4-Bromophenyl)amino)-3-(1H-indol-4-yl)pyridin-2(1H)-one (143)

To a solution under argon and cooled to −10° C. of 140 (74.8 mg, 0.159 mmol) in anhydrous dichloromethane (8 mL) was added dropwise a 1 M BBr$_3$ solution in dichloromethane (4 eq.). The mixture was stirred at 0° C. for 3 h 30 min in the dark. The reaction mixture was then quenched by addition of NEt$_3$ (23 eq.) and MeOH (8 eq.). After evaporation under reduced pressure, EtOAc was added and the mixture was washed with water and an aqueous saturated NaCl solution. The organic phase was dried over MgSO$_4$, and filtered. After evaporation under reduced pressure, the crude was purified by column chromatography (SiO$_2$, CH$_2$Cl$_2$/MeOH 97:3 to 95:5). To eliminate traces of NEt$_3$ salts, the product was washed with CH$_2$Cl$_2$ to give 143 (31.4 mg, 0.083 mmol, 52%) as yellow solid.

R$_f$=0.30 (CH$_2$Cl$_2$/MeOH 95:5+0.5% NEt$_3$); Mp>167° C. (decomposition); IR (ATR) 3500-3000, 1651, 1610, 1586, 1556, 1487, 1333, 752 cm$^{-1}$; $^1$H NMR (400 MHz, DMSO-d$_6$) δ 11.61 (s, 1H), 11.14 (s, 1H), 7.68 (s, 1H), 7.49 (d, J=3.0, 1H), 7.38-7.33 (m, 2H), 7.29 (d, J=8.9, 2H), 7.26 (d, J=7.2, 1H), 7.23 (br s, 1H), 7.09 (t, J=7.7, 1H), 6.71 (d, J=8.9, 2H), 6.36-6.34 (m, 1H); $^{13}$C NMR (101 MHz, DMSO-d$_6$) δ 159.7 (C=O), 146.2 (C), 138.3 (CH), 136.1 (C), 131.8 (2CH), 130.8 (C), 128.2 (C), 127.6 (CH), 126.1 (C), 125.4 (CH), 121.7 (C), 120.4 (CH), 119.9 (CH), 115.6 (2CH), 110.9 (CH), 108.4 (C), 100.5 (CH); HRMS (ESI+) calcd for C$_{13}$H$_{16}$BrN$_3$O (M+H)$^+$380.0393, found 380.0396; HPLC purity≥97%, t$_R$=8.27 min, λ=278 nm.

2. In Vitro Affinity

2.1 p38 Alpha IC50 Results

| Compound | Mean IC50 (micromolar) | s.d. |
|---|---|---|
| 67 | 3.03 | 0.06 |
| 69 | 1.46 | 0.73 |
| 134 | 1.04 | 0.22 |
| 130 | 1.06 | 0.28 |
| 121 | 5.25 | 0.67 |
| 122 | 5.53 | 2.28 |
| 123 | 3.67 | 1.41 |
| 143 | 2.35 | 0.50 |
| 142 | 0.66 | 0.20 |
| 141 | 2.72 | 0.45 |
| 120 | 0.43 | 0.11 |
| 119 | 1.42 | 0.30 |
| 118 | 0.23 | 0.01 |

2.2 Screening of Compounds 67 and 69 Towards a Panel of Protein Kinases

Results are expressed as the mean percentage of residual activity at 10 μM (Table 3) or 1 μM (Table 4). They are illustrated on FIGS. 3 and 4.

TABLE 3

| | Compound 69 | |
|---|---|---|
| | mean % residual activity | SD |
| MKK1 | 112 | 0 |
| JNK1 | 102 | 5 |
| p38a MAPK | 19 | 1 |
| RSK1 | 94 | 11 |
| PDK1 | 103 | 4 |
| PKBa | 107 | 2 |
| SGK1 | 89 | 16 |
| S6K1 | 87 | 19 |
| PKA | 94 | 2 |
| ROCK 2 | 105 | 22 |
| PRK2 | 90 | 9 |
| PKCa | 116 | 14 |
| PKD1 | 92 | 32 |
| MSK1 | 100 | 8 |
| CAMKKb | 95 | 3 |
| CAMK1 | 96 | 7 |
| SmMLCK | 100 | 1 |
| CHK2 | 101 | 25 |
| GSK3b | 105 | 8 |
| PLK1 | 113 | 5 |
| Aurora B | 77 | 7 |
| LKB1 | 83 | 24 |
| AMPK (hum) | 95 | 6 |
| MARK3 | 102 | 1 |
| CK1δ | 98 | 1 |
| CK2 | 94 | 0 |
| DYRK1A | 66 | 9 |
| NEK6 | 102 | 6 |
| TBK1 | 89 | 25 |
| PIM1 | 95 | 6 |
| SRPK1 | 81 | 8 |
| EF2K | 116 | 12 |
| HIPK2 | 96 | 16 |
| PAK4 | 89 | 1 |
| MST2 | 91 | 5 |
| MLK3 | 109 | 2 |
| TAK1 | 68 | 11 |
| IRAK4 | 98 | 0 |
| RIPK2 | 90 | 6 |
| TTK | 81 | 8 |
| Src | 93 | 18 |
| Lck | 108 | 2 |
| BTK | 94 | 22 |
| JAK3 | 107 | 42 |
| SYK | 79 | 3 |
| EPH-A2 | 109 | 23 |
| HER4 | 98 | 34 |

TABLE 3-continued

| | Compound 69 | |
| --- | --- | --- |
| | mean % residual activity | SD |
| IGF-1R | 96 | 2 |
| TrkA | 88 | 4 |
| VEG-FR | 94 | 10 |

TABLE 4

| | Compound 67 | | Compound 69 | |
| --- | --- | --- | --- | --- |
| | mean % residual activity | SD | mean % residual activity | SD |
| ERK1 | 122 | 1 | 120 | 21 |
| ERK2 | 108 | 10 | 109 | 11 |
| ERK5 | 113 | 8 | 101 | 13 |
| ERK8 | 128 | 3 | 144 | 7 |
| JNK1 | 94 | 9 | 115 | 12 |
| JNK2 | 103 | 8 | 103 | 8 |
| JNK3 | 98 | 23 | 115 | 21 |
| p38a MAPK | 59 | 10 | 59 | 15 |
| p38b MAPK | 112 | 13 | 116 | 20 |
| p38g MAPK | 107 | 2 | 103 | 17 |
| p38d MAPK | 113 | 3 | 112 | 12 |
| CDK2-Cyclin A | 111 | 13 | 119 | 4 |
| CDK5 | 101 | 13 | 103 | 3 |

Studies were undertaken to identify the possible biological target(s) of compound 69. The activation in neurons of PK such as PKCγ, ERK or p38 MAPK can contribute to pain hypersensitivity. Therefore, it was decided to screen compound 69 toward a panel of 50 PKs that provide a representative sampling of the human kinome (FIG. 3, Table 3) (*Biochem. J.* 2007, 408, 297-315). In this panel, p38α MAPK was identified as the privileged target, with 19% of kinase residual activity at 10 µM compound concentration. Compound 69 was highly selective over the other protein kinases, as none of them showed a mean residual activity <65% at the same concentration. $IC_{50}$ toward p38α MAPK was determined and found to be in the micromolar range, with a value of 1.5±0.7 µM.

The selectivity of compound 69 was evaluated at 1 µM toward another panel containing all four p38 MAPK isoforms, ERK1, ERK2 as well as other protein kinases close to p38α MAPK in the kinome phylogenetic tree (FIG. 4, Table 4). In addition, compound 67 that also exhibited strong anti-allodynic activity was also evaluated in this screening. The results showed that 69 was selective of p38α MAPK over the other protein kinases tested in this panel, including p38 MAPK isoforms. Compound 67 exhibited the same selectivity profile. Its $IC_{50}$ toward p38α MAPK was determined, showing a value in the micromolar range ($IC_{50}$=3.0±0.1 µM).

Hence, compound 69 appears as a highly selective inhibitor of p38α MAPK when considering the panel of 61 protein kinases evaluated. According to these results, besides not yet identified other biological targets, p38α MAPK could be reasonably considered as a target for this series of pyridin-2(1H)one derivatives, leading to the observed analgesia in the inflammatory and neuropathic rat models of MA.

These data show that Compounds 67 and 69 are selective p38α MAPK inhibitor.

3. In Vivo Efficacy: Anti-Allodynic Activity (MA)

Face Complete Freund's Adjuvant (CFA) Model.

CFA (Becton Dickinson) was dissolved in saline solution containing Tween 80 and paraffin oil and conserved at 4° C. For the behavioral tests, animals were briefly (<2 min) anesthetized using a mask with 2% isoflurane and received a subcutaneous injection of 25 µL of CFA (2.5 mg/kg) solution into the right vibrissa pad using a 27 Ga needle coupled to a 25 µL Hamilton syringe, as described previously. After injection, animals were awakened from anesthesia and placed in the behavioral experimental room, followed by a 120 min mechanical testing period.

Rat model of neuropathic MA: chronic constriction injury of the rat's infraorbital nerve (IoN-CCI).

IoN-CCI was performed following a previously established surgical procedure Vos et al *J. Neurosci.* 1994, 14, 2708-2723. Briefly, after animals were anesthetized using chloral hydrate (400 mg/kg i.p.), IoN was exposed just caudal to the vibrissal pad and two ligatures (4/0 chromic catgut) were loosely tied around the nerve just cranial to its exit from the infraorbital foramen. The ligatures were separated by a 1 mm interval. This procedure was performed under 16×surgical microscope magnification (Jenoptik, Germany) to allow for the control of the degree of nerve constriction. The nerve diameter was only slightly reduced and ligatures diminished, but did not occlude circulation through the superficial vasculature. Skin incision was closed with single suture points (4/0 nylon).

Intracisternal Injection:

For investigating the effects of synthetized compounds upon mechanical allodynia, animals were briefly (<2 min) anesthetized using a mask with 2% isoflurane and received an intracisternal injection of 5 µL of compound (100 µM) or vehicle alone (saline+1% DMSO) using a 10 µL Hamilton syringe [12]. After recovery (<2 min), rats were placed in an observation field (0.6×0.6 m square) under red light for a period test. 6-g von Frey filament was gently applied every 15 or 30 min onto the orofacial region by a first experimenter. The behavioral responses were observed and quantified by a second experimenter (see below).

Behavioral Responses to Normally Innocuous (6-g Von Frey Filament) Mechanical Stimulation.

The behavioral responses procedure was previously developed by Vos et al. 1994. A rat's response to mechanical stimulation consisted of one or more of the following elements: (1) detection, rat turn head toward stimulus; (2) withdrawal reaction, rat pull paw away or turn head away or pull it briskly backward when stimulation is applied (a withdrawal reaction is assumed to include a detection element preceding the head withdrawal and therefore consists of two responses elements); (3) escape/attack, rats avoid further contact with the stimulus, either passively by moving their bodies away from the stimulus, or actively by attacking the tip of the pump; (4) asymmetric grooming, rats display an uninterrupted series of at least three wash strokes directed to the stimulated area.

Figure 1:
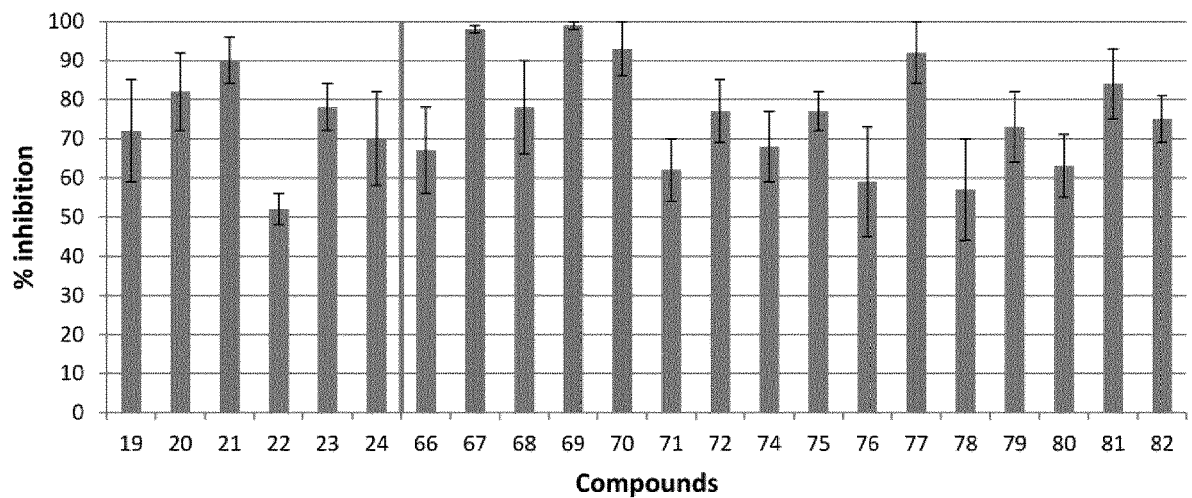
FIG. 1 illustrates the results obtained by the intracisternal application of compounds 19-24, 66-72 and 74-82. These compounds prevent face MA in a rat model of inflammatory pain (Complete Freund's Adjuvant (CFA), n=4-6 rats for each compound). For this assay, compounds (5 µL at 100 µM) or control vehicle were intra-cisternally administred 30 min before CFA injection. Compounds 67 and 69 induced 98% and 99% inhibition of inflammatory MA, respectively.

The in vivo efficacy of some compounds was evaluated on a rat model of inflammatory MA (face CFA model; Alba-Delgado et al *J. Neurosci.* 2018, 38, 10489-10504) (FIG. 1). After receiving a subcutaneous injection of 25 µL of CFA (2.5 mg/kg) into the right vibrissa pad, rats develop a MA that lasts days. It was found that compounds prevented the development of inflammatory MA, for example 19-21, 23, 24, 67-70, 72, 75, 77, 79, 81, 82. The most active pyridinones of this series were 67 and 69 (FIG. 1), bearing at the 3-position an indol-4-yl or a 2-bromophenyl substituent, respectively. In this model of inflammatory MA, MA was suppressed in compound 69 treated rats, in comparison to animals treated with vehicle (FIG. 2A). The results showed that the 3-position of the pyridinone moiety tolerated aryl/ heteroaryl groups, including more sterically demanding groups such as indolyl group. However, branching point of these groups showed their influence on the anti-allodynic activity (compare 22 and 67). In addition, compared to phenyl substituted 19, introduction of a nitrogen atom (21, bearing a pyridine-4-yl moiety) or a methyl group (77) at the 4-position led to comparable gains of activity. Similarly, substitution at the 2-position by a bromine atom (69) or an ethoxycarbonyl group (70) was favorable, with high activities similar to the one of compound 67 bearing an 1H-indol-4-yl substituent.

Compound 69 was also evaluated in a rat model of facial neuropathic MA produced by the constriction injury of the rat infraorbital nerve (IoN-CCI; J. Neurosci. 1994, 14, 2708-2723) (FIG. 2B). Rats develop MA within 2 weeks after constriction which then lasts for several weeks thereafter. Intracisternal administration of compounds 69 on day 14 reversed MA. The effect was fast, confirming the potential of this compound series in neuropathic pain management.

The above results show that the compounds of the invention prevent the development of inflammatory MA in rat CFA model, with a potency depending on the substitution at the 3-position. Hit compound 69, which showed a potent preventing effect in CFA model, also reversed MA in a rat model of facial neuropathic MA. A screening assay using a PK panel identified p38α MAPK as a potential molecular target of the compounds of the invention. These results showed that the 3,5-disubstituted pyridin-2(1H)-ones of the invention are of high interest for the development of novel PK inhibitor analgesics for the treatment of MA or other pain symptoms.

Additional results are illustrated in FIG. 5:

FIG. 5A shows that systemically applied compound 69 can prevent inflammatory mechanical allodynia (MA). Time courses of changes in behavioral responses (allodynic score) evoked by normally innocuous mechanical stimuli (6-g von Frey filament) applied on the face of rats treated with compound 69 (10 mg/kg, intra-peritoneally) or vehicle. Compound 69 or vehicle was preemptively applied 30 min before subcutaneous injection of CFA (at time 0). MA was completely suppressed in compound 69-treated rats. Results are presented as mean±s.e.m.; n=4 in each group. Allodynic score (from 0 to 4) according to Vos et al. J. Neurosci. 1994, 14, 2708-2723.

FIG. 5B shows that compound 69 prevents inflammatory mechanical allodynia (MA) much more effectively than the classic p38 inhibitor: skepinone. Time courses of changes in behavioral responses (allodynic score) evoked by normally innocuous mechanical stimuli (6-g von Frey filament) applied on the face of rats intracisternally treated with compound 69 [5 µL at 10 µM (0.017 µg/animal; dark grey triangles) or 100 µM (0.17 µg; light grey triangles)], skepinone (5 µL containing 60 µg/rat; light grey circles) or vehicle (black circles). Compounds or vehicle were preemptively applied 30 min before subcutaneous injection of CFA (at time 0). MA was completely suppressed in compound 69-treated rats. Moreover, compound 69 appears to be much more potent than skepinone. Results are presented as mean+ s.e.m.; n=4 in each group. Allodynic score (from 0 to 4) according to Vos et al. J. Neurosci. 1994, 14, 2708-2723.

The invention claimed is:
1. A compound of Formula (I):

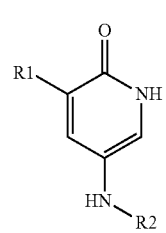

wherein:
R1 is a 4-indolyl group, and
R2 is a group selected from the group consisting of: phenyl optionally substituted by one or more of a halogen atom, O—C1-C6 alkyl, COO—C1-C6 alkyl, $NO_2$, C1-C6 alkyl, OH, $NH_2$; and pyridyl;
or wherein:
R2 is a phenyl group, and,
R1 is a group selected from the group consisting of: pyridyl; pyrimidinyl;
isoquinolinyl; quinolyl; indolyl; and phenyl optionally substituted by one or more of a halogen atom, a COO—C1-C6 alkyl, a CO—C1-C6 alkyl, $CONH_2$, $NO_2$, C1-C6 alkyl, OH, phenyl, $OCF_3$, $CF_3$, or $NH_2$;
or a pharmaceutically acceptable salt thereof.

2. The compound according to claim 1, wherein the compounds is selected from the group consisting of:
3-phenyl-5-(phenylamino)pyridin-2(1H)-one,
3-(4-fluorophenyl)-5-(phenylamino)pyridin-2(1H)-one
5-(phenylamino)-[3,4'-bipyridin]-2(1H)-one,
3-(1H-indol-3-yl)-5-(phenylamino)pyridin-2(1H)-one,
5-(phenylamino)-3-(quinolin-8-yl)pyridin-2(1H)-one,
5-(phenylamino)-3-(pyrimidin-5-yl)pyridin-2(1H)-one,
3-(isoquinolin-5-yl)-5-(phenylamino)pyridin-2(1H)-one
5-(phenylamino)-3-(quinolin-4-yl)pyridin-2(1H)-one,
3-(1H-indol-4-yl)-5-(phenylamino)pyridin-2(1H)-one,
3-(2-chlorophenyl)-5-(phenylamino)pyridin-2(1H)-one,
3-(2-bromophenyl)-5-(phenylamino)pyridin-2(1H)-one,
ethyl 2-(2-oxo-5-(phenylamino)-1,2-dihydropyridin-3-yl)benzoate,
2-(2-oxo-5-(phenylamino)-1,2-dihydropyridin-3-yl)benzamide,
3-(2-nitrophenyl)-5-(phenylamino)pyridin-2(1H)-one,
3-([1,1'-biphenyl]-4-yl)-5-(phenylamino)pyridin-2(1H)-one,
3-(3-chlorophenyl)-5-(phenylamino)pyridin-2(1H)-one,
3-(3-acetylphenyl)-5-(phenylamino)pyridin-2(1H)-one,
3-(4-hydroxyphenyl)-5-(phenylamino)pyridin-2(1H)-one,
5-(phenylamino)-3-(p-tolyl)pyridin-2(1H)-one,
5-(phenylamino)-3-(4-(trifluoromethyl)phenyl)pyridin-2(1H)-one,
5-(phenylamino)-3-(4-(trifluoromethoxy)phenyl)pyridin-2(1H)-one,
Methyl 4-(2-oxo-5-(phenylamino)-1,2-dihydropyridin-3-yl)benzoate,
4-(2-oxo-5-(phenylamino)-1,2-dihydropyridin-3-yl)benzamide,
3-(2,4-difluorophenyl)-5-(phenylamino)pyridin-2(1H)-one,
3-(1H-indol-7-yl)-5-(phenylamino)pyridin-2(1H)-one,
3-(3-aminophenyl)-5-(phenylamino)pyridin-2(1H)-one,
5-((3-hydroxyphenyl)amino)-3-(1H-indol-4-yl)pyridin-2(1H)-one, 5-((2-fluorophenyl)amino)-3-(1H-indol-4-yl)pyridin-2 (1H)-one,
5-((3-fluorophenyl)amino)-3-(1H-indol-4-yl)pyridin-2 (1H)-one,
5-((4-fluorophenyl)amino)-3-(1H-indol-4-yl)pyridin-2 (1H)-one,
3-(1H-indol-4-yl)-5-((2-methoxyphenyl)amino) pyridin-2(1H)-one,
3-(1H-Indol-4-yl)-5-((3-methoxyphenyl)amino) pyridin-2(1H)-one,
3-(1H-indol-4-yl)-5-((4-methoxyphenyl)amino) pyridin-2(1H)-one,
ethyl 2-((5-(1H-indol-4-yl)-6-oxo-1,6-dihydropyridin-3-yl)amino) benzoate
ethyl 3-((5-(1H-indol-4-yl)-6-oxo-1,6-dihydropyridin-3-yl)amino) benzoate,
ethyl 4-((5-(1H-indol-4-yl)-6-oxo-1,6-dihydropyridin-3-yl)amino) benzoate,
3-(1H-indol-4-yl)-5-((2-nitrophenyl)amino)pyridin-2 (1H)-one,
3-(1H-indol-4-yl)-5-((3-nitrophenyl)amino)pyridin-2 (1H)-one,
3-(1H-indol-4-yl)-5-((4-nitrophenyl)amino)pyridin-2 (1H)-one,
3-(1H-indol-4-yl)-5-(o-tolylamino)pyridin-2(1H)-one,
3-(1H-indol-4-yl)-5-(pyridin-2-ylamino)pyridin-2(1H)-one,
3-(1H-indol-4-yl)-5-(pyridin-3-ylamino)pyridin-2(1H)-one,
3-(1H-indol-4-yl)-5-(pyridin-4-ylamino)pyridin-2(1H)-one,
5-((3-hydroxyphenyl)amino)-3-(1H-indol-4-yl)pyridin-2 (1H)-one,
5-((2-aminophenyl)amino)-3-(1H-indol-4-yl)pyridin-2 (1H)-one,
5-((2-bromophenyl)amino)-3-(1H-indol-4-yl)pyridin-2 (1H)-one,
5-((3-bromophenyl)amino)-3-(1H-indol-4-yl)pyridin-2 (1H)-one,
5-((4-bromophenyl)amino)-3-(1H-indol-4-yl)pyridin-2 (1H)-one,
3-(2-aminophenyl)-5-(phenylamino)pyridin-2(1H)-one,
5-((2-hydroxyphenyl)amino)-3-(1H-indol-4-yl)pyridin-2 (1H)-one,
5-((4-hydroxyphenyl)amino)-3-(1H-indol-4-yl)pyridin-2 (1H)-one and
5-((3-aminophenyl)amino)-3-(1H-indol-4-yl)pyridin-2 (1H)-one
and pharmaceutically acceptable salts thereof.

3. A process of preparation of a compound according claim 1, comprising the step of deprotecting a compound of Formula (II):

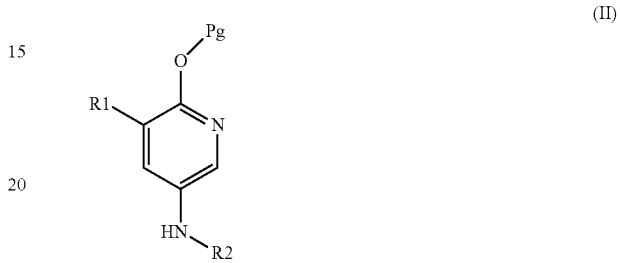

(II)

wherein Pg is a hydroxyl protecting group.

4. The process according to claim 3, wherein the step of deprotecting is performed in the presence of BBr$_3$, TMSI or by catalytic hydrogenation.

5. A pharmaceutical composition comprising
a compound of Formula (I) according to claim 1 and
one or more pharmaceutically acceptable excipients.

6. A method for treating and/or preventing pain in a subject in need thereof, comprising
administering to the subject a therapeutically effective amount of a compound of claim 1.

7. The method according to claim 6 wherein said pain is inflammatory pain, neuropathic pain, cancer pain, visceral pain, headache, migraine, or spontaneous pain.

8. The method according to claim 6, wherein said pain is mechanical allodynia.

* * * * *